US012617760B2

(12) United States Patent
Müller et al.

(10) Patent No.: US 12,617,760 B2
(45) **Date of Patent: *May 5, 2026**

(54) [(5-PHENYL-1-HETEROARYL-1H-TRIAZOL-3-YL)OXY] ACETIC ACID DERIVATIVES AS SAFENERS FOR THE PROTECTION OF USEFUL PLANTS AND CROP PLANTS

(71) Applicant: BAYER AKTIENGESELLSCHAFT, Leverkusen (DE)

(72) Inventors: Thomas Müller, Frankfurt (DE); Anna Maria Reingruber, Heppenheim (DE); Jens Frackenpohl, Frankfurt (DE); Hendrik Helmke, Liederbach (DE); Jan Dittgen, Frankfurt (DE)

(73) Assignee: BAYER AKTIENGESELLSCHAFT, Leverkusen (DE)

( * ) Notice: Subject to any disclaimer, the term of this patent is extended or adjusted under 35 U.S.C. 154(b) by 349 days.

This patent is subject to a terminal disclaimer.

(21) Appl. No.: 18/250,600

(22) PCT Filed: Nov. 2, 2021

(86) PCT No.: PCT/EP2021/080352

§ 371 (c)(1),
(2) Date: Apr. 26, 2023

(87) PCT Pub. No.: WO2022/096442

PCT Pub. Date: May 12, 2022

(65) Prior Publication Data

US 2023/0382874 A1 Nov. 30, 2023

(30) Foreign Application Priority Data

Nov. 5, 2020 (EP) .................................... 20206041

(51) Int. Cl.
*A01N 25/32* (2006.01)
*C07D 249/10* (2006.01)
*C07D 249/12* (2006.01)

(52) U.S. Cl.
CPC ........... *C07D 249/12* (2013.01); *A01N 25/32* (2013.01)

(58) Field of Classification Search
CPC ..... C07D 249/12; C07D 249/10; A01N 25/32
See application file for complete search history.

(56) References Cited

U.S. PATENT DOCUMENTS

| | | | | |
|---|---|---|---|---|
| 4,931,083 | A | 6/1990 | Beck et al. | |
| 2008/0125409 | A1 | 5/2008 | Kanaya et al. | |
| 2022/0388971 | A1* | 12/2022 | Mueller | C07D 405/12 |
| 2023/0167088 | A1 | 6/2023 | Jakobi | |
| 2023/0382874 | A1* | 11/2023 | Müller | A01N 25/32 |
| 2023/0397604 | A1* | 12/2023 | Müller | C07D 405/14 |
| 2023/0416229 | A1* | 12/2023 | Müller | C07D 401/14 |

FOREIGN PATENT DOCUMENTS

| | | | |
|---|---|---|---|
| CN | 101284815 | A | 10/2008 |
| CN | 102093344 | A | 6/2011 |
| DE | 2828529 | A1 | 1/1980 |
| EP | 0268554 | A2 | 5/1988 |
| EP | 0310555 | A1 | 4/1989 |
| WO | 2004084631 | A1 | 10/2004 |
| WO | 2005015994 | A1 | 2/2005 |
| WO | 2005112630 | A1 | 12/2005 |
| WO | 2006040016 | A1 | 4/2006 |
| WO | 2008073825 | A1 | 6/2008 |
| WO | 2008080504 | A2 | 7/2008 |
| WO | 2008131860 | A2 | 11/2008 |
| WO | 2021105101 | A1 | 6/2021 |

OTHER PUBLICATIONS

Guolin Wu et al., Synthesis and structure-activity relationship studies of MI-2 analogues as MALT1 inhibitors, Bioorganic Medicinal Chemistry, 2018, pp. 3321-3344.
M. Struga et al., Synthesis of New Derivatives of 1, 2, 4-Triazol-3-one, Polish J. Chem., 2006, pp. 889-897, vol. 80.
Rosinger, et al., "Safener for Herbicides", Modern Crop Protection Compounds, 2007, Wiley VCH, Seiten 259-281.
Written Opinion from PCT Application No. PCT/EP2021/080352, mailed Jan. 14, 2022.
International Search Report issued in corresponding PCT/EP2020/083167 application on Nov. 1, 2021.
Li, et al., "Crystal Structures, Vibrational Spectra, and Fungicidal Activity of 1,5-Diaryl-3-oxypyrazoles", Molecules, 2014, 19, 1302-1316.
Liu et al., "DMF-Catalyzed Direct and Regioselective C—H Functionalization: Electrophilic/Nucleophilic 4-Halogenation of 3-Oxypyrazoles," European Journal of Organic Chemistry, 2011, pp. 5323-5330 (8 pages), XP002798741.

(Continued)

*Primary Examiner* — Bethany P Barham
*Assistant Examiner* — Danielle Johnson
(74) *Attorney, Agent, or Firm* — Michael VanEngelen

(57) ABSTRACT

The present invention relates to crop protection compounds and to compositions which comprise specific compounds as safeners for reducing phytotoxic effects of agrochemicals, especially herbicides.

The invention relates more particularly to certain [5-(phenyl)-1-(heteroaryl)-1H-1,2,4-triazol-3-yl)oxy] acetic acid derivatives of the general formula (I)

(I)

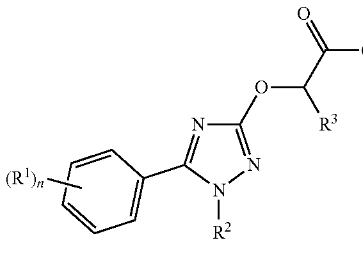

and their salts, to processes for preparing them and to their use as plant protection compounds (safeners).

16 Claims, No Drawings

(56) References Cited

OTHER PUBLICATIONS

Liu, Yuanyuan et al., "Synthesis, Crystal Structure, and Fungicidal Activity of Novel 1,5-Diaryl-1H-Pyrazol-3-Oxy Derivatives Containing Oxyacetic Acid or Oxy(2-thioxothiazolidin-3-yl)ethanone Moieties," Journal of Heterocyclic Chemistry, 2012, pp. 1370-1375, vol. 49.
Written Opinion from PCT Application No. PCT/EP2020/083167, mailed Jan. 11, 2021.
Written Opinion from PCT Application No. PCT/EP2021/080357, mailed Jan. 14, 2022.
Written Opinion from PCT Application No. PCT/EP2021/080358, mailed Jan. 14, 2022.
Written Opinion from PCT Application No. PCT/EP2021/080360, mailed Jan. 14, 2022.
Written Opinion from PCT Application No. PCT/EP2021/080361, mailed Jan. 14, 2022.
Written Opinion from PCT Application No. PCT/EP2021/080362, mailed Jan. 24, 2022.
Yang, "Ethyl 2-{[5-(3-chlorophenyl)-1-phenyl-1H-pyrazol-3-yl]oxy}acetate", Acta Crystallographica Section E, 2012, 68 (1).
Yuanyuan Liu et al., Synthesis, Crystal Structure, and Fungicidal Activity of Novel 1,5-Diaryl-1/1-pyrazol-3-oxyacetate Derivatives, Jul. 2010, pp. 897-902, vol. 47, Journal of Heterocyclic Chemistry.
Li, et al., "2-(1,5-Diphenyl-1H-pyrazol-3-yloxy)-1-(2-sulfanylidene-1,3-thiazolidin-3-yl)-ethanone", Acta Crystallogrphica, Section E Structure Reports, 2012, 68(8).
Patani, G. 'Bioisosterism: A Rational Approach in Drug Design,' 1996, Chern. Rev., vol. 96, p. 3147-3176. American ChemicalSociety. (Year: 1996).

* cited by examiner

[(5-PHENYL-1-HETEROARYL-1H-TRIAZOL-3-YL)OXY] ACETIC ACID DERIVATIVES AS SAFENERS FOR THE PROTECTION OF USEFUL PLANTS AND CROP PLANTS

The present application is a 35 U.S.C. § 371 national phase entry of International Application No. PCT/EP2021/080352, filed on Nov. 2, 2021, which claims priority to European Patent Application No. 20206041.4, filed Nov. 5, 2020, the contents of each of which are hereby incorporated by reference in their entirety.

The present invention relates to useful plant-protecting compounds and compositions comprising specific compounds as safeners for reduction of phytotoxic effects of agrochemicals, especially of herbicides. More particularly, the invention relates to particular [(5-phenyl-1-(heteroaryl)-1H-1,2,4-triazol-3-yl)oxy]acetic acid derivatives and salts thereof as safeners and to processes for preparation thereof.

In the control of unwanted organisms in horticultural and sivicultural useful plant crops with pesticides, the useful plants are frequently also damaged to a greater or lesser degree by the pesticides used, such as herbicides, insecticides, fungicides inter alia. This unwanted phytotoxic side effect occurs to a particular degree when numerous herbicides are used—primarily in post-emergence application—in useful plant crops, for example maize, rice or cereal. The use of "safeners" or "antidotes" can in some cases protect the useful plants against the phytotoxic properties of the pesticides without reducing or significantly impairing the pesticidal action with respect to the harmful organisms. In some cases, in the presence of safeners, improved pesticidal action against harmful organisms such as weeds has even been observed.

The compounds that have become known to date as safeners are among a large number of different chemical structure classes, the suitability of which for use as safeners generally also depends on the chemical structures of the pesticides and on the useful plant crops.

Safener effects of compounds from the group of the derivatives of phenoxy- or heteroaryloxyalkanecarboxylic acids have long been known if these compounds are employed in combination with herbicides. Examples of such compounds are MCPA and similar compounds, which at the same time are still herbicidally active against harmful plants, or cloquintocet-mexyl.

Also known are safeners from the group of the derivatives of N-phenyl-substituted heteroarylcarboxylic esters with multiple heteroatoms in the heteroaromatic system. Examples of such safeners are the mefenpyr-diethyl and isoxadifen-ethyl safeners that are used in commercial products.

WO 2004/084631 discloses the use of hydroxy-substituted aromatic carboxylic acid derivatives. WO 2005/015994 describes specific derivatives of salicylic acid as safeners. These are particularly suitable for use as safener in maize and soya crops.

In addition, WO 2005/112630 discloses 1,2-dihydroquinoxalin-2-one derivatives, and WO 2008/131860 discloses pyridonecarboxamides as safeners.

Active ingredients from the chemical class of the [(5-phenyl-1-(heteroaryl)-1H-1,2,4-triazol-3-yl)oxy]acetic acid derivatives with plant-active properties are not known from the literature.

Various documents describe [(1,5-diphenyl-1H-1,2,4-triazol-3-yl)oxy]acetic acid derivatives having medical properties. Polish J. Chem. 2006, 80, 889-897 and Bioorganic & Medicinal Chemistry 2018, 26, 3321-3344 disclose [(1,5-diphenyl-1H-1,2,4-triazol-3-yl)oxy] acetic acid derivatives.

When safeners are used for protection of crop plants from damage by pesticides, it has been found that the known safeners can have disadvantages in many cases. These include:

- the useful plant-protecting properties are inadequate,
- in combination with a particular herbicide, the spectrum of useful plants in which the safener/herbicide are to be used is insufficiently large,
- a particular safener is combinable with only a few herbicides,
- the use of safeners increases the application rate to be applied and amount of formulation auxiliaries, and can thus cause application-related problems.

For the reasons mentioned, there is an increased need for the provision of alternative compounds having safener action.

The invention provides novel useful plant-protecting compounds of the general formula (I) or salts thereof (I)

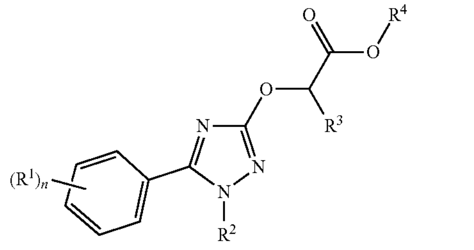

for reduction of phytotoxic effects of pesticides, especially of herbicides, on useful plants or crop plants, in which $R^1$ is hydrogen, halogen, cyano, nitro, $(C_1-C_6)$alkyl, $(C_2-C_6)$alkenyl, $(C_2-C_6)$alkynyl, $(C_3-C_8)$cycloalkyl, $(C_3-C_8)$cycloalkenyl, $(C_1-C_6)$alkoxy and $(C_1-C_6)$alkylS$(O)_p$, where the latter seven radicals are unsubstituted or are substituted by one or more radicals from the group of halogen, cyano, $(C_1-C_6)$alkoxy and $(C_1-C_6)$alkylS$(O)_p$, $R^2$ is heteroaryl, where the heteroaryl radical is an unsubstituted or substituted by halogen, cyano, nitro, $(C_1-C_6)$alkyl, $(C_2-C_6)$alkenyl, $(C_2-C_6)$alkynyl, $(C_3-C_8)$cycloalkyl, $(C_3-C_8)$cycloalkenyl, $(C_1-C_6)$alkoxy and $(C_1-C_6)$alkylS$(O)_p$, where the latter seven radicals are unsubstituted or are substituted by one already more radicals from the group of halogen, cyano, $(C_1-C_6)$alkoxy and $(C_1-C_6)$alkylS$(O)_p$, $R^3$ is hydrogen and $(C_1-C_6)$alkyl, $R^4$ is hydrogen, $(C_1-C_{18})$alkyl, $(C_1-C_{18})$halo alkyl, $(C_1-C_{18})$cyanoalkyl, $(C_2-C_{18})$alkenyl, $(C_2-C_{18})$alkynyl, $(C_3-C_{12})$cyclo alkyl, $(C_3-C_{12})$cycloalkenyl, aryl, heteroaryl, $(C_1-C_{18})$alkoxy $(C_1-C_{18})$alkyl, $(C_1-C_{18})$haloalkoxy-$(C_1-C_{18})$alkyl, $(C_1-C_{18})$alkoxy-$(C_1-C_{18})$haloalkyl, $(C_1-C_{18})$alkyl-thio-$(C_1-C_{18})$alkyl, $(C_1-C_{18})$haloalkylthio-$(C_1-C_{18})$alkyl, $(C_2-C_{18})$haloalkenyl, $(C_2-C_{18})$halo-alkynyl, heterocyclyl-$(C_1-C_{18})$alkyl, aryl-$(C_1-C_{18})$alkyl, $(C_3-C_{12})$cycloalkyl-$(C_1-C_{18})$alkyl, $(C_1-C_{18})$alkoxycarbonyl-$(C_1-C_{18})$alkyl, and $(C_1-C_{18})$alkoxycarbonyl-$(C_3-C_{12})$cycloalkyl-$(C_1-C_{18})$alkyl, or a radical of the formula $—NR^aR^b$ or $—N{=}CR^cR^d$, where, in the former 2 radicals, each of the $R^a$, $R^b$, $R^c$ and $R^d$ radicals is independently hydrogen, $(C_1-C_4)$ alkyl, $(C_2-C_4)$alkenyl, $(C_2-C_4)$alkynyl, benzyl, substituted benzyl, phenyl or substituted phenyl, or $R^a$ and $R^b$ together with the nitrogen atom may form a 3- to 8-membered heterocycle which may contain one or two further ring heteroatoms from the group of N, O and S, but not in the case of a 3- or 4-membered heterocycle, and which is unsubstituted or substituted by one or more radicals from the group of $(C_1-C_4)$alkyl and $(C_1-C_4)$haloalkyl, or $R^c$ and $R^d$ together with the carbon atom are a 3- to 8-membered carbocyclic or heterocyclic radical which may contain 1 to 3 ring heteroatoms from the group of N, O and S, where the carbocyclic or heterocyclic radical is unsubstituted or substituted by one or more radicals from the group of $(C_1-C_4)$-alkyl and $(C_1-C_4)$-haloalkyl, n is a number from 0 to 5, and p is 0, 1 or 2.

The compounds of the general formula (I) can form salts by addition of a suitable inorganic or organic acid, for example mineral acids, for example HCl, HBr, $H_2SO_4$, $H_3PO_4$ or $HNO_3$, or organic acids, for example carboxylic acids such as formic acid, acetic acid, propionic acid, oxalic acid, lactic acid or salicylic acid or sulfonic acids, for example p-toluenesulfonic acid, onto a basic group, for example amino, alkylamino, dialkylamino, piperidino, morpholino or pyridino. These salts then contain the conjugate base of the acid as anion. Suitable substituents in deprotonated form, for example sulfonic acids, particular sulfonamides or carboxylic acids, are capable of forming internal salts with groups, such as amino groups, which are themselves protonatable. Salts may also be formed by action of a base on compounds of the general formula (I). Suitable bases are, for example, organic amines such as trialkylamines, morpholine, piperidine and pyridine, and the hydroxides, carbonates and hydrogencarbonates of ammonium, alkali metals or alkaline earth metals, especially sodium hydroxide, potassium hydroxide, sodium carbonate, potassium carbonate, sodium hydrogencarbonate and potassium hydrogencarbonate. These salts are compounds in which the acidic hydrogen is replaced by an agriculturally suitable cation, for example metal salts, especially alkali metal salts or alkaline earth metal salts, in particular sodium and potassium salts, or else ammonium salts, salts with organic amines or quaternary ammonium salts, for example with cations of the formula $[NR^iR^{ii}R^{iii}R^{iv}]^+$ in which $R^i$ to $R^{iv}$ are each independently an organic radical, especially alkyl, aryl, arylalkyl or alkylaryl. Also useful are alkylsulfonium and alkylsulfoxonium salts, such as $(C_1-C_4)$-trialkylsulfonium and $(C_1-C_4)$-trialkylsulfoxonium salts.

The compounds of the formula (I) used in accordance with the invention and salts thereof are referred to hereinafter as "compounds of the general formula (I)".

The invention preferably provides compounds of the general formula (I) in which $R^1$ is hydrogen, halogen, cyano, nitro, $(C_1-C_4)$alkyl, $(C_2-C_4)$alkenyl, $(C_2-C_4)$alkynyl, $(C_3-C_6)$cycloalkyl, $(C_3-C_6)$cycloalkenyl, $(C_1-C_4)$alkoxy and $(C_1-C_4)$alkylS$(O)_p$, where the latter seven radicals are unsubstituted or are substituted by one already more radicals from the group of halogen, cyano, $(C_1-C_4)$alkoxy and $(C_1-C_4)$alkylS$(O)_p$, $R^2$ is heteroaryl, where the heteroaryl radical is unsubstituted or substituted by halogen, cyano, nitro, $(C_1-C_6)$alkyl, $(C_2-C_6)$alkenyl, $(C_2-C_4)$alkynyl, $(C_3-C_6)$cycloalkyl, $(C_3-C_6)$cycloalkenyl, $(C_1-C_4)$alkoxy and $(C_1-C_4)$alkylS$(O)_p$, where the latter seven radicals are unsubstituted or are substituted by one already more radicals from the group of halogen, cyano, $(C_1-C_4)$alkoxy and $(C_1-C_4)$alkylS$(O)_p$, $R^3$ is hydrogen and $(C_1-C_4)$alkyl, $R^4$ is hydrogen, $(C_1-C_{16})$alkyl, $(C_1-C_{16})$halo alkyl, $(C_1-C_{16})$cyanoalkyl, $(C_2-C_{16})$alkenyl, $(C_2-C_{16})$alkynyl, $(C_3-C_{12})$cycloalkyl, $(C_3-C_{12})$cycloalkenyl, aryl, heteroaryl, $(C_1-C_{16})$alkoxy-$(C_1-C_{16})$alkyl, $(C_1-C_{16})$haloalkoxy-$(C_1-C_{16})$alkyl, $(C_1-C_{16})$alkoxy-$(C_1-C_{16})$haloalkyl, $(C_1-C_{16})$alkyl-thio-(C i-$C_{16}$)alkyl, $(C_1-C_{16})$haloalkylthio-$(C_1-C_{16})$alkyl, $(C_2-C_{16})$haloalkenyl, $(C_2-C_{16})$halo-alkynyl, heterocyclyl-$(C_1-C_{16})$alkyl, aryl-$(C_1-C_{16})$alkyl, $(C_3-C_{12})$cycloalkyl-$(C_1-C_{16})$alkyl, $(C_1-C_{16})$alkoxycarbonyl-$(C_1-C_{16})$alkyl, and $(C_1-C_{16})$alkoxycarbonyl-$(C_3-C_{12})$cycloalkyl-$(C_1-C_{16})$alkyl, n is a number from 0 to 4, and p is 0, 1 or 2.

The invention very particularly preferably provides compounds of the general formula (I) in which $R^1$ is hydrogen, halogen, cyano, methyl, ethyl, $CF_3$, $CF_2Cl$, $CH_2F$, $CHF_2$, $OCH_3$, $OCF_3$, $SCH_3$, $SOCH_3$, $SO_2CH_3$ and $SCF_3$, $R^2$ is heteroaryl, where the heteroaryl radical is unsubstituted or mono- or polysubstituted by halogen, cyano, methyl, ethyl, $CF_3$, $CF_2Cl$, $CH_2F$, $CHF_2$, $OCH_3$, $OCF_3$, $SCH_3$, $SOCH_3$, $SO_2CH_3$ and $SCF_3$, $R^3$ is hydrogen, $CH_2CH_3$ and $CH_3$, $R^4$ is hydrogen, $(C_1-C_{12})$alkyl, $(C_1-C_{12})$halo alkyl, $(C_1-C_{12})$cyanoalkyl, $(C_2-C_{12})$alkenyl, $(C_2-C_{12})$alkynyl, $(C_3-C_{12})$cycloalkyl, $(C_3-C_{12})$cycloalkenyl, aryl, heteroaryl, $(C_1-C_{12})$alkoxy-$(C_1-C_{12})$alkyl, $(C_1-C_{12})$haloalkoxy-$(C_1-C_{12})$alkyl, $(C_1-C_{12})$alkoxy-$(C_1-C_{12})$haloalkyl, $(C_1-C_{12})$alkyl-thio-$(C_1-C_{12})$alkyl, $(C_1-C_{12})$haloalkylthio-$(C_1-C_{12})$alkyl, $(C_2-C_{12})$haloalkenyl, $(C_2-C_{12})$halo-alkynyl, heterocyclyl-$(C_1-C_{12})$alkyl, aryl-$(C_1-C_{12})$alkyl, $(C_3-C_{12})$cycloalkyl-$(C_1-C_{12})$alkyl, $(C_1-C_{12})$alkoxycarbonyl-$(C_1-C_{12})$alkyl, and $(C_1-C_{12})$alkoxycarbonyl-$(C_3-C_{12})$cycloalkyl-$(C_1-C_{12})$alkyl, and n is 0, 1, 2 or 3.

The invention especially preferably provides compounds of the general formula (I) in which $R^1$ is hydrogen, fluorine, chlorine, bromine, iodine, CN, methyl, ethyl, $CF_3$, $CF_2Cl$, $CH_2F$, $CHF_2$, $OCH_3$, $OCF_3$, $SCH_3$, $SOCH_3$, $SO_2CH_3$ and $SCF_3$, $R^2$ is pyridin-2-yl, pyridin-3-yl, pyridin-4-yl, pyrazin-2-yl, pyrazin-3-yl, pyrimidin-2-yl, pyrimidin-4-yl, pyrimidin-5-yl, pyridazin-3-yl, pyridazin-4-yl, 1,3,5-triazin-2-yl, 1,2,4-triazin-3-yl, 1,2,4-triazin-5-yl, 1,2,4-triazin-6-yl, 1,2,3-triazin-4-yl, 1,2,3-triazin-5-yl, 1,2,4-, 1,3,2-, 1,3,6- and 1,2,6-oxazinyl, isoxazol-3-yl, isoxazol-4-yl, isoxazol-5-yl, 1,3-oxazol-2-yl, 1,3-oxazol-4-yl, 1,3-oxazol-5-yl, isothiazol-3-yl, isothiazol-4-yl, isothiazol-5-yl, 1,3-thiazol-2-yl, 1,3-thiazol-4-yl, 1,3-thiazol-5-yl, 1H-pyrrol-1-yl; 1H-pyrrol-2-yl; 1H-pyrrol-3-yl, furan-2-yl; furan-3-yl, thien-2-yl, thien-3-yl, 1H-imidazol-1-yl, 1H-imidazol-2-yl, 1H-imidazol-4-yl, 1H-imidazol-5-yl, 1H-pyrazol-1-yl, 1H-pyrazol-3-yl, 1H-pyrazol-4-yl, 1H-pyrazol-5-yl, 1H-1,2,3-triazol-1-yl, 1H-1,2,3-triazol-4-yl, 1H-1,2,3-triazol-5-yl, 2H-1,2,3-triazol-2-yl, 2H-1,2,3-triazol-4-yl, 1H-1,2,4-triazol-1-yl, 1H-1,2,4-triazol-5-yl, 4H-1,2,4-triazol-3-yl, 1,2,4-oxadiazol-3-yl, 1,2,4-oxadiazol-5-yl, 1,3,4-oxadiazol-2-yl, 1,2,3-oxadiazol-4-yl, 1,2,3-oxadiazol-5-yl, 1,2,5-oxadiazol-3-yl, 1,3,4-thiadiazol- 2-yl, 1,3,4-thiadiazol-2-yl, 1,2,4-thiadiazol-5-yl, 1,2,4-thiadiazol-3-yl, 1,2,5-thiadiazol-3-yl, 1,2,5-thiadiazol-3-yl, 1,2,3-thiadiazol-4-yl, 1,2,3-thiadiazol-3-yl, which is unsubstituted or mono- or polysubstituted by halogen, cyano, methyl, $CF_3$, $CF_2Cl$, $CH_2F$, $CHF_2$, $OCH_3$, $OCF_3$, $SCH_3$, $SOCH_3$, $SO_2CH_3$ and $SCF_3$, $R^3$ is hydrogen and $CH_3$, $R^4$ is hydrogen, $(C_1\text{-}C_{10})$alkyl, $(C_1\text{-}C_{10})$haloalkyl, $(C_1\text{-}C_{10})$cyanoalkyl, $(C_2\text{-}C_{10})$alkenyl, $(C_2\text{-}C_{10})$alkynyl, $(C_3\text{-}C_9)$cycloalkyl, $(C_3\text{-}C_9)$cycloalkenyl, aryl, heteroaryl, $(C_1\text{-}C_{10})$alkoxy-$(C_1\text{-}C_{10})$alkyl, $(C_1\text{-}C_{10})$haloalkoxy-$(C_1\text{-}C_{10})$alkyl, $(C_1\text{-}C_{10})$alkoxy-$(C_1\text{-}C_{10})$haloalkyl, $(C_1\text{-}C_{10})$alkyl-thio-$(C_1\text{-}C_{10})$alkyl, $(C_1\text{-}C_{10})$haloalkylthio-$(C_1\text{-}C_{10})$alkyl, $(C_2\text{-}C_{18})$haloalkenyl, $(C_2\text{-}C_{18})$halo-alkynyl, heterocyclyl-$(C_1\text{-}C_{10})$alkyl, aryl-$(C_1\text{-}C_{10})$alkyl, $(C_3\text{-}C_9)$cycloalkyl-$(C_1\text{-}C_{10})$alkyl, $(C_1\text{-}C_{10})$alkoxycarbonyl-$(C_1\text{-}C_{10})$alkyl and $(C_1\text{-}C_{10})$alkoxycarbonyl-$(C_3\text{-}C_9)$cyclo alkyl-$(C_1\text{-}C_{10})$alkyl, and n is 0, 1, 2 or 3.

The invention very especially preferably provides compounds of the general formula (I) in which $R^1$ is hydrogen, fluorine, chlorine, bromine, iodine, cyano, methyl, $CF_3$, $CH_2F$, $CHF_2$, $OCH_3$, $OCF_3$, $SCH_3$, $SOCH_3$, $SO_2CH_3$ and $SCF_3$, $R^2$ is the groups Q-2.1 to Q-2.60

Q-2.1

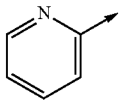

Q-2.2

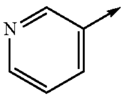

Q-2.3

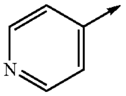

Q-2.4

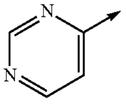

Q-2.5

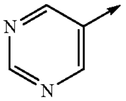

Q-2.6

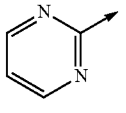

Q-2.7

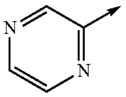

Q-2.8

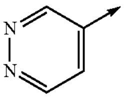

-continued

Q-2.9

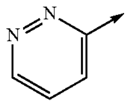

Q-2.10

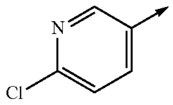

Q-2.11

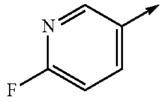

Q-2.12

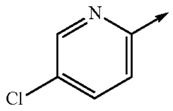

Q-2.13

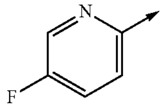

Q-2.14

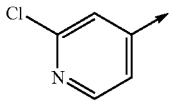

Q-2.15

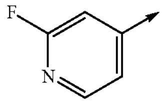

Q-2.16

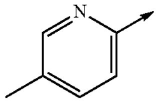

Q-2.17

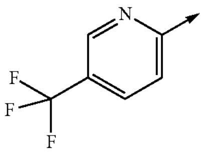

Q-2.18

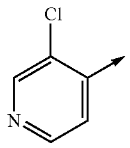

Q-2.19

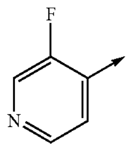

Q-2.20

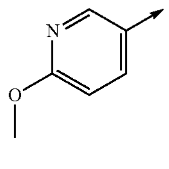

-continued
Q-2.21
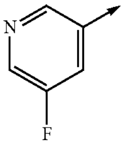
Q-2.22
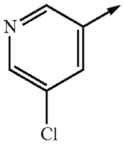
Q-2.23
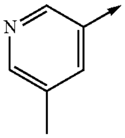
Q-2.24
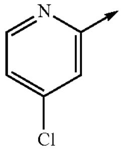
Q-2.25
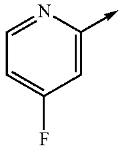
Q-2.26
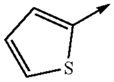
Q-2.27
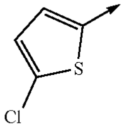
Q-2.28
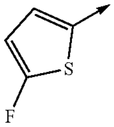
Q-2.29
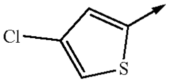
Q-2.30
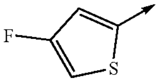
Q-2.31
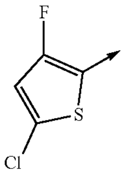
-continued
Q-2.32
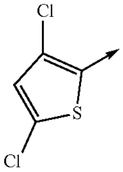
Q-2.33
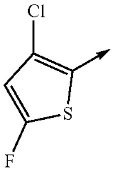
Q-2.34
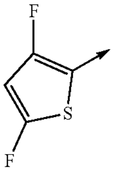
Q-2.35
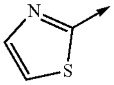
Q-2.36
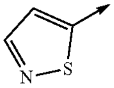
Q-2.37
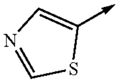
Q-2.38
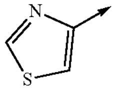
Q-2.39
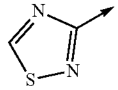
Q-2.40
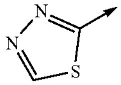
Q-2.41
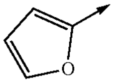
Q-2.42
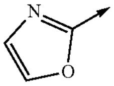
Q-2.43
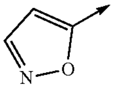
Q-2.44
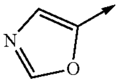

-continued

Q-2.45

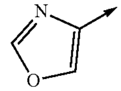

Q-2.46

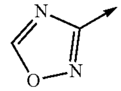

Q-2.47

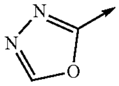

Q-2.48

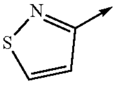

Q-2.49

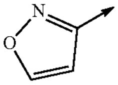

Q-2.50

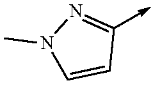

Q-2.51

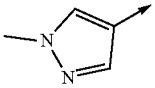

Q-2.52

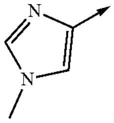

Q-2.53

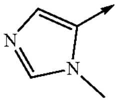

Q-2.54

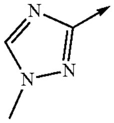

Q-2.55

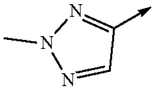

Q-2.56

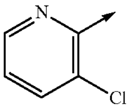

Q-2.57

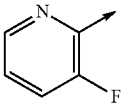

Q-2.58

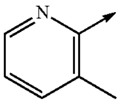

-continued

Q-2.59

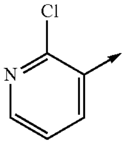

Q-2.60

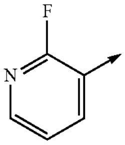

$R^3$ is hydrogen, $R^4$ is hydrogen, methyl, ethyl, n-propyl, i-propyl, n-butyl, n-pentyl, phenyl, benzyl, $CH_2$(4-Cl-Ph), $CH_2$(4-F-Ph), $CH_2$(4-MeO-Ph), 2-methoxyethyl, tetrahydrofuran-2-yl-methyl, tetrahydrofuran-3-ylmethyl, tetrahydropyran-2-ylmethyl, tetrahydropyran-3-ylmethyl, tetrahydropyran-4-ylmethyl, methylpropionate-3-yl, ethylpropionate-3-yl, methylacetate-2-yl, ethylacetate-2-yl, methyl-pivalate-2-yl, ethylpivalate-3-yl, methyl-2-methylpropanoate-3-yl, methyl-2,2-dimethyl-propanoate-3-yl, ethyl-2-methylpropanoate-3-yl, methyl-2-propanoate-2-yl, ethyl-2-propanoate-2-yl, methylacetate-2-yl, ethylacetate-2-yl, methyl-1-methylcyclopropanecarboxylate-2-yl, ethyl-1-methylcyclopropanecarboxylat-2-yl, 2-(dimethylamino)ethyl, oxetan-3-yl, (3-methyloxetan-3-yl)methyl, 2,2,2-trifluoroethyl, 2,2-difluoroethyl, 2-fluoroethyl, 2,2,3,3,3-pentafluoropropyl, cyclopropylmethyl, 1-cyclopropylethyl, (1-methylcyclopropyl)methyl, (2,2-dichlorocyclo-propyl)methyl, (2,2-dimethylcyclopropyl)methyl, allyl, propargyl (prop-2-yn-1-yl), 2-chloro-prop-2-en-1-yl, 3-phenylprop-2-yn-1-yl, 3,3-dichloroprop-2-en-1-yl, 3,3-dichloro-2-fluoroprop-2-en-1-yl, methylprop-2-yn-1-yl, 2-methylprop-2-en-1-yl, but-2-en-1-yl, but-3-en-1-yl, but-2-yn-1-yl, but-3-yn-1-yl, 4-chlorobut-2-yn-1-yl, 3-methylbut-2-en-1-yl, 3-methylbut-1-en-1-yl, 1-(2E)-1-methylbut-2-en-1-yl, (E)-pent-3-en-2-yl or (Z)-pent-3-en-2-yl, cyclobutylmethyl, cyclo-pentylmethyl, cyclohexylmethyl, heptan-2-yl, isobutyl, 1,3-dioxolan-2-ylmethyl or 1-ethyl-5-methyl-1H-pyrazole-4-methyl, n is 0, 1, 2 or 3.

The invention extremely especially preferably provides compounds of the general formula (I) in which $(R^1)_n$-phenyl is the groups Q-1.1 to Q-1.53

Q-1.1

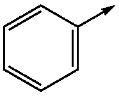

Q-1.2

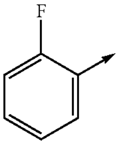

Q-1.3

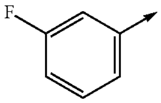

-continued
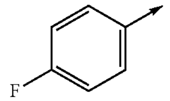
Q-1.4
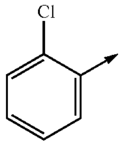
Q-1.5
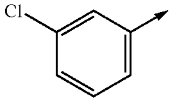
Q-1.6
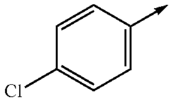
Q-1.7
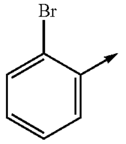
Q-1.8
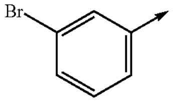
Q-1.9
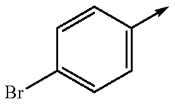
Q-1.10
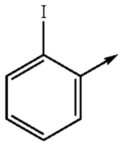
Q-1.11
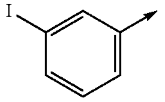
Q-1.12
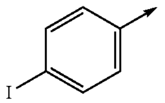
Q-1.13
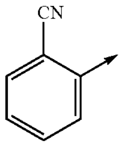
Q-1.14
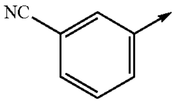
Q-1.15
-continued
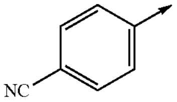
Q-1.16
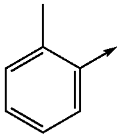
Q-1.17
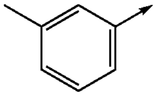
Q-1.18
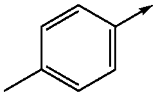
Q-1.19
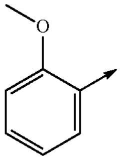
Q-1.20
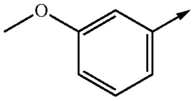
Q-1.21
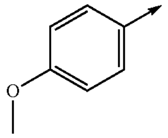
Q-1.22
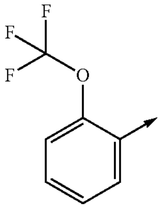
Q-1.23
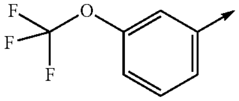
Q-1.24
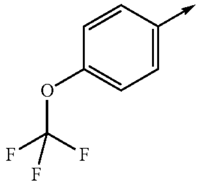
Q-1.25
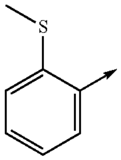
Q-1.26

-continued
Q-1.27
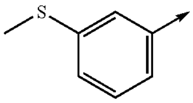
Q-1.28
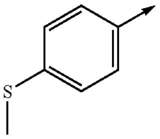
Q-1.29
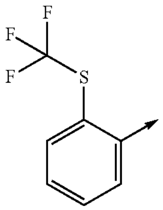
Q-1.30
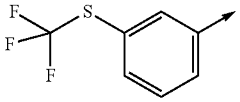
Q-1.31
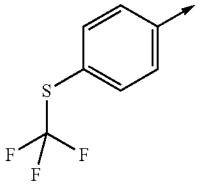
Q-1.32
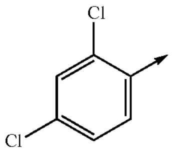
Q-1.33
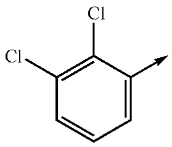
Q-1.34
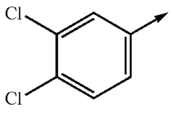
Q-1.35
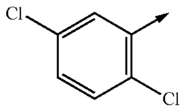
Q-1.36
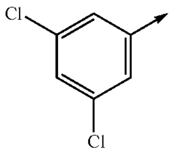
-continued
Q-1.37
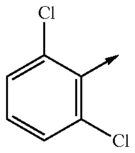
Q-1.38
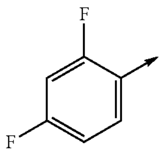
Q-1.39
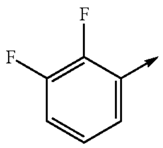
Q-1.40
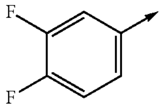
Q-1.41
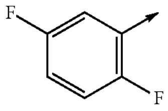
Q-1.42
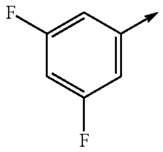
Q-1.43
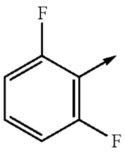
Q-1.44
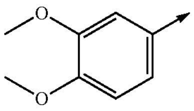
Q-1.45
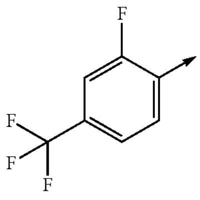
Q-1.46
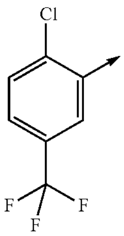

-continued
Q-1.47
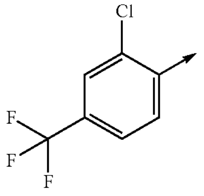
Q-1.48
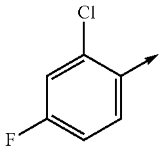
Q-1.49
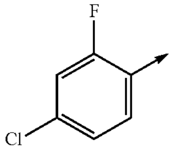
Q-1.50
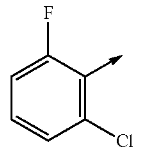
Q-1.51
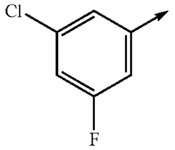
Q-1.52
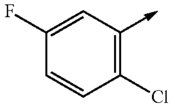
Q-1.53
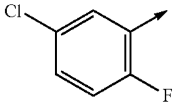
and
$R^2$ is the groups Q-2.1 to Q-2.60
Q-2.1
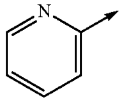
Q-2.2
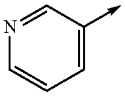
Q-2.3
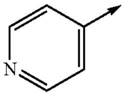
-continued
Q-2.4
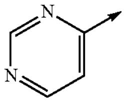
Q-2.5
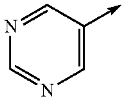
Q-2.6
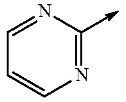
Q-2.7
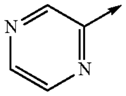
Q-2.8
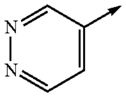
Q-2.9
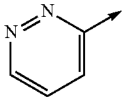
Q-2.10
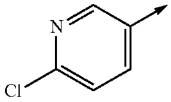
Q-2.11
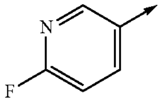
Q-2.12
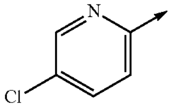
Q-2.13
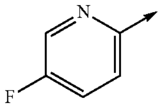
Q-2.14
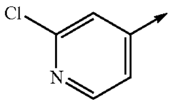
Q-2.15
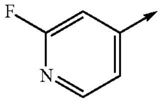
Q-2.16
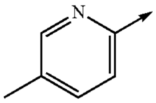

-continued
Q-2.17
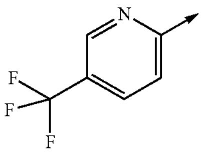
Q-2.18
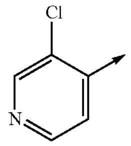
Q-2.19
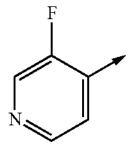
Q-2.20
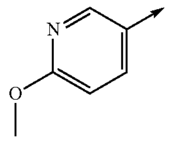
Q-2.21
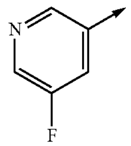
Q-2.22
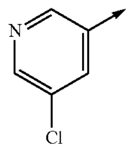
Q-2.23
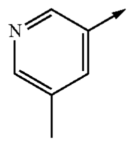
Q-2.24
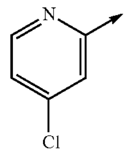
Q-2.25
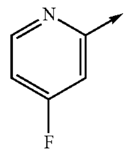
Q-2.26
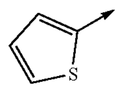
-continued
Q-2.27
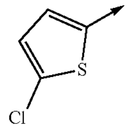
Q-2.28
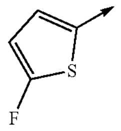
Q-2.29
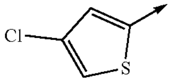
Q-2.30
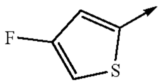
Q-2.31
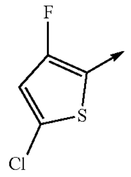
Q-2.32
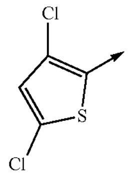
Q-2.33
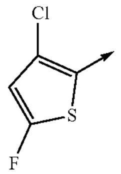
Q-2.34
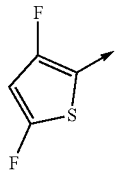
Q-2.35
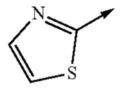
Q-2.36
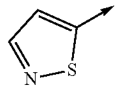
Q-2.37
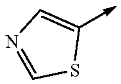
Q-2.38
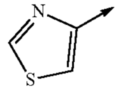

-continued

Q-2.39

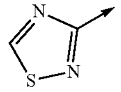

Q-2.40

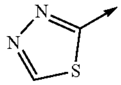

Q-2.41

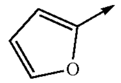

Q-2.42

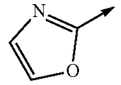

Q-2.43

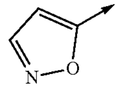

Q-2.44

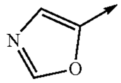

Q-2.45

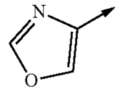

Q-2.46

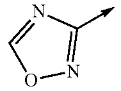

Q-2.47

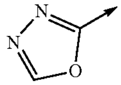

Q-2.48

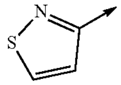

Q-2.49

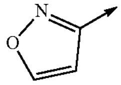

Q-2.50

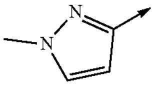

Q-2.51

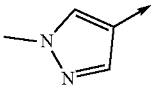

Q-2.52

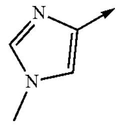

Q-2.53

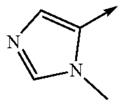

-continued

Q-2.54

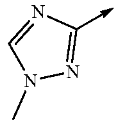

Q-2.55

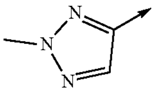

Q-2.56

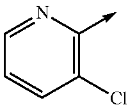

Q-2.57

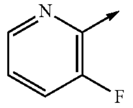

Q-2.58

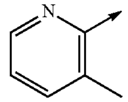

Q-2.59

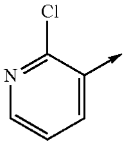

Q-2.60

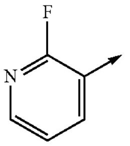

$R^3$ is hydrogen, and $R^4$ is hydrogen, methyl, ethyl, n-propyl, i-propyl, n-butyl, n-pentyl, phenyl, benzyl, $CH_2$(4-Cl-Ph), $CH_2$(4-F-Ph), $CH_2$(4-MeO-Ph), 2-methoxyethyl, tetrahydrofuran-2-yl-methyl, tetrahydrofuran-3-ylmethyl, tetrahydropyran-2-ylmethyl, tetrahydropyran-3-ylmethyl, tetrahydropyran-4-ylmethyl, methylpropionate-3-yl, ethylpropionate-3-yl, methylacetate-2-yl, ethylacetate-2-yl, methyl-pivalate-2-yl, ethylpivalate-3-yl, methyl-2-methylpropanoate-3-yl, methyl-2,2-dimethyl-propanoate-3-yl, ethyl-2-methylpropanoate-3-yl, methyl-2-propanoate-2-yl, ethyl-2-propanoate-2-yl, methylacet-2-yl, ethylacet-2-yl, methyl-1-methylcyclopropanecarboxylate-2-yl, ethyl-1-methylcyclopropanecarboxylat-2-yl, 2-(dimethylamino)ethyl, oxetan-3-yl, (3-methyloxetan-3-yl)methyl, 2,2,2-trifluoroethyl, 2,2-difluoroethyl, 2-fluoroethyl, 2,2,3,3,3-pentafluoropropyl, cyclopropylmethyl, 1-cyclopropylethyl, (1-methylcyclopropyl)methyl, (2,2-dichloro-cyclopropyl)methyl, (2,2-dimethylcyclopropyl)methyl, allyl, propargyl (prop-2-yn-1-yl), 2-chloroprop-2-en-1-yl, 3-phenylprop-2-yn-1-yl, 3,3-dichloroprop-2-en-1-yl, 3,3-dichloro-2-fluoroprop-2-en-1-yl, methylprop-2-yn-1-yl, 2-methylprop-2-en-1-yl, but-2-en-1-yl, but-3-en-1-yl, but-2-yn-1-yl, but-3-yn-1-yl, 4-chlorobut-2-yn-1-yl, 3-methylbut-2-en-1-yl, 3-methylbut-1-en-1-yl, 1-(2E)-1-methylbut-2-en-1-yl, (E)-pent-3-en-2-yl or (Z)-pent-3-en-2-yl, cyclo-butylmethyl, cyclopentylmethyl, cyclohexylmethyl, heptan-2-yl, isobutyl, 1,3-dioxolan-2-ylmethyl or 1-ethyl-5-methyl-1H-pyrazole-4-methyl.
The invention particularly extremely especially preferably provides compounds of the general formula (I) in which $(R^1)_n$-phenyl is the groups Q-1.1 to Q-1.53
Q-1.1
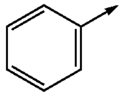
Q-1.2
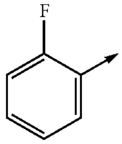
Q-1.3
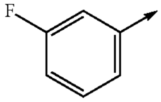
Q-1.4
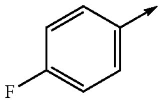
Q-1.5
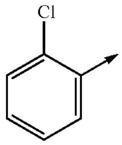
Q-1.6
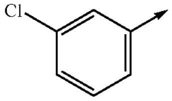
Q-1.7
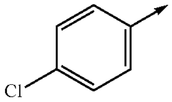
Q-1.8
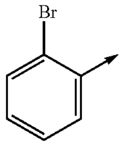
Q-1.9
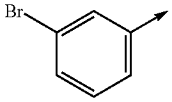
Q-1.10
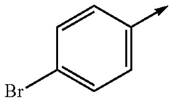
Q-1.11
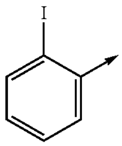
-continued
Q-1.12
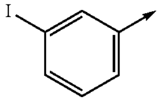
Q-1.13
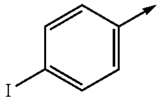
Q-1.14
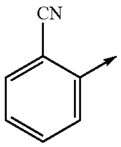
Q-1.15
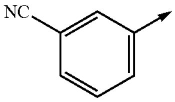
Q-1.16
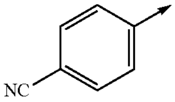
Q-1.17
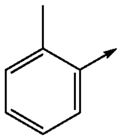
Q-1.18
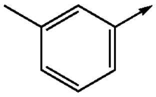
Q-1.19
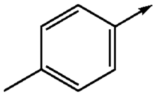
Q-1.20
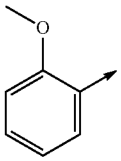
Q-1.21
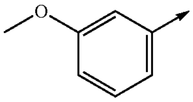
Q-1.22
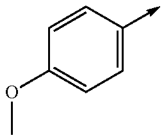

-continued
Q-1.23
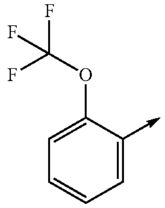
Q-1.24
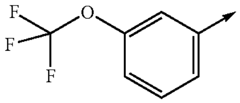
Q-1.25
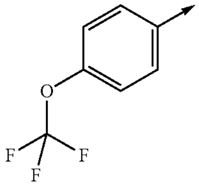
Q-1.26
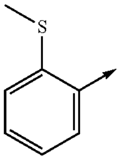
Q-1.27
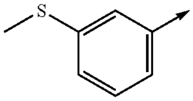
Q-1.28
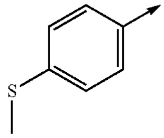
Q-1.29
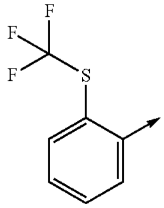
Q-1.30
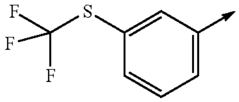
Q-1.31
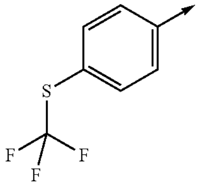
-continued
Q-1.32
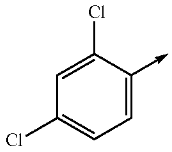
Q-1.33
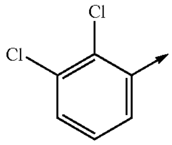
Q-1.34
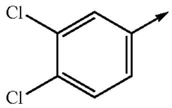
Q-1.35
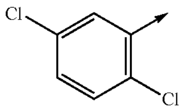
Q-1.36
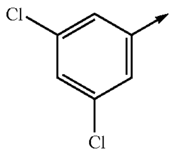
Q-1.37
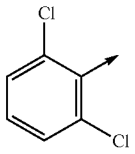
Q-1.38
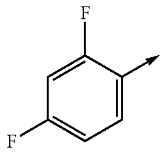
Q-1.39
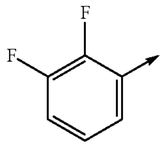
Q-1.40
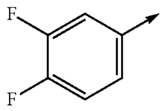
Q-1.41
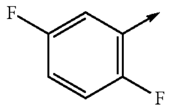
Q-1.42
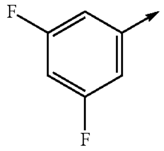

-continued
Q-1.43
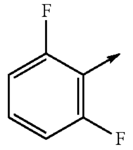
Q-1.44
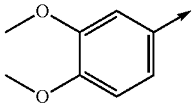
Q-1.45
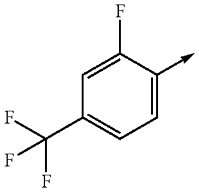
Q-1.46
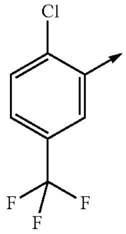
Q-1.47
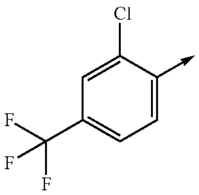
Q-1.48
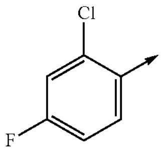
Q-1.49
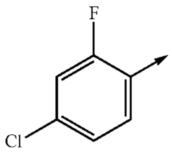
Q-1.50
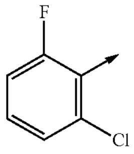
Q-1.51
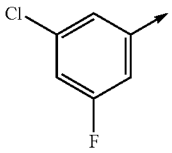
-continued
Q-1.52
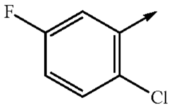
Q-1.53
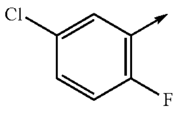
and
$R^2$ is the groups Q-2.1 to Q-2.60
Q-2.1
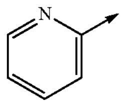
Q-2.2
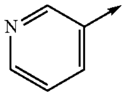
Q-2.3
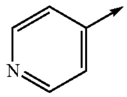
Q-2.4
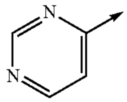
Q-2.5
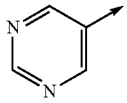
Q-2.6
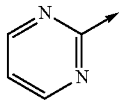
Q-2.7
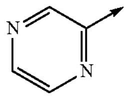
Q-2.10
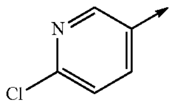
Q-2.11
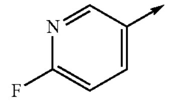
Q-2.12
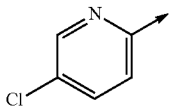

-continued

Q-2.13

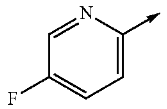

Q-2.14

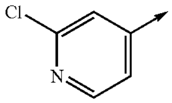

Q-2.15

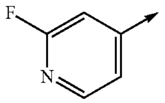

Q-2.17

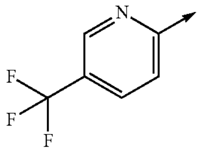

Q-2.18

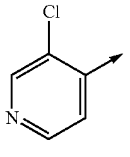

Q-2.19

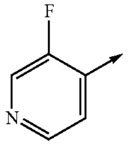

Q-2.21

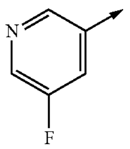

Q-2.22

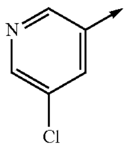

Q-2.24

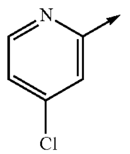

Q-2.25

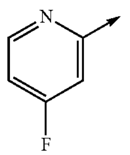

Q-2.56

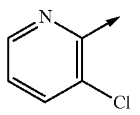

-continued

Q-2.57

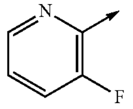

Q-2.59

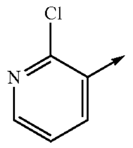

Q-2.60

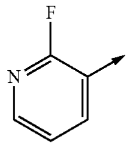

$R^3$ is hydrogen, and $R^4$ is hydrogen, methyl, ethyl, n-propyl, i-propyl, n-butyl, n-pentyl, phenyl, benzyl, $CH_2$(4-Cl-Ph), $CH_2$(4-F-Ph), $CH_2$(4-MeO-Ph), 2-methoxyethyl, tetrahydrofuran-2-yl-methyl, tetrahydrofuran-3-ylmethyl, tetrahydropyran-2-ylmethyl, tetrahydropyran-3-ylmethyl, tetrahydropyran-4-ylmethyl, methylpropionate-3-yl, ethylpropionate-3-yl, methylacetate-2-yl, ethylacetate-2-yl, methyl-pivalate-2-yl, ethylpivalate-3-yl, methyl-2-methylpropanoate-3-yl, methyl-2,2-dimethylpropanoate-3-yl, ethyl-2-methylpropanoate-3-yl, methyl-2-propanoate-2-yl, ethyl-2-propanoate-2-yl, methylacet-2-yl, ethylacet-2-yl, methyl-1-methylcyclopropanecarboxylate-2-yl, ethyl-1-methylcyclopropanecarboxylat-2-yl, 2-(dimethylamino)ethyl, oxetan-3-yl, (3-methyloxetan-3-yl)methyl, 2,2,2-trifluoroethyl, 2,2-difluoroethyl, 2-fluoroethyl, 2,2,3,3,3-penta-fluoropropyl, cyclopropylmethyl, 1-cyclopropylethyl, (1-methylcyclopropyl)methyl, (2,2-dichlorocyclopropyl)methyl, (2,2-dimethylcyclopropyl)methyl, allyl, propargyl (prop-2-yn-1-yl), 2-chloroprop-2-en-1-yl, 3-phenylprop-2-yn-1-yl, 3,3-dichloroprop-2-en-1-yl, 3,3-dichloro-2-fluoroprop-2-en-1-yl, methylprop-2-yn-1-yl, 2-methylprop-2-en-1-yl, but-2-en-1-yl, but-3-en-1-yl, but-2-yn-1-yl, but-3-yn-1-yl, 4-chlorobut-2-yn-1-yl, 3-methylbut-2-en-1-yl, 3-methylbut-1-en-1-yl, 1-(2E)-1-methylbut-2-en-1-yl, (E)-pent-3-en-2-yl or (Z)-pent-3-en-2-yl, cyclobutyl-methyl, cyclopentylmethyl, cyclohexylmethyl, heptan-2-yl, isobutyl, 1,3-dioxolan-2-ylmethyl or 1-ethyl-5-methyl-1H-pyrazole-4-methyl.

The abovementioned general or preferred radical definitions apply both to the end products of the general formula (I) and, correspondingly, to the starting materials or the intermediates required in each case for the preparation. These radical definitions can be combined with one another as desired, i.e. including combinations between the given preferred ranges.

Of particular interest, primarily for reasons of higher herbicidal activity, better selectivity and/or better preparability, are inventive compounds of the general formula (I) given or salts thereof or the inventive use thereof in which individual radicals have one of the preferred meanings already specified or specified below, or in particular those in which one or more of the preferred meanings already specified or specified below occur in combination.

With regard to the compounds of the invention, the terms used above and further down will be elucidated. These are familiar to the person skilled in the art and especially have the definitions elucidated hereinafter:

Unless defined differently, names of chemical groups are generally to be understood such that attachment to the skeleton or the remainder of the molecule is via the structural element of the relevant chemical group mentioned last, i.e. for example in the case of ($C_2$-$C_{18}$)-alkenyloxy via the oxygen atom and in the case of heterocyclyl-($C_1$-$C_{18}$)-alkyl or MeO(O)C—($C_1$-$C_{18}$)-alkyl in each case via the carbon atom of the alkyl group.

According to the invention, "alkylsulfonyl"—alone or as part of a chemical group—refers to straight-chain or branched alkylsulfonyl, preferably having 1 to 8 or 1 to 6 carbon atoms, for example (but not limited to) ($C_1$-$C_6$)-alkylsulfonyl such as methylsulfonyl, ethylsulfonyl, propylsulfonyl, 1-methylethylsulfonyl, butylsulfonyl, 1-methylpropylsulfonyl, 2-methylpropylsulfonyl, 1,1-dimethylethylsulfonyl, pentyl-sulfonyl, 1-methylbutylsulfonyl, 2-methylbutylsulfonyl, 3-methylbutylsulfonyl, 1,1-dimethylpropyl-sulfonyl, 1,2-dimethylpropylsulfonyl, 2,2-dimethylpropylsulfonyl, 1-ethylpropylsulfonyl, hexylsulfonyl, 1-methylpentylsulfonyl, 2-methylpentylsulfonyl, 3-methylpentylsulfonyl, 4-methylpentylsulfonyl, 1,1-dimethylbutylsulfonyl, 1,2-dimethylbutylsulfonyl, 1,3-dimethylbutylsulfonyl, 2,2-dimethylbutylsulfonyl, 2,3-dimethylbutylsulfonyl, 3,3-dimethylbutylsulfonyl, 1-ethylbutylsulfonyl, 2-ethylbutylsulfonyl, 1,1,2-trimethylpropylsulfonyl, 1,2,2-trimethylpropylsulfonyl, 1-ethyl-1-methylpropylsulfonyl and 1-ethyl-2-methylpropylsulfonyl.

According to the invention, "alkylthio"—alone or as part of a chemical group—refers to straight-chain or branched S-alkyl, preferably having 1 to 8 or 1 to 6 carbon atoms, such as ($C_1$-$C_{10}$)—, ($C_1$-$C_6$)- or ($C_1$-$C_4$)-alkylthio, for example (but not limited to) ($C_1$-$C_6$)-alkylthio such as methylthio, ethylthio, propylthio, 1-methylethylthio, butylthio, 1-methylpropylthio, 2-methylpropylthio, 1,1-dimethylethylthio, pentylthio, 1-methylbutylthio, 2-methylbutylthio, 3-methylbutylthio, 1,1-dimethylpropylthio, 1,2-dimethylpropylthio, 2,2-dimethylpropylthio, 1-ethylpropylthio, hexylthio, 1-methylpentylthio, 2-methylpentylthio, 3-methylpentylthio, 4-methylpentylthio, 1,1-dimethylbutylthio, 1,2-dimethylbutylthio, 1,3-dimethyl-butylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio and 1-ethyl-2-methylpropylthio.

According to the invention, "alkylsulfinyl (alkyl-S(═O)—)", unless defined differently elsewhere, denotes alkyl radicals which are bonded to the skeleton via —S(═O)—, such as ($C_1$-$C_{10}$)—, ($C_1$-$C_6$)- or ($C_1$-$C_4$)-alkylsulfinyl, for example (but not limited to) ($C_1$-$C_6$)-alkylsulfinyl such as methylsulfinyl, ethylsulfinyl, propylsulfinyl, 1-methylethylsulfinyl, butylsulfinyl, 1-methylpropylsulfinyl, 2-methylpropylsulfinyl, 1,1-dimethylethylsulfinyl, pentylsulfinyl, 1-methylbutylsulfinyl, 2-methylbutylsulfinyl, 3-methylbutyl-sulfinyl, 1,1-dimethylpropylsulfinyl, 1,2-dimethylpropylsulfinyl, 2,2-dimethylpropylsulfinyl, 1-ethyl-propylsulfinyl, hexylsulfinyl, 1-methylpentylsulfinyl, 2-methylpentylsulfinyl, 3-methylpentylsulfinyl, 4-methylpentylsulfinyl, 1,1-dimethylbutylsulfinyl, 1,2-dimethylbutylsulfinyl, 1,3-dimethylbutylsulfinyl, 2,2-dimethylbutylsulfinyl, 2,3-dimethylbutylsulfinyl, 3,3-dimethylbutylsulfinyl, 1-ethylbutylsulfinyl, 2-ethyl-butylsulfinyl, 1,1,2-trimethylpropylsulfinyl, 1,2,2-trimethylpropylsulfinyl, 1-ethyl-1-methylpropyl-sulfinyl and 1-ethyl-2-methylpropylsulfinyl.

"Alkoxy" denotes an alkyl radical attached via an oxygen atom, for example (but not limited to) ($C_1$-$C_6$)-alkoxy such as methoxy, ethoxy, propoxy, 1-methylethoxy, butoxy, 1-methylpropoxy, 2-methylpropoxy, 1,1-dimethylethoxy, pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy. Alkenyloxy denotes an alkenyl radical attached via an oxygen atom, and alkynyloxy denotes an alkynyl radical attached via an oxygen atom, such as ($C_2$-$C_{10}$-, ($C_2$-$C_6$)- or ($C_2$-$C_4$)-alkeneoxy and ($C_3$-$C_{10}$)—, ($C_3$-$C_6$)- or ($C_3$-$C_4$)-alkyneoxy.

According to the invention, "alkylcarbonyl" (alkyl-C(═O)—), unless defined differently elsewhere, represents alkyl radicals bonded to the skeleton via —C(═O)—, such as ($C_1$-$C_{10}$)-, ($C_1$-$C_6$)- or ($C_1$-$C_4$)-alkylcarbonyl. The number of the carbon atoms here relates to the alkyl radical in the alkylcarbonyl group.

"Alkoxycarbonyl (alkyl-O—C(═O)—)", unless defined differently elsewhere: alkyl radicals bonded to the skeleton via —O—C(═O)—, such as ($C_1$-$C_{10}$)—, ($C_1$-$C_6$)- or ($C_1$-$C_4$)-alkoxycarbonyl. The number of the carbon atoms here relates to the alkyl radical in the alkoxycarbonyl group. Analogously, "alkenyloxycarbonyl" and "alkynyloxycarbonyl", unless defined differently elsewhere, in accordance with the invention, respectively represent alkenyl and alkynyl radicals bonded to the skeleton via —O—C(═O)—, such as ($C_2$-$C_6$)- or ($C_2$-$C_4$)-alkenyloxycarbonyl and ($C_3$-$C_{10}$)—, ($C_3$-$C_6$)- or ($C_3$-$C_4$)-alkynyloxycarbonyl. The number of the carbon atoms here refers to the alkenyl or alkynyl radical in the alkenyloxycarbonyl or alkynyloxycarbonyl group.

According to the invention, the term "alkylcarbonyloxy" (alkyl-C(═O)—O—), unless defined differently elsewhere, represents alkyl radicals bonded to the skeleton via the oxygen of a carbonyloxy group (—C(═O)—O—), such as ($C_1$-$C_{10}$)—, ($C_1$-$C_6$)- or ($C_1$-$C_4$)-alkylcarbonyloxy. The number of the carbon atoms here relates to the alkyl radical in the alkylcarbonyloxy group.

The term "aryl" denotes an optionally substituted mono-, bi- or polycyclic aromatic system having preferably 6 to 14, especially 6 to 10, ring carbon atoms, for example phenyl, naphthyl, anthryl, phenanthrenyl and the like, preferably phenyl.

The term "optionally substituted aryl" also includes polycyclic systems, such as tetrahydronaphthyl, indenyl, indanyl, fluorenyl, biphenylyl, where the bonding site is on the aromatic system. In systematic terms, "aryl" is generally also encompassed by the term "optionally substituted phenyl". Preferred aryl substituents here are, for example, hydrogen, halogen, alkyl, cycloalkyl, cycloalkylalkyl, cycloalkenyl, halocycloalkyl, alkenyl, alkynyl, aryl, arylalkyl, heteroaryl, heteroarylalkyl, heterocyclyl, heterocyclylalkyl, alkoxyalkyl, alkylthio, haloalkylthio, haloalkyl, alkoxy, haloalkoxy, cycloalkoxy, cycloalkylalkoxy, aryloxy, heteroraryloxy, alkoxyalkoxy, alkynylalkoxy, alkenyloxy, bisalkylaminoalkoxy, tris [alkyl]silyl, bis [alkyl]arylsilyl, bis [alkyl]alkylsilyl, tris [alkyl]silyl alkynyl, alkylalkynyl, cycloalkylalkynyl, haloalkylalkynyl, heterocyclyl-N-alkoxy, nitro, cyano, amino, alkylamino, bisalkylamino, alkylcarbonylamino, cycloalkylcarbonylamino, arylcarbonylamino, alkoxycarbonylamino, alkoxycarbonylalkylamino, arylalkoxycarbonylalkylamino, hydroxycarbonyl, alkoxycarbonyl, aminocarbonyl, alkylaminocarbonyl, cycloalkylaminocarbonyl, bisalkylaminocarbonyl, heteroarylalkoxy, arylalkoxy.

A heterocyclic radical (heterocyclyl) contains at least one heterocyclic ring (=carbocyclic ring in which at least one carbon atom has been replaced by a heteroatom, preferably by a heteroatom from the group of N, O, S, P) which is saturated, unsaturated, partly saturated or heteroaromatic and may be unsubstituted or substituted, in which case the bonding site is localized on a ring atom. If the heterocyclyl radical or the heterocyclic ring is optionally substituted, it may be fused to other carbocyclic or heterocyclic rings. In the case of optionally substituted heterocyclyl, polycyclic systems are also included, for example 8-azabicyclo[3.2.1]octanyl, 8-azabicyclo[2.2.2]octanyl or 1-azabicyclo[2.2.1]heptyl. Optionally substituted heterocyclyl also includes spirocyclic systems, for example 1-oxa-5-azaspiro[2.3]hexyl. Unless defined differently, the heterocyclic ring preferably contains 3 to 9 ring atoms, especially 3 to 6 ring atoms, and one or more, preferably 1 to 4, especially 1, 2 or 3, heteroatoms in the heterocyclic ring, preferably from the group of N, O and S, but no two oxygen atoms should be directly adjacent, for example with one heteroatom from the group of N, O and S: 1- or 2- or 3-pyrrolidinyl, 3,4-dihydro-2H-pyrrol-2- or -3-yl, 2,3-dihydro-1H-pyrrol-1- or -2- or -3- or -4- or -5-yl; 2,5-dihydro-1H-pyrrol-1- or -2- or -3-yl, 1- or 2- or 3- or 4-piperidinyl; 2,3,4,5-tetrahydropyridin-2- or -3- or -4- or -5-yl or -6-yl; 1,2,3,6-tetrahydropyridin-1- or -2- or -3- or -4- or -5- or -6-yl; 1,2,3,4-tetrahydropyridin-1- or -2- or -3- or -4- or -5- or -6-yl; 1,4-dihydropyridin-1- or -2- or -3- or -4-yl; 2,3-dihydropyridin-2- or -3- or -4- or -5- or -6-yl; 2,5-dihydropyridin-2- or -3- or -4- or -5- or -6-yl, 1- or 2- or 3- or 4-azepanyl; 2,3,4,5-tetrahydro-1H-azepin-1- or -2- or -3- or -4- or -5- or -6- or -7-yl; 2,3,4,7-tetrahydro-1H-azepin-1- or -2- or -3- or -4- or -5- or -6- or -7-yl; 2,3,6,7-tetrahydro-1H-azepin-1- or -2- or -3- or -4-yl; 3,4,5,6-tetrahydro-2H-azepin-2- or -3- or -4- or -5- or -6- or -7-yl; 4,5-dihydro-1H-azepin-1- or -2- or -3- or -4-yl; 2,5-dihydro-1H-azepin-1- or -2- or -3- or -4- or -5- or -6- or -7-yl; 2,7-dihydro-1H-azepin-1- or -2- or -3- or -4-yl; 2,3-dihydro-1H-azepin-1- or -2- or -3- or -4- or -5- or -6- or -7-yl; 3,4-dihydro-2H-azepin-2- or -3- or -4- or -5- or -6- or -7-yl; 3,6-dihydro-2H-azepin-2- or -3- or -4- or -5- or -6- or -7-yl; 5,6-dihydro-2H-azepin-2- or -3- or -4- or -5- or -6- or -7-yl; 4,5-dihydro-3H-azepin-2- or -3- or -4- or -5- or -6- or -7-yl; 1H-azepin-1- or -2- or -3- or -4- or -5- or -6- or -7-yl; 2H-azepin-2- or -3- or -4- or -5- or -6- or -7-yl; 3H-azepin-2- or -3- or -4- or -5- or -6- or -7-yl; 4H-azepin-2- or -3- or -4- or -5- or -6- or -7-yl, 2- or 3-oxolanyl (=2- or 3-tetrahydrofuranyl); 2,3-dihydrofuran-2- or -3- or -4- or -5-yl; 2,5-dihydrofuran-2- or -3-yl, 2- or 3- or 4-oxanyl (=2- or 3- or 4-tetrahydropyranyl); 3,4-dihydro-2H-pyran-2- or -3- or -4- or -5- or -6-yl; 3,6-dihydro-2H-pyran-2- or -3- or -4- or -5- or -6-yl; 2H-pyran-2- or -3- or -4- or -5- or -6-yl; 4H-pyran-2- or -3- or -4-yl, 2- or 3- or 4-oxepanyl; 2,3,4,5-tetrahydrooxepin-2- or -3- or -4- or -5- or -6- or -7-yl; 2,3,4,7-tetrahydrooxepin-2- or -3- or -4- or -5- or -6- or -7-yl; 2,3,6,7-tetrahydrooxepin-2- or -3- or -4-yl; 2,3-dihydrooxepin-2- or -3- or -4- or -5- or -6- or -7-yl; 4,5-dihydrooxepin-2- or -3- or -4-yl; 2,5-dihydrooxepin-2- or -3- or -4- or -5- or -6- or -7-yl; oxepin-2- or -3- or -4- or -5- or -6- or -7-yl; 2- or 3-tetrahydrothiophenyl; 2,3-dihydrothiophen-2- or -3- or -4- or -5-yl; 2,5-dihydrothiophen-2- or -3-yl; tetrahydro-2H-thiopyran-2- or -3- or -4-yl; 3,4-dihydro-2H-thiopyran-2- or -3- or -4- or -5- or -6-yl; 3,6-dihydro-2H-thiopyran-2- or -3- or -4- or -5- or -6-yl; 2H-thiopyran-2- or -3- or -4- or -5- or -6-yl; 4H-thiopyran-2- or -3- or -4-yl. Preferred 3-membered and 4-membered heterocycles are, for example, 1- or 2-aziridinyl, oxiranyl, thiiranyl, 1- or 2- or 3-azetidinyl, 2- or 3-oxetanyl, 2- or 3-thietanyl, 1,3-dioxetan-2-yl. Further examples of "heterocyclyl" are a partly or fully hydrogenated heterocyclic radical having two heteroatoms from the group of N, O and S, for example 1- or 2- or 3- or 4-pyrazolidinyl; 4,5-dihydro-3H-pyrazol-3- or 4- or 5-yl; 4,5-dihydro-1H-pyrazol-1- or 3- or 4- or 5-yl; 2,3-dihydro-1H-pyrazol-1- or 2- or 3- or 4- or 5-yl; 1- or 2- or 3- or 4-imidazolidinyl; 2,3-dihydro-1H-imidazol-1- or 2- or 3- or 4-yl; 2,5-dihydro-1H-imidazol-1- or 2- or 4- or 5-yl; 4,5-dihydro-1H-imidazol-1- or 2- or 4- or 5-yl; hexahydropyridazin-1- or 2- or 3- or 4-yl; 1,2,3,4-tetrahydropyridazin-1- or 2- or 3- or 4- or 5- or 6-yl; 1,2,3,6-tetrahydropyridazin-1- or 2- or 3- or 4- or 5- or 6-yl; 1,4,5,6-tetrahydropyridazin-1- or 3- or 4- or 5- or 6-yl; 3,4,5,6-tetrahydropyridazin-3- or 4- or 5-yl; 4,5-dihydropyridazin-3- or 4-yl; 3,4-dihydropyridazin-3- or 4- or 5- or 6-yl; 3,6-dihydropyridazin-3- or 4-yl; 1,6-dihydropyriazin-1- or 3- or 4- or 5- or 6-yl; hexahydropyrimidin-1- or 2- or 3- or 4-yl; 1,4,5,6-tetrahydropyrimidin-1- or 2- or 4- or 5- or 6-yl; 1,2,5,6-tetrahydropyrimidin-1- or 2- or 4- or 5- or 6-yl; 1,2,3,4-tetrahydropyrimidin-1- or 2- or 3- or 4- or 5- or 6-yl; 1,6-dihydropyrimidin-1- or 2- or 4- or 5- or 6-yl; 1,2-dihydropyrimidin-1- or 2- or 4- or 5- or 6-yl; 2,5-dihydropyrimidin-2- or 4- or 5-yl; 4,5-dihydropyrimidin-4- or 5- or 6-yl; 1,4-dihydropyrimidin-1- or 2- or 4- or 5- or 6-yl; 1- or 2- or 3-piperazinyl; 1,2,3,6-tetrahydropyrazin-1- or 2- or 3- or 5- or 6-yl; 1,2,3,4-tetrahydropyrazin-1- or 2- or 3- or 4- or 5- or 6-yl; 1,2-dihydropyrazin-1- or 2- or 3- or 5- or 6-yl; 1,4-dihydropyrazin-1- or 2- or 3-yl; 2,3-dihydropyrazin-2- or 3- or 5- or 6-yl; 2,5-dihydropyrazin-2- or 3-yl; 1,3-dioxolan-2- or 4- or 5-yl; 1,3-dioxol-2- or 4-yl; 1,3-dioxan-2- or 4- or 5-yl; 4H-1,3-dioxin-2- or 4- or 5- or 6-yl; 1,4-dioxan-2- or 3- or 5- or 6-yl; 2,3-dihydro-1,4-dioxin-2- or 3- or 5- or 6-yl; 1,4-dioxin-2- or 3-yl; 1,2-dithiolan-3- or 4-yl; 3H-1,2-dithiol-3- or 4- or 5-yl; 1,3-dithiolan-2- or 4-yl; 1,3-dithiol-2- or 4-yl; 1,2-dithian-3- or 4-yl; 3,4-dihydro-1,2-dithiin-3- or 4- or 5- or 6-yl; 3,6-dihydro-1,2-dithiin-3- or 4-yl; 1,2-dithiin-3- or 4-yl; 1,3-dithian-2- or 4- or 5-yl; 4H-1,3-dithiin-2- or 4- or 5- or 6-yl; isoxazolidin-2- or 3- or 4- or 5-yl; 2,3-dihydroisoxazol-2- or 3- or 4- or 5-yl; 2,5-dihydroisoxazol-2- or 3- or 4- or 5-yl; 4,5-dihydroisoxazol-3- or 4- or 5-yl; 1,3-oxazolidin-2- or 3- or 4- or 5-yl; 2,3-dihydro-1,3-oxazol-2- or 3- or 4- or 5-yl; 2,5-dihydro-1,3-oxazol-2- or 4- or 5-yl; 4,5-dihydro-1,3-oxazol-2- or 4- or 5-yl; 1,2-oxazinan-2- or 3- or 4- or 5- or 6-yl; 3,4-dihydro-2H-1,2-oxazin-2- or 3- or 4- or 5- or 6-yl; 3,6-dihydro-2H-1,2-oxazin-2- or 3- or 4- or 5- or 6-yl; 5,6-dihydro-2H-1,2-oxazin-2- or 3- or 4- or 5- or 6-yl; 5,6-dihydro-4H-1,2-oxazin-3- or 4- or 5- or 6-yl; 2H-1,2-oxazin-2- or 3- or 4- or 5- or 6-yl; 6H-1,2-oxazin-3- or 4- or 5- or 6-yl; 4H-1,2-oxazin-3- or 4- or 5- or 6-yl; 1,3-oxazinan-2- or 3- or 4- or 5- or 6-yl; 3,4-dihydro-2H-1,3-oxazin-2- or 3- or 4- or 5- or 6-yl; 3,6-dihydro-2H-1,3-oxazin-2- or 3- or 4- or 5- or 6-yl; 5,6-dihydro-2H-1,3-oxazin-2- or 4- or 5- or 6-yl; 5,6-dihydro-4H-1,3-oxazin-2- or 4- or 5- or 6-yl; 2H-1,3-oxazin-2- or 4- or 5- or 6-yl; 6H-1,3-oxazin-2- or 4- or 5- or 6-yl; 4H-1,3-oxazin-2- or 4- or 5- or 6-yl; morpholin-2- or 3- or 4-yl; 3,4-dihydro-2H-1,4-oxazin-2- or 3- or 4- or 5- or 6-yl; 3,6-dihydro-2H-1,4-oxazin-2- or 3- or 5- or 6-yl; 2H-1,4-oxazin-2- or 3- or 5- or 6-yl; 4H-1,4-oxazin-2- or 3-yl; 1,2-oxazepan-2- or 3- or 4- or 5- or 6- or 7-yl; 2,3,4,5-tetrahydro-1,2-oxazepin-2- or 3- or 4- or 5- or 6- or 7-yl; 2,3,4,7-tetrahydro-1,2-oxazepin-2- or 3- or 4- or 5- or 6- or 7-yl; 2,3,6,7-tetrahydro-1,2-oxazepin-2- or 3- or 4- or 5- or 6- or 7-yl; 2,5,6,7-tetrahydro-1,2-oxazepin-2- or 3- or 4- or 5- or 6- or 7-yl; 4,5,6,7-tetrahydro-1,2-oxazepin-3- or 4- or 5- or 6- or 7-yl; 2,3-dihydro-1,2-oxazepin-2- or 3- or 4- or or 6- or 7-yl; 2,5-dihydro-1,2-oxazepin-2- or 3- or 4- or 5- or 6- or 7-yl; 2,7-dihydro-1,2-oxazepin-2- or 3- or 4- or 5- or 6- or 7-yl; 4,5-dihydro-1,2-oxazepin-3- or 4- or 5- or 6- or 7-yl; 4,7-dihydro-1,2-oxazepin-3- or 4- or 5- or 6- or 7-yl; 6,7-dihydro-1,2-oxazepin-3- or 4- or 5- or 6- or 7-yl; 1,2-oxazepin-3- or 4- or 5- or 6- or 7-yl; 1,3-oxazepan-2- or 3- or 4- or 5- or 6- or 7-yl; 2,3,4,5-tetrahydro-1,3-oxazepin-2- or 3- or 4- or 5- or 6- or 7-yl; 2,3,4,7-tetrahydro-1,3-oxazepin-2- or 3- or 4- or 5- or 6- or 7-yl; 2,3,6,7-tetrahydro-1,3-oxazepin-2- or 3- or 4- or 5- or 6- or 7-yl; 2,5,6,7-tetrahydro-1,3-oxazepin-2- or 4- or 5- or 6- or 7-yl; 4,5,6,7-tetrahydro-1,3-oxazepin-2- or 4- or 5- or 6- or 7-yl; 2,3-dihydro-1,3-oxazepin-2- or 3- or 4- or 5- or 6- or 7-yl; 2,5-dihydro-1,3-oxazepin-2- or 4- or 5- or 6- or 7-yl; 2,7-dihydro-1,3-oxazepin-2- or 4- or 5- or 6- or 7-yl; 4,5-dihydro-1,3-oxazepin-2- or 4- or 5- or 6- or 7-yl; 4,7-dihydro-1,3-oxazepin-2- or 4- or 5- or 6- or 7-yl; 6,7-dihydro-1,3-oxazepin-2- or 4- or 5- or 6- or 7-yl; 1,3-oxazepin-2- or 4- or or 6- or 7-yl; 1,4-oxazepan-2- or 3- or 5- or 6- or 7-yl; 2,3,4,5-tetrahydro-1,4-oxazepin-2- or 3- or 4- or or 6- or 7-yl; 2,3,4,7-tetrahydro-1,4-oxazepin-2- or 3- or 4- or 5- or 6- or 7-yl; 2,3,6,7-tetrahydro-1,4-oxazepin-2- or 3- or 5- or 6- or 7-yl; 2,5,6,7-tetrahydro-1,4-oxazepin-2- or 3- or 5- or 6- or 7-yl; 4,5,6,7-tetrahydro-1,4-oxazepin-2- or 3- or 4- or 5- or 6- or 7-yl; 2,3-dihydro-1,4-oxazepin-2- or 3- or 5- or 6- or 7-yl; 2,5-dihydro-1,4-oxazepin-2- or 3- or 5- or 6- or 7-yl; 2,7-dihydro-1,4-oxazepin-2- or 3- or 5- or 6- or 7-yl; 4,5-dihydro-1,4-oxazepin-2- or 3- or 4- or 5- or 6- or 7-yl; 4,7-dihydro-1,4-oxazepin-2- or 3- or 4- or 5- or 6- or 7-yl; 6,7-dihydro-1,4-oxazepin-2- or 3- or 5- or 6- or 7-yl; 1,4-oxazepin-2- or 3- or 5- or 6- or 7-yl; isothiazolidin-2- or 3- or 4- or 5-yl; 2,3-dihydroisothiazol-2- or 3- or 4- or 5-yl; 2,5-dihydroisothiazol-2- or 3- or 4- or 5-yl; 4,5-dihydroisothiazol-3- or 4- or 5-yl; 1,3-thiazolidin-2- or 3- or 4- or 5-yl; 2,3-dihydro-1,3-thiazol-2- or 3- or 4- or 5-yl; 2,5-dihydro-1,3-thiazol-2- or 4- or 5-yl; 4,5-dihydro-1,3-thiazol-2- or 4- or 5-yl; 1,3-thiazinan-2- or 3- or 4- or 5- or 6-yl; 3,4-dihydro-2H-1,3-thiazin-2- or 3- or 4- or 5- or 6-yl; 3,6-dihydro-2H-1,3-thiazin-2- or 3- or 4- or 5- or 6-yl; 5,6-dihydro-2H-1,3-thiazin-2- or 4- or 5- or 6-yl; 5,6-dihydro-4H-1,3-thiazin-2- or 4- or 5- or 6-yl; 2H-1,3-thiazin-2- or 4- or or 6-yl; 6H-1,3-thiazin-2- or 4- or 5- or 6-yl; 4H-1,3-thiazin-2- or 4- or 5- or 6-yl. Further examples of "heterocyclyl" are a partly or fully hydrogenated heterocyclic radical having 3 heteroatoms from the group of N, O and S, for example 1,4,2-dioxazolidin-2- or 3- or 5-yl; 1,4,2-dioxazol-3- or 5-yl; 1,4,2-dioxazinan-2- or -3- or 5- or 6-yl; 5,6-dihydro-1,4,2-dioxazin-3- or 5- or 6-yl; 1,4,2-dioxazin-3- or 5- or 6-yl; 1,4,2-dioxazepan-2- or 3- or 5- or 6- or 7-yl; 6,7-dihydro-5H-1,4,2-dioxazepin-3- or 5- or 6- or 7-yl; 2,3-dihydro-7H-1,4,2-dioxazepin-2- or 3- or 5- or 6- or 7-yl; 2,3-dihydro-5H-1,4,2-dioxazepin-2- or 3- or 5- or 6- or 7-yl; 5H-1,4,2-dioxazepin-3- or 5- or 6- or 7-yl; 7H-1,4,2-dioxazepin-3- or 5- or 6- or 7-yl. Structural examples of heterocycles which are optionally substituted further are also listed below:

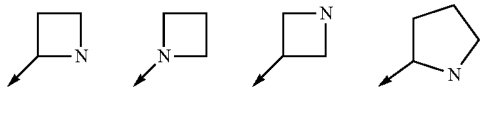

-continued

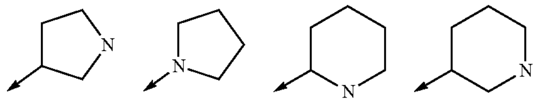
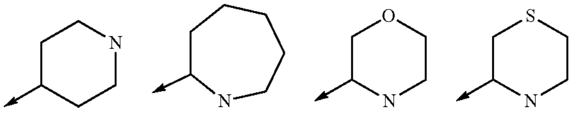
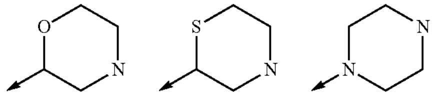
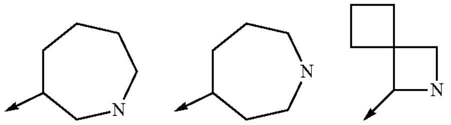
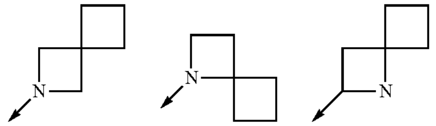
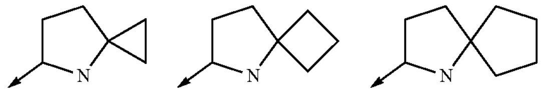
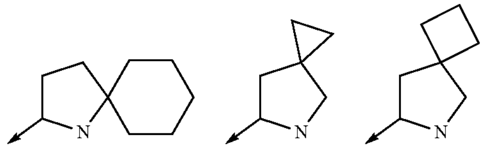
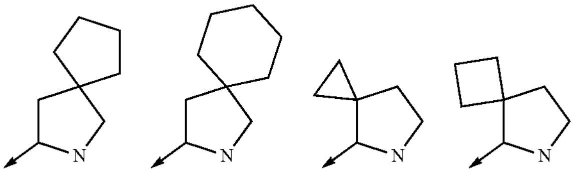
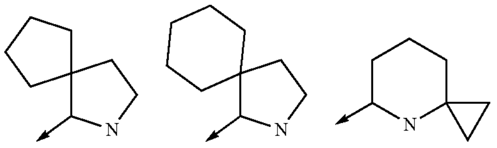
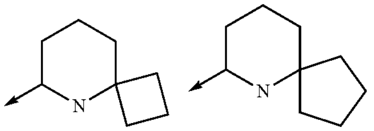
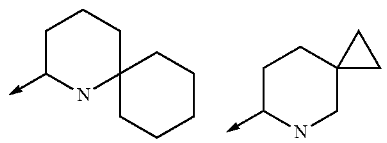
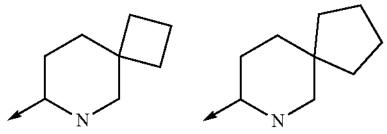
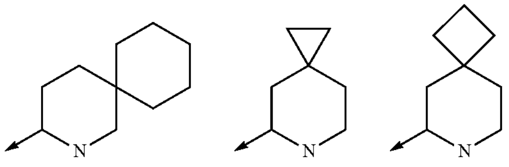

-continued
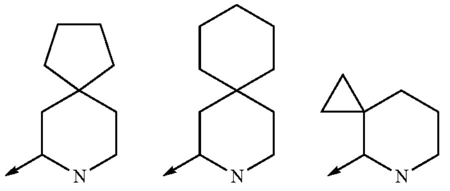
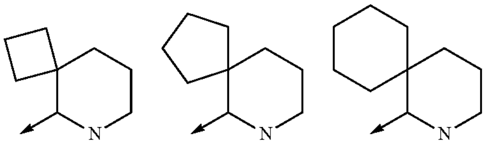
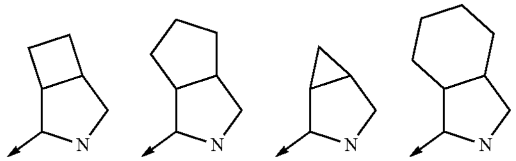
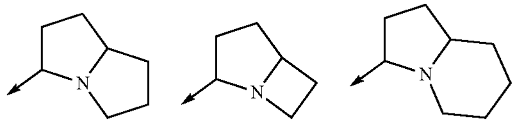
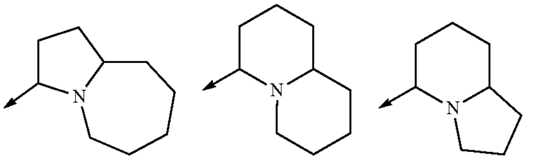
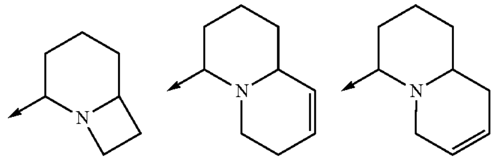
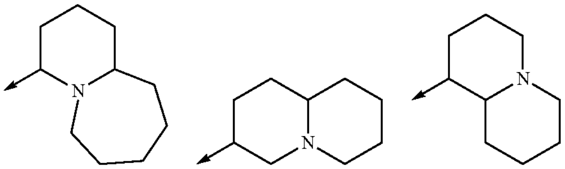
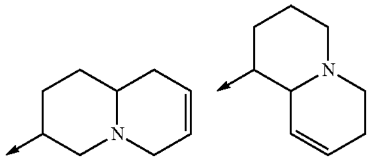
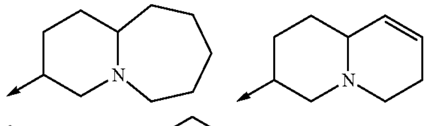
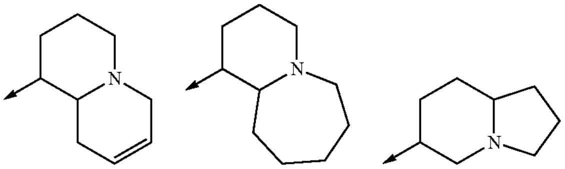
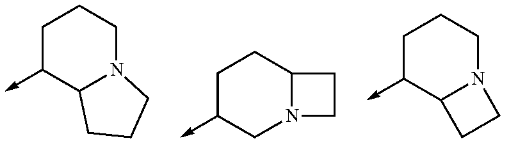
-continued
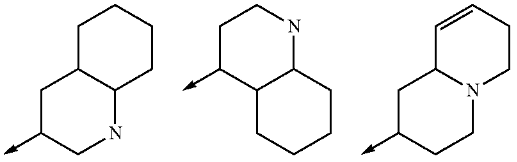
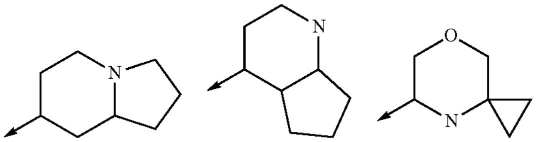
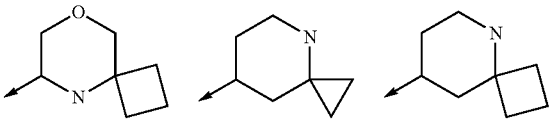
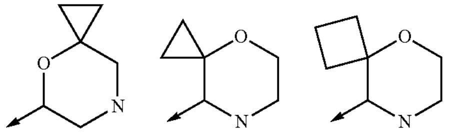
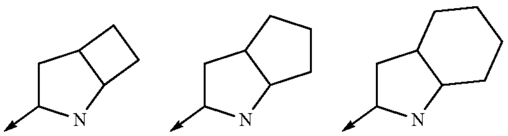
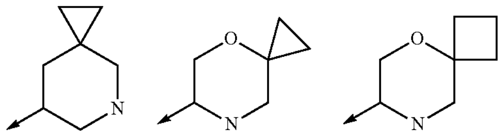
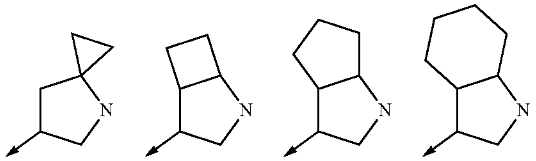
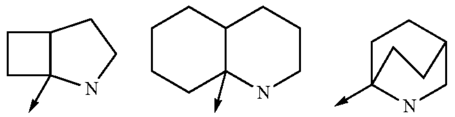
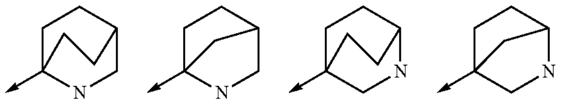
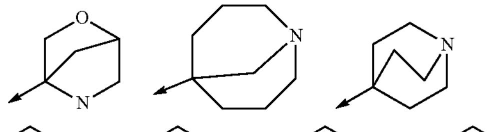
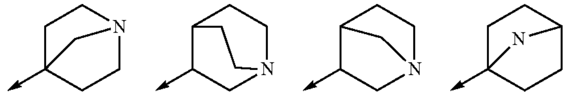
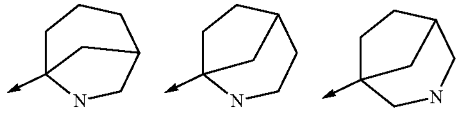
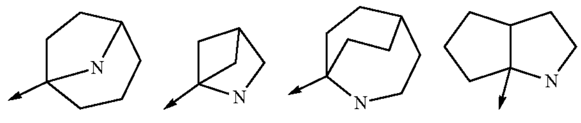

-continued

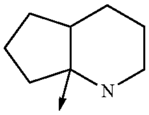

The heterocycles listed above are preferably substituted, for example, by hydrogen, halogen, alkyl, haloalkyl, hydroxyl, alkoxy, cycloalkoxy, aryloxy, alkoxyalkyl, alkoxyalkoxy, cycloalkyl, halocycloalkyl, aryl, arylalkyl, heteroaryl, heterocyclyl, alkenyl, alkylcarbonyl, cycloalkylcarbonyl, arylcarbonyl, heteroarylcarbonyl, alkoxycarbonyl, hydroxycarbonyl, cycloalkoxycarbonyl, cycloalkylalkoxycarbonyl, alkoxycarbonylalkyl, arylalkoxycarbonyl, arylalkoxycarbonylalkyl, alkynyl, alkynylalkyl, alkylalkynyl, trisalkylsilylalkynyl, nitro, amino, cyano, haloalkoxy, haloalkylthio, alkylthio, hydrothio, hydroxyalkyl, oxo, heteroarylalkoxy, arylalkoxy, heterocyclylalkoxy, heterocyclylalkylthio, heterocyclyloxy, heterocyclylthio, heteroaryloxy, bisalkylamino, alkylamino, cycloalkylamino, hydroxycarbonylalkylamino, alkoxycarbonylalkylamino, arylalkoxycarbonylalkylamino, alkoxycarbonylalkyl(alkyl)amino, aminocarbonyl, alkylaminocarbonyl, bisalkylaminocarbonyl, cycloalkylaminocarbonyl, hydroxycarbonylalkylaminocarbonyl, alkoxycarbonylalkylaminocarbonyl, arylalkoxycarbonylalkylaminocarbonyl.

When a base structure is substituted "by one or more radicals" from a list of radicals (=group) or a generically defined group of radicals, this in each case includes simultaneous substitution by a plurality of identical and/or structurally different radicals.

In the case of a partly or fully saturated nitrogen heterocycle, this may be joined to the remainder of the molecule either via carbon or via the nitrogen.

Suitable substituents for a substituted heterocyclic radical are the substituents specified further down, and additionally also oxo and thioxo. The oxo group as a substituent on a ring carbon atom is then, for example, a carbonyl group in the heterocyclic ring. As a result, lactones and lactams are preferably also included.

The oxo group may also occur on the ring heteroatoms, which may exist in different oxidation states, for example in the case of N and S, and in that case form, for example, the divalent —N(O)—, —S(O)— (also SO for short) and —$S(O)_2$— (also $SO_2$ for short) groups in the heterocyclic ring. In the case of —N(O)— and —S(O)— groups, both enantiomers in each case are included.

According to the invention, the expression "heteroaryl" represents heteroaromatic compounds, i.e. fully unsaturated aromatic heterocyclic compounds, preferably 5- to 7-membered rings having 1 to 4, preferably 1 or 2, identical or different heteroatoms, preferably O, S or N. Inventive heteroaryls are, for example, 1H-pyrrol-1-yl; 1H-pyrrol-2-yl; 1H-pyrrol-3-yl; furan-2-yl; furan-3-yl; thien-2-yl; thien-3-yl, 1H-imidazol-1-yl; 1H-imidazol-2-yl; 1H-imidazol-4-yl; 1H-imidazol-5-yl; 1H-pyrazol-1-yl; 1H-pyrazol-3-yl; 1H-pyrazol-4-yl; 1H-pyrazol-5-yl, 1H-1,2,3-triazol-1-yl, 1H-1,2,3-triazol-4-yl, 1H-1,2,3-triazol-5-yl, 2H-1,2,3-triazol-2-yl, 2H-1,2,3-triazol-4-yl, 1H-1,2,4-triazol-1-yl, 1H-1,2,4-triazol-3-yl, 4H-1,2,4-triazol-4-yl, 1,2,4-oxadiazol-3-yl, 1,2,4-oxadiazol-5-yl, 1,3,4-oxadiazol-2-yl, 1,2,3-oxadiazol-4-yl, 1,2,3-oxadiazol-5-yl, 1,2,5-oxadiazol-3-yl, azepinyl, pyridin-2-yl, pyridin-3-yl, pyridin-4-yl, pyrazin-2-yl, pyrazin-3-yl, pyrimidin-2-yl, pyrimidin-4-yl, pyrimidin-5-yl, pyridazin-3-yl, pyridazin-4-yl, 1,3,5-triazin-2-yl, 1,2,4-triazin-3-yl, 1,2,4-triazin-5-yl, 1,2,4-triazin-6-yl, 1,2,3-triazin-4-yl, 1,2,3-triazin-5-yl, 1,2,4-, 1,3,2-, 1,3,6- and 1,2,6-oxazinyl, isoxazol-3-yl, isoxazol-4-yl, isoxazol-5-yl, 1,3-oxazol-2-yl, 1,3-oxazol-4-yl, 1,3-oxazol-5-yl, isothiazol-3-yl, isothiazol-4-yl, isothiazol-5-yl, 1,3-thiazol-2-yl, 1,3-thiazol-4-yl, 1,3-thiazol-5-yl, 1,3,4-thiadiazol-2-yl, 1,3,4-thiadiazol-5-yl, 1,2,4-thiadiazol-5-yl, 1,2,4-thiadiazol-3-yl, 1,2,5-thiadiazol-3-yl, 1,2,5-thiadiazol-3-yl, 1,2,3-thiadiazol-4-yl, 1,2,3-thiadiazol-5-yl, oxepinyl, thiepinyl, 1,2,4-triazolonyl and 1,2,4-diazepinyl, 2H-1,2,3,4-tetrazol-5-yl, 1H-1,2,3,4-tetrazol-5-yl, 1,2,3,4-oxatriazol-5-yl, 1,2,3,4-thiatriazol-5-yl, 1,2,3,5-oxatriazol-4-yl, 1,2,3,5-thiatriazol-4-yl. The heteroaryl groups of the invention may also be substituted by one or more identical or different radicals.

If two adjacent carbon atoms are part of a further aromatic ring, the systems are fused heteroaromatic systems, such as benzofused or polyannelated heteroaromatics. Preferred examples are quinolines (e.g. quinolin-2-yl, quinolin-3-yl, quinolin-4-yl, quinolin-5-yl, quinolin-6-yl, quinolin-7-yl, quinolin-8-yl); isoquinolines (e.g. isoquinolin-1-yl, isoquinolin-3-yl, isoquinolin-4-yl, isoquinolin-5-yl, isoquinolin-6-yl, isoquinolin-7-yl, isoquinolin-8-yl); quinoxaline; quinazoline; cinnoline; 1,5-naphthyridine; 1,6-naphthyridine; 1,7-naphthyridine; 1,8-naphthyridine; 2,6-naphthyridine; 2,7-naphthyridine; phthalazine; pyridopyrazines; pyridopyrimidines; pyridopyridazines; pteridines; pyrimidopyrimidines. Examples of heteroaryl are also 5- or 6-membered benzofused rings from the group of 1H-indol-1-yl, 1H-indol-2-yl, 1H-indol-3-yl, 1H-indol-4-yl, 1H-indol-5-yl, 1H-indol-6-yl, 1H-indol-7-yl, 1-benzofuran-2-yl, 1-benzofuran-3-yl, 1-benzofuran-4-yl, 1-benzofuran-5-yl, 1-benzofuran-6-yl, 1-benzofuran-7-yl, 1-benzo-thiophen-2-yl, 1-benzothiophen-3-yl, 1-benzothiophen-4-yl, 1-benzothiophen-5-yl, 1-benzothiophen-6-yl, 1-benzothiophen-7-yl, 1H-indazol-1-yl, 1H-indazol-3-yl, 1H-indazol-4-yl, 1H-indazol-5-yl, 1H-indazol-6-yl, 1H-indazol-7-yl, 2H-indazol-2-yl, 2H-indazol-3-yl, 2H-indazol-4-yl, 2H-indazol-5-yl, 2H-indazol-6-yl, 2H-indazol-7-yl, 2H-isoindol-2-yl, 2H-isoindol-1-yl, 2H-isoindol-3-yl, 2H-isoindol-4-yl, 2H-isoindol-5-yl, 2H-isoindol-6-yl; 2H-isoindol-7-yl, 1H-benzimidazol-1-yl, 1H-benzimidazol-2-yl, 1H-benzimidazol-4-yl, 1H-benzimidazol-5-yl, 1H-benzimidazol-6-yl, 1H-benzimidazol-7-yl, 1,3-benzoxazol-2-yl, 1,3-benzoxazol-4-yl, 1,3-benzoxazol-5-yl, 1,3-benzoxazol-6-yl, 1,3-benzoxazol-7-yl, 1,3-benzothiazol-2-yl, 1,3-benzothiazol-4-yl, 1,3-benzothiazol-5-yl, 1,3-benzothiazol-6-yl, 1,3-benzothiazol-7-yl, 1,2-benzisoxazol-3-yl, 1,2-benzisoxazol-4-yl, 1,2-benzisoxazol-5-yl, 1,2-benzisoxazol-6-yl, 1,2-benzisoxazol-7-yl, 1,2-benzisothiazol-3-yl, 1,2-benzisothiazol-4-yl, 1,2-benzisothiazol-5-yl, 1,2-benzisothiazol-6-yl, 1,2-benzisothiazol-7-yl.

The term "halogen" denotes, for example, fluorine, chlorine, bromine or iodine. If the term is used for a radical, "halogen" denotes, for example, a fluorine, chlorine, bromine or iodine atom.

According to the invention, "alkyl" means a straight-chain or branched open-chain, saturated hydrocarbon radical which is optionally mono- or polysubstituted, and in the latter case is referred to as "substituted alkyl". Preferred substituents are halogen atoms, alkoxy, haloalkoxy, cyano, alkylthio, haloalkylthio, cycloalkyl, alkoxycarbonyl, hydroxycarbonyl, heterocyclyl, hetaryl, aryl, amino or nitro groups, particular preference being given to methoxy, methyl, fluoroalkyl, cyano, nitro, fluorine, chlorine, bromine or iodine. The prefix "bis" also includes the combination of different alkyl radicals, e.g. methyl(ethyl) or ethyl(methyl).

"Haloalkyl", "-alkenyl" and "-alkynyl" respectively denote alkyl, alkenyl and alkynyl partly or fully substituted by identical or different halogen atoms, for example monohaloalkyl such as $CH_2CH_2Cl$, $CH_2CH_2Br$, $CHClCH_3$, $CH_2Cl$, $CH_2F$; perhaloalkyl such as $CCl_3$, $CClF_2$, $CFCl_2$, $CF_2CClF_2$, $CF_2CClFCF_3$; polyhaloalkyl such as $CH_2CHFCl$, $CF_2CClFH$, $CF_2CBrFH$, $CH_2CF_3$; the term perhaloalkyl also encompasses the term perfluoroalkyl.

"Partially fluorinated alkyl" denotes a straight-chain or branched, saturated hydrocarbon which is mono- or polysubstituted by fluorine, where the fluorine atoms in question may be present as substituents on one or more different carbon atoms of the straight-chain or branched hydrocarbon chain, for example $CHFCH_3$, $CH_2CH_2F$, $CH_2CH_2CF_3$, $CHF_2$, $CH_2F$, $CHFCF_2CF_3$.

"Partly fluorinated haloalkyl" denotes a straight-chain or branched, saturated hydrocarbon which is substituted by different halogen atoms with at least one fluorine atom, where any other halogen atoms optionally present are selected from the group consisting of fluorine, chlorine or bromine, iodine. The corresponding halogen atoms may be present as substituents on one or more different carbon atoms of the straight-chain or branched hydrocarbon chain. Partly fluorinated haloalkyl also includes full substitution of the straight or branched chain by halogen including at least one fluorine atom.

"Haloalkoxy" is, for example, $OCF_3$, $OCHF_2$, $OCH_2F$, $OCF_2CF_3$, $OCH_2CF_3$ and $OCH_2CH_2Cl$; this applies correspondingly to haloalkenyl and other halogen-substituted radicals.

The expression "($C_1$-$C_4$)-alkyl" mentioned here by way of example is a brief notation for straight-chain or branched alkyl having one to 4 carbon atoms according to the range stated for carbon atoms, i.e. encompasses the methyl, ethyl, 1-propyl, 2-propyl, 1-butyl, 2-butyl, 2-methylpropyl or tert-butyl radicals. General alkyl radicals with a larger specified range of carbon atoms, e.g. "($C_1$-$C_6$)-alkyl", correspondingly also encompass straight-chain or branched alkyl radicals with a greater number of carbon atoms, i.e. according to the example also the alkyl radicals having 5 and 6 carbon atoms.

Unless stated specifically, preference is given to the lower carbon skeletons, for example having from 1 to 6 carbon atoms, or having from 2 to 6 carbon atoms in the case of unsaturated groups, in the case of the hydrocarbon radicals such as alkyl, alkenyl and alkynyl radicals, including in composite radicals. Alkyl radicals, including in composite radicals such as alkoxy, haloalkyl, etc., are, for example, methyl, ethyl, n-propyl or i-propyl, n-, t- or 2-butyl, pentyls, hexyls such as n-hexyl, i-hexyl and 1,3-dimethylbutyl, heptyls such as n-heptyl, 1-methylhexyl and 1,4-dimethylpentyl; alkenyl and alkynyl radicals are defined as the possible unsaturated radicals corresponding to the alkyl radicals, where at least one double bond or triple bond is present. Preference is given to radicals having one double bond or triple bond.

The term "alkenyl" also includes, in particular, straight-chain or branched open-chain hydrocarbon radicals having more than one double bond, such as 1,3-butadienyl and 1,4-pentadienyl, but also allenyl or cumulenyl radicals having one or more cumulated double bonds, for example allenyl (1,2-propadienyl), 1,2-butadienyl and 1,2,3-pentatrienyl. Alkenyl denotes, for example, vinyl which may optionally be substituted by further alkyl radicals, for example (but not limited thereto) ($C_2$-$C_6$)-alkenyl such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl.

The term "alkynyl" also includes, in particular, straight-chain or branched open-chain hydrocarbon radicals having more than one triple bond, or else having one or more triple bonds and one or more double bonds, for example 1,3-butatrienyl or 3-penten-1-yn-1-yl. ($C_2$-$C_6$)-Alkynyl denotes, for example, ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl.

The term "cycloalkyl" refers to a carbocyclic saturated ring system having preferably 3-8 ring carbon atoms, for example cyclopropyl, cyclobutyl, cyclopentyl or cyclohexyl, which optionally has further substitution, preferably by hydrogen, alkyl, alkoxy, cyano, nitro, alkylthio, haloalkylthio, halogen, alkenyl, alkynyl, haloalkyl, amino, alkylamino, bisalkylamino, alkoxycarbonyl, hydroxycarbonyl, arylalkoxycarbonyl, aminocarbonyl, alkylaminocarbonyl, cycloalkylaminocarbonyl. In the case of optionally substituted cycloalkyl, cyclic systems with substituents are included, also including substituents with a double bond on the cycloalkyl radical, for example an alkylidene group such as methylidene. In the case of optionally substituted cycloalkyl, polycyclic aliphatic systems are also included, for example bicyclo[1.1.0]butan-1-yl, bicyclo[1.1.0]butan-2-yl, bicyclo[2.1.0]pentan-1-yl, bicyclo[1.1.1]pentan-1-yl, bicyclo[2.1.0]pentan-2-yl, bicyclo[2.1.0]pentan-5-yl, bicyclo [2.1.1]hexyl, bicyclo[2.2.1]hept-2-yl, bicyclo[2.2.2]octan-2-yl, bicyclo[3.2.1]octan-2-yl, bicyclo[3.2.2]nonan-2-yl, adamantan-1-yl and adamantan-2-yl, but also systems such as 1,1'-bi(cyclopropyl)-1-yl, 1,1'-bi(cyclopropyl)-2-yl, for example. The term "($C_3$-$C_7$)-cycloalkyl" is a brief notation for cycloalkyl having three to 7 carbon atoms, corresponding to the range specified for carbon atoms.

In the case of substituted cycloalkyl, spirocyclic aliphatic systems are also included, for example spiro[2.2]pent-1-yl, spiro[2.3]hex-1-yl, spiro[2.3]hex-4-yl, 3-spiro[2.3]hex-5-yl, spiro[3.3]hept-1-yl, spiro[3.3]hept-2-yl.

"Cycloalkenyl" denotes a carbocyclic, nonaromatic, partly unsaturated ring system having preferably 4-8 carbon atoms, e.g. 1-cyclobutenyl, 2-cyclobutenyl, 1-cyclopentenyl, 2-cyclopentenyl, 3-cyclopentenyl, or 1-cyclohexenyl, 2-cyclohexenyl, 3-cyclohexenyl, 1,3-cyclohexadienyl or 1,4-cyclohexadienyl, also including substituents with a double bond on the cycloalkenyl radical, for example an alkylidene group such as methylidene. In the case of optionally substituted cycloalkenyl, the elucidations for substituted cycloalkyl apply correspondingly.

The term "alkylidene", also, for example, in the form ($C_1$-$C_{10}$)-alkylidene, denotes the radical of a straight-chain or branched open-chain hydrocarbon radical which is attached via a double bond. Possible bonding sites for alkylidene are naturally only positions on the base structure where two hydrogen atoms can be replaced by the double bond; radicals are, for example, $=CH_2$, $=CH—CH_3$, $=C(CH_3)—CH_3$, $=C(CH_3)—C_2H_5$ or $=C(C_2H_5)—C_2H_5$. Cycloalkylidene denotes a carbocyclic radical bonded via a double bond.

"Alkoxyalkyl" represents an alkoxy radical bonded via an alkyl group and "alkoxyalkoxy" denotes an alkoxyalkyl radical bonded via an oxygen atom, for example (but not limited to) methoxymethoxy, methoxyethoxy, ethoxyethoxy, methoxy-n-propyloxy.

"Arylalkyl" represents an aryl radical bonded via an alkyl group, "heteroarylalkyl" denotes a heteroaryl radical bonded via an alkyl group, and "heterocyclylalkyl" denotes a heterocyclyl radical bonded via an alkyl group.

"Cycloalkylalkyl" represents a cycloalkyl radical bonded via an alkyl group, for example (but not limited thereto) cyclopropylmethyl, cyclobutylmethyl, cyclopentylmethyl, cyclohexylmethyl, 1-cyclopropyleth-1-yl, 2-cyclopropyleth-1-yl, 1-cyclopropylprop-1-yl, 3-cyclopropylprop-1-yl.

According to the invention, "haloalkylthio"—on its own or as constituent part of a chemical group—is straight-chain or branched S-haloalkyl, preferably having 1 to 8, or having 1 to 6 carbon atoms, such as ($C_1$-$C_8$)—, ($C_1$-$C_6$)- or ($C_1$-$C_4$)-haloalkylthio, for example (but not limited to) trifluoromethylthio, pentafluoroethylthio, difluoromethyl, 2,2-difluoroeth-1-ylthio, 2,2,2-difluoroeth-1-ylthio, 3,3,3-prop-1-ylthio.

"Halocycloalkyl" denotes cycloalkyl or cycloalkenyl partly or fully substituted by identical or different halogen atoms, such as F, Cl and Br, or by haloalkyl, such as trifluoromethyl or difluoromethyl, for example 1-fluorocycloprop-1-yl, 2-fluorocycloprop-1-yl, 2,2-difluorocycloprop-1-yl, 1-fluorocyclobut-1-yl, 1-trifluoromethylcycloprop-1-yl, 2-trifluoromethylcycloprop-1-yl, 1-chlorocycloprop-1-yl, 2-chlorocycloprop-1-yl, 2,2-dichlorocycloprop-1-yl, 3,3-difluorocyclobutyl.

If the compounds can form, through a hydrogen shift, tautomers whose structure would not formally be covered by the general formula (I), these tautomers are nevertheless encompassed by the definition of the inventive compounds of the general formula (I), unless a particular tautomer is under consideration. For example, many carbonyl compounds may be present both in the keto form and in the enol form, both forms being encompassed by the definition of the compound of the general formula (I).

Depending on the nature of the substituents and the manner in which they are attached, the compounds of the general formula (I) may be present as stereoisomers. The possible stereoisomers defined by the specific three-dimensional form thereof, such as enantiomers, diastereomers, Z and E isomers, are all encompassed by the general formula (I). If, for example, one or more alkenyl groups are present, diastereomers (Z and E isomers) may occur. If, for example, one or more asymmetric carbon atoms are present, enantiomers and diastereomers may occur. Stereoisomers can be obtained from the mixtures obtained in the preparation by customary separation methods. The chromatographic separation can be effected either on the analytical scale to find the enantiomeric excess or the diastereomeric excess, or else on the preparative scale to produce test specimens for biological testing. It is likewise possible to selectively prepare stereoisomers by using stereoselective reactions with use of optically active starting materials and/or auxiliaries. The invention thus also relates to all stereoisomers which are embraced by the general formula (I) but are not shown in their specific stereomeric form, and to mixtures thereof.

If the compounds are obtained as solids, the purification can also be carried out by recrystallization or digestion. If individual compounds (I) cannot be obtained in a satisfactory manner by the routes described below, they can be prepared by derivatization of other compounds (I).

Suitable isolation methods, purification methods and methods for separating stereoisomers of compounds of the general formula (I) are methods generally known to the person skilled in the art from analogous cases, for example by physical processes such as crystallization, chromatographic methods, in particular column chromatography and HPLC (high pressure liquid chromatography), distillation, optionally under reduced pressure, extraction and other methods, any mixtures that remain can generally be separated by chromatographic separation, for example on chiral solid phases. Suitable for preparative amounts or on an industrial scale are processes such as crystallization, for example of diastereomeric salts which can be obtained from the diastereomer mixtures using optically active acids and, if appropriate, provided that acidic groups are present, using optically active bases.

Synthesis of [(5-phenyl-1-(heteroaryl)-1H-1,2,4-triazol-3-yl)oxy]acetic acid derivatives of the general formula (I)

(I)

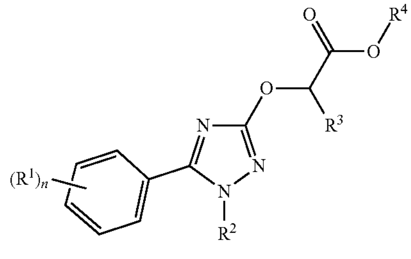

The inventive [(5-phenyl-1-(hetero aryl)-1H-1,2,4-triazol-3-yl)oxy] acetic acid derivatives of the general formula (I) can be prepared proceeding from known processes. The synthesis routes used and examined proceed from commercially available or readily preparable substituted benzoic acids, from correspondingly substituted benzamides and from commercially available chemicals, such as substituted heteroaryl hydrazines and diphenyl carbonate. In the schemes which follow, the moieties $R^1$, $R^2$, $R^3$, $R^4$, n and p in the general formula (I) have the meanings defined above, unless illustrative but non-limiting definitions are given.

The inventive compounds of the general formula (Ia) are synthesized via a reaction of the compound of the general formula (II) with a compound of the general formula (III) in the presence of a base, for example potassium carbonate. The reaction preferably takes place in the temperature range between 0° C. and 120° C., in a suitable solvent, for example acetonitrile (see scheme 1).

Scheme 1.

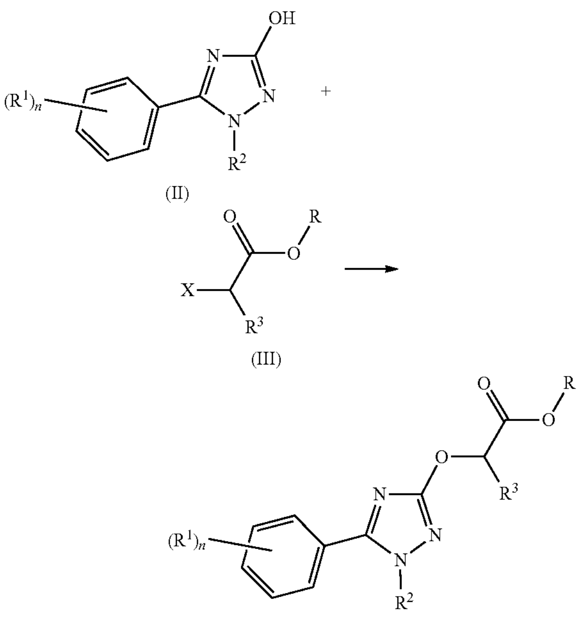

(II)

(III)

(Ia)

with X = halogen and R = $(C_1-C_4)$-alkyl.

The compounds of the general formula (II) are synthesized via a cyclization of a compound of the general formula (IV) in the presence of a condensation reagent, for example polyphosphoric acid. The reaction preferably takes place within the temperature range between 0° C. and 180° C., in neat form (see scheme 2).

Scheme 2.

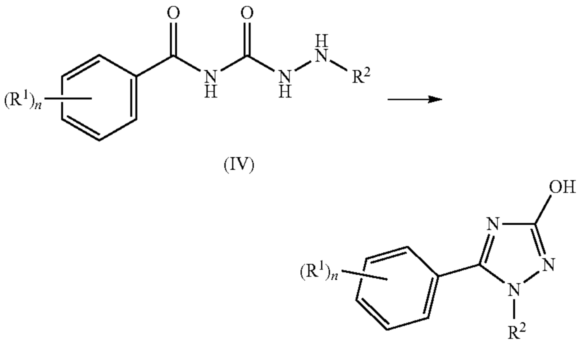

(IV)

(II)

The synthesis of compounds of the general formula (IV) can be prepared by reaction of the compound of the general formula (V) with a phenylhydrazine of the general formula (VI) in a suitable solvent, for example acetonitrile, within a temperature range between −20° C. and 100° C., preferably −5° C. and 50° C. The reaction takes place in the presence of a base, for example triethylamine. Rather than heteroarylhydrazines of the general formula (VI), it is also possible to use heteroarylhydrazine hydrohalides of the general formula (VII) (scheme 3).

Scheme 3.

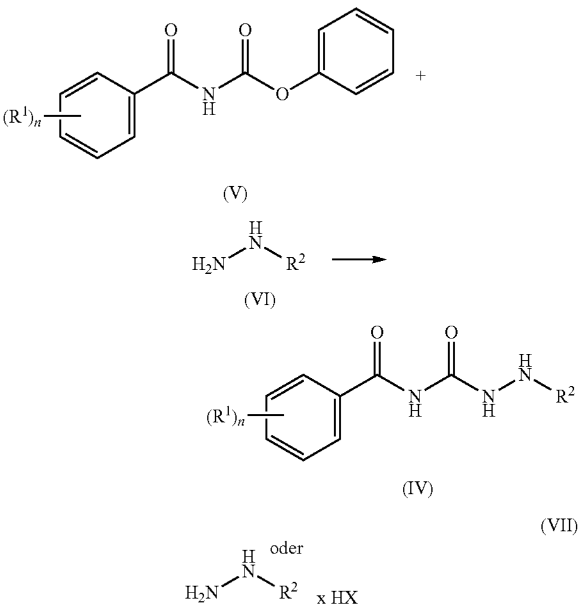

(V)

(VI)

(IV)

(VII)

oder x HX with X = halogen.

The synthesis of the compound of the general formula (V) can be prepared by reaction of the compound of the general formula (VIII) with diphenyl carbonate (IX) in the presence of a base, for example sodium hydride (see Scheme 4). The reaction preferably takes place in the temperature range between −20° C. and 150° C., in a suitable solvent, for example THF. The compounds of the general formula (VIII) and (IX) are commercially available or can be prepared analogously to methods known to the person skilled in the art.

Scheme 4.

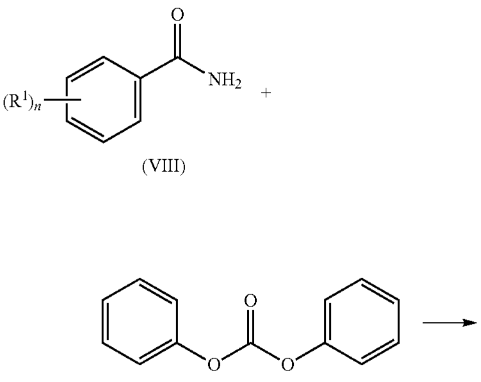

(VIII)

(IX)

-continued

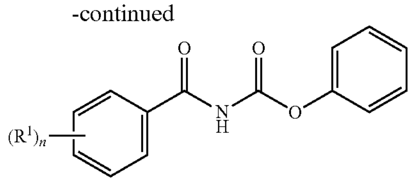

(V)

The synthesis of the acid of the general formula (X) can be prepared by hydrolysis of the compound of the general formula (Ia) by or analogously to methods known to those skilled in the art.

The hydrolysis can be carried out in the presence of a base or a Lewis acid. The base may be a hydroxide salt of an alkali metal (for example lithium, sodium or potassium; Scheme 5), and the hydrolysis reaction preferably takes place in the temperature range between room temperature and 100° C. The Lewis acid may be boron tribromide, and the reaction can be carried out within a temperature range between −20° C. and 100° C., preferably −5° C. and 50° C.

Scheme 5.

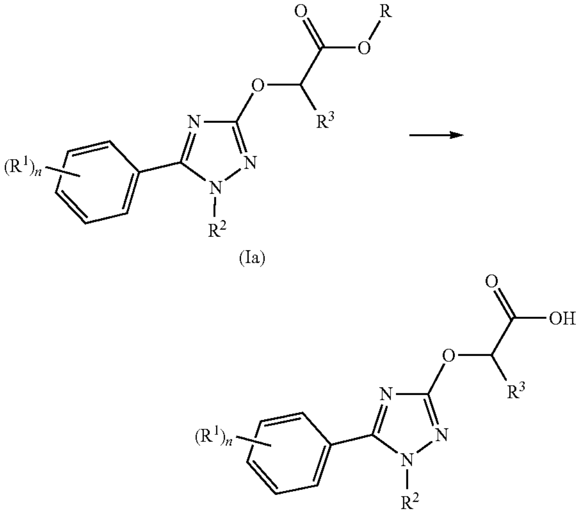

(Ia)

(X)

with R = $(C_1\text{-}C_4)$-alkyl

The inventive compounds of the general formula (XI) are synthesized via an esterification of an acid of the general formula (X) with an alcohol of the general formula (XII) in the presence of a coupling reagent, for example T3P, dicyclohexylcarbodiimide, N-(3-dimethylaminopropyl)-N'-ethylcarbodiimide, N,N'-carbonyldiimidazole, 2-chloro-1,3-dimethylimidazolium chloride or 2-chloro-1-methylpyridinium iodide (see Chemistry of Peptide Synthesis, Ed. N. Leo Benoiton, Taylor & Francis, 2006, ISBN-10: 1-57444-454-9). Polymer-supported reagents, for example polymer-supported dicyclohexylcarbodiimide, are also suitable for this coupling reaction. The reaction takes place preferably within the temperature range between 0° C. and 80° C., in an appropriate solvent, for example dichloromethane, acetonitrile, N,N-dimethylformamide or ethyl acetate, and in the presence of a base, for example triethylamine, N,N-diisopropylethylamine or 1,8-diazabicyclo[5.4.0]undec-7-ene (see Scheme 6). For T3P coupling conditions see *Organic Process Research & Development* 2009, 13, 900-906.

Scheme 6.

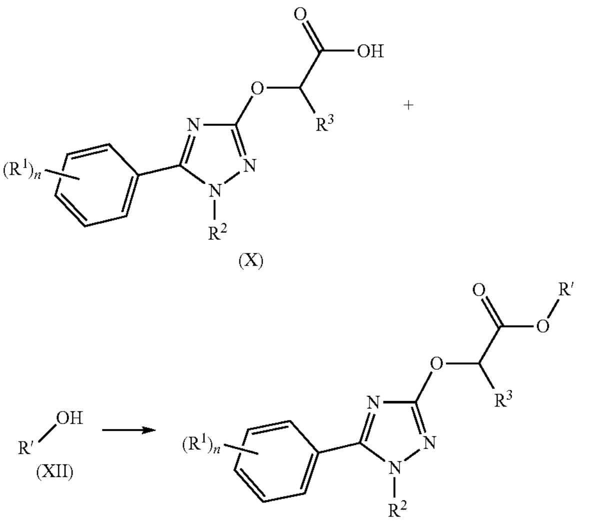

(X)

(XII)

(XI)

Scheme 7 shows the synthesis of the compound of the general formula (II); the synthesis is effected by reaction of a compound of the general formula (XIII) in the presence of a Brønsted acid, for example 33% HBr in acetic acid. The reaction preferably takes place in the temperature range between 0° C. and 180° C. See Bioorganic & Medicinal Chemistry 2018, 26, 3321-3344.

Scheme 7.

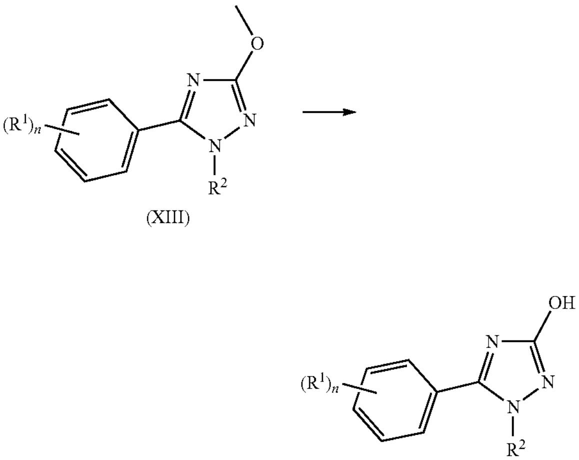

(XIII)

(II)

Compounds of the general formula (XIII) can be prepared by reaction of a compound of the general formula (XIV) and a heteroarylhydrazine of the general formula (VI) in a suitable solvent, for example ethanol (see Scheme 8). The reaction preferably takes place in the temperature range between 0° C. and 150° C.

Scheme 8.

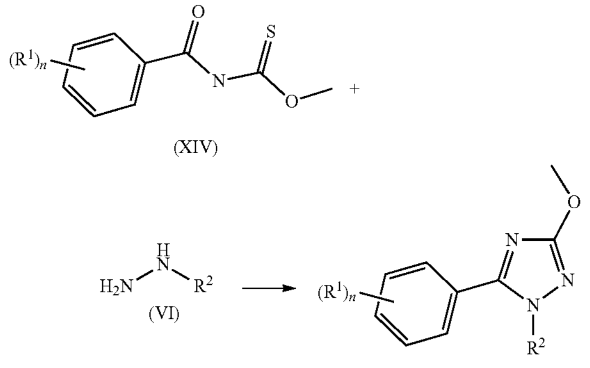

(XIV)

(VI)

(XIII)

The compounds of the general formula (XIV) can be prepared by reaction of benzoyl halides of the general formula (XV) with a thiocyanate salt of the general formula (XVI) in the presence of methanol in a suitable solvent, for example acetone (see Scheme 9). The benzoyl halides are either commercially available or can be prepared analogously to methods known to the person skilled in the art. See Tetrahedron 1968, 24, 5205-5214; J. Chem. Soc. 1957, 1091; JP81 53, 664 (1981); Justus Liebigs Ann. Chem. 1964, 675, 180 and J. heterocycl. Chem. 1983, 20, 1533.

Scheme 9.

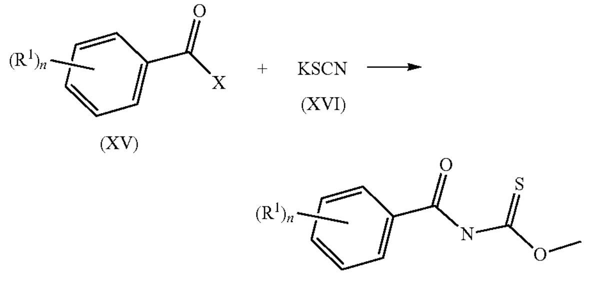

(XV)

(XVI)

(XIV)

with X = fluorine, chlorine, bromine.

Selected detailed synthesis examples for the inventive compounds of the general formula (I) are adduced below. The example numbers mentioned correspond to the numbering scheme in Tables I.1 to 1.77 below.

The $^1$H NMR, $^{13}$C-NMR and $^{19}$F-NMR spectroscopy data reported for the chemical examples described in the sections which follow (400 MHz for $^1$H NMR and 150 MHz for $^{13}$C-NMR and 375 MHz for $^{19}$F-NMR, solvent $CDCl_3$, $CD_3OD$ or $d_6$-DMSO, internal standard: tetramethylsilane δ=0.00 ppm) were obtained on a Bruker instrument, and the signals listed have the meanings given below: br=broad; s=singlet, d=doublet, t=triplet, dd=doublet of doublets, ddd=doublet of a doublet of doublets, m=multiplet, q=quartet, quint=quintet, sext=sextet, sept=septet, dq=doublet of quartets, dt=doublet of triplets. In the case of diastereomer mixtures, either the significant signals for each of the two diastereomers are reported or the characteristic signal of the main diastereomer is reported. The abbreviations used for chemical groups have, for example, the following meanings: Me=$CH_3$, Et=$CH_2CH_3$, t-Hex=$C(CH_3)_2CH(CH_3)_2$, t-Bu=$C(CH_3)$ 3, n-Bu=unbranched butyl, n-Pr=unbranched propyl, i-Pr=branched propyl, c-Pr=cyclopropyl, c-Hex=cyclohexyl.

SYNTHESIS EXAMPLES

Synthesis Example No.: 1.42-11

Synthesis Stage 1: Phenyl (2,4-difluorobenzoyl)carbamate

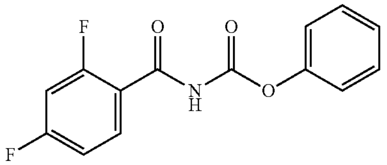 [SMILES: O=C(NC(=O)c1ccc(F)cc1F)Oc1ccccc1]

2,4-Difluorobenzamide (10 g, 63.65 mmol, 1.0 equiv) and diphenyl carbonate (20.45 g, 1.5 equiv) were dissolved in THF (100 ml) under an argon atmosphere and cooled down to 0° C. with an ice bath. Sodium hydride (60% in mineral oil, 2.55 g, 63.65 mmol, 1.0 equiv) was added in portions to the solution. Caution: evolution of gas! Subsequently, the ice bath is removed and the reaction mixture is stirred at room temperature for 1 h. Thereafter, the reaction mixture was concentrated to ⅓ under reduced pressure, forming a flaky white solid. The resultant solid was filtered off with suction and dried under air. Phenyl (2,4-difluorobenzoyl)carbamate was isolated in the form of a white solid (11.51 g, 61% of theory). $^1$H-NMR (400 MHz, DMSO-$d^6$ δ, ppm) 7.76 (m, 1H), 7.36-7.28 (m, 2H), 7.18-6.99 (m, 4H), 6.77-6.74 (m, 2H).

Synthesis Stage 2: 2N-(2,4-Difluorobenzoyl)-2-(5-fluoropyridin-2-yl)hydrazinecarboxamide

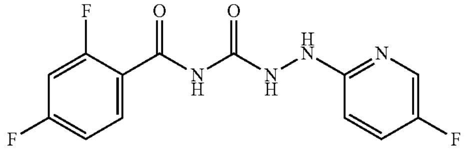 [SMILES: O=C(NNc1ccc(F)cn1)NC(=O)c1ccc(F)cc1F]

Phenyl (2,4-difluorobenzoyl)carbamate (2.5 g, 9.02 mmol, 1.0 equiv) was dissolved in acetonitrile (100 ml) and then the following were added at room temperature: 5-fluoro-2-hydrazinopyridine (1.26 g, 9.92 mmol, 1.1 equiv) and triethylamine (3.77 ml, 27.05 mmol, 3.0 equiv). The solution turned pink after about 15-30 min, and a beige solid precipitated out. The reaction mixture was stirred at room temperature for 1 h, then the resultant precipitate was filtered off and dried under air. N-(2,4-Difluorobenzoyl)-2-(5-fluoropyridin-2-yl)hydrazinecarboxamide was isolated in the form of a beige solid (2.40 g, 42% of theory). $^1$H-NMR (400 MHz, DMSO-$d^6$ δ, ppm) 11.45 (bs, 1H), 9.63 (bs, 1H), 8.09-8.00 (m, 2H), 7.78-7.61 (m, 2H), 7.09-7.02 (m, 2H), 6.85 (d, 1H).

Synthesis Stage 3: 5-(2,4-Difluorophenyl)-1-(5-fluoropyridin-2-yl)-1H-1,2,4-triazole-3-ol

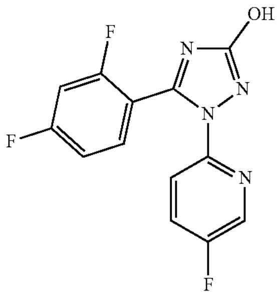 [SMILES: Oc1nc(-c2ccc(F)cc2F)n(-c2ccc(F)cn2)n1]

2N-(2,4-Difluorobenzoyl)-2-(5-fluoropyridin-2-yl)hydrazinecarboxamide (0.9 g, 2.90 mmol, 1.0 equiv) was blended in polyphosphoric acid (20 g) and then at 100° C. for 2.5 h, liquefying the reaction mixture. After having been cooled down to room temperature, the reaction mixture was added dropwise to ice-water, and the pale beige precipitate was filtered off with suction. The precipitate was filtered off with suction and dried at 55° C. in a vacuum drying cabinet. 5-(2,4-Difluorophenyl)-1-(5-fluoropyridin-2-yl)-1H-1,2,4-triazole-3-ol was isolated in the form of a pale beige solid (180 mg, 20% of theory). $^1$H-NMR (400 MHz, DMSO-$d^6$ δ, ppm) 11.80 (bs, 1H), 8.26 (m, 1H), 7.99 (m, 1H), 7.78 (m, 1H), 7.66 (m, 1H), 7.40 (m, 1H), 7.23 (m, 1H).

Synthesis Stage 4: Methyl {[5-(2,4-difluorophenyl)-1-(5-fluoropyridin-2-yl)-1H-1,2,4-triazol-3-yl]oxy}acetate (synthesis example 1.40-9)

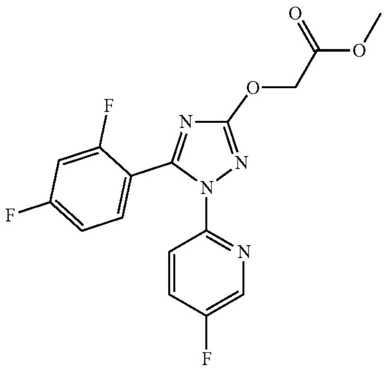 [SMILES: COC(=O)COc1nc(-c2ccc(F)cc2F)n(-c2ccc(F)cn2)n1]

5-(2,4-Difluorophenyl)-1-(5-fluoropyridin-2-yl)-1H-1,2,4-triazole-3-ol (161 mg, 0.55 mmol, 1.0 equiv) and potassium carbonate (228 mg, 1.65 mmol, 3 equiv) were suspended in acetonitrile (10 ml), and then methyl bromoacetate (126 mg, 0.83 mmol, 1.5 equiv) was added. Then the suspension was stirred at room temperature overnight, the solid was filtered off, and the reaction mixture was concentrated under reduced pressure. The residue was purified by column chromatography (ethyl acetate/heptane gradient). Methyl {[5-(2,4-difluorophenyl)-1-(5-fluoropyridin-2-yl)-1H-1,2,4-triazol-3-yl]oxy}acetate was isolated in the form of a colorless oil (152 mg, 71% of theory). $^1$H-NMR (400 MHz, $CDCl_3$ δ, ppm) 8.04 (d, 1H), 7.77-7.67 (m, 2H), 7.56 (m, 1H), 7.01 (m, 1H), 6.77 (m, 1H), 4.97 (s, 2H), 3.82 (s, 3H).

Synthesis Stage 5: {[5-(2,4-Difluorophenyl)-1-(5-fluoropyridin-2-yl)-1H-1,2,4-triazol-3-yl]oxy}acetic Acid (Synthesis Example 1.42-11)

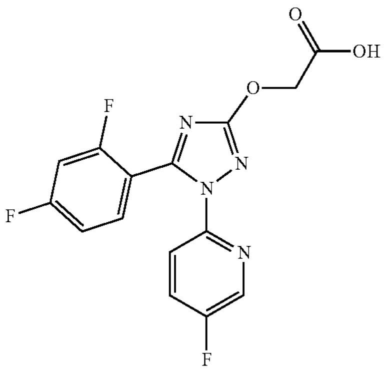 [SMILES: O=C(O)COc1nc(-c2ccc(F)cc2F)n(-c2ccc(F)cn2)n1]

Methyl {[5-(2,4-difluorophenyl)-1-(5-fluoropyridin-2-yl)-1H-1,2,4-triazol-3-yl]oxy}acetate (90 mg, mmol, 1.0 equiv) and lithium hydroxide (12 mg, 0.49 mmol, 2 equiv) were dissolved in a THF/water mixture (7:2, 13 ml) and then stirred at room temperature for 1 h. The reaction mixture was concentrated under reduced pressure. The residue was dissolved in water and adjusted to pH=2 with 2M hydrochloric acid, with precipitation of a pale yellow solid. The precipitate was filtered off with suction and dried at in a vacuum drying cabinet. {[5-(2,4-Difluorophenyl)-1-(5-fluoropyridin-2-yl)-1H-1,2,4-triazol-3-yl]oxy}acetic acid was isolated in the form of a pale yellow solid (85 mg, 93% of theory). $^1$H-NMR (400 MHz, DMSO-$d^6$ δ, ppm) 13.18 (bs, 1H), 8.31 (m, 1H), 8.01 (m, 1H), 7.79 (m, 1H), 7.71 (m, 1H), 7.37 (m, 1H), 7.25 (m, 1H), 4.91 (s, 2H).

In analogy to the preparation examples cited above and recited at the appropriate point, and taking account of the general details relating to the preparation of [(5-phenyl-1-(Heteroaryl)-1H-1,2,4-triazol-3-yl)oxy]acetic acid derivatives, the compounds listed below are obtained:

(I.1)

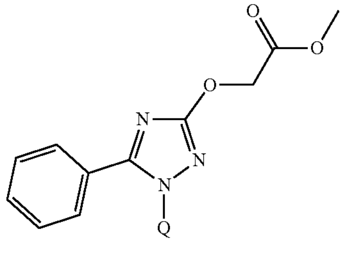

Table I.1: Preferred compounds of the formula (I.1) are the compounds I.1-1 to I.1-24 in which Q has the meanings from table 1 indicated in the respective row. Thus, the compounds I.1-1 to I.1-24 of table I.1 are defined by the meaning of the respective entry nos. 1 to 24 for Q from table 1.

TABLE 1

| No. | Q |
|---|---|
| 1 | Q-2.1 |
| 2 | Q-2.2 |

TABLE 1-continued

| No. | Q |
|---|---|
| 3 | Q-2.3 |
| 4 | Q-2.4 |
| 5 | Q-2.5 |
| 6 | Q-2.6 |
| 7 | Q-2.7 |
| 8 | Q-2.10 |
| 9 | Q-2.11 |
| 10 | Q-2.12 |
| 11 | Q-2.13 |
| 12 | Q-2.14 |
| 13 | Q-2.15 |
| 14 | Q-2.17 |
| 15 | Q-2.18 |
| 16 | Q-2.19 |
| 17 | Q-2.21 |
| 18 | Q-2.22 |
| 19 | Q-2.24 |
| 20 | Q-2.25 |
| 21 | Q-2.56 |
| 22 | Q-2.57 |
| 23 | Q-2.59 |
| 24 | Q-2.60 |

(I.2)

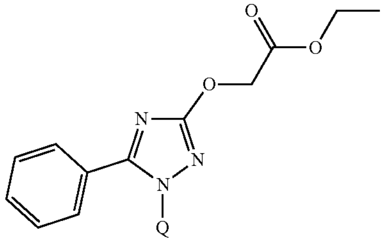

Table I.2: Preferred compounds of the formula (I.2) are the compounds I.2-1 to I.2-24 in which Q has the meanings from table 1 indicated in the respective row. Thus, the compounds I.2-1 to I.2-24 of table I.2 are defined by the meaning of the respective entry nos. 1 to 24 for Q from table 1.

(I.3)

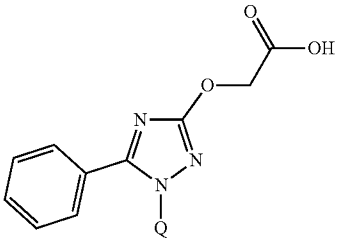

Table I.3: Preferred compounds of the formula (I.3) are the compounds I.3-1 to I.3-24 in which Q has the meanings from table 1 indicated in the respective row. Thus, the compounds I.3-1 to I.3-24 of table I.3 are defined by the meaning of the respective entry nos. 1 to 24 for Q from table 1.

(I.4)

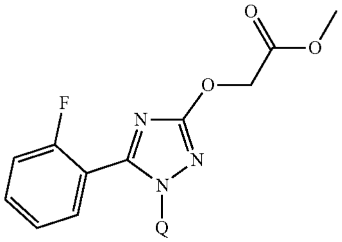

Table I.4: Preferred compounds of the formula (I.4) are the compounds I.4-1 to I.4-24 in which Q has the meanings from table 1 indicated in the respective row. Thus, the compounds I.4-1 to I.4-24 of table I.4 are defined by the meaning of the respective entry nos. 1 to 24 for Q from table 1.

(I.5)

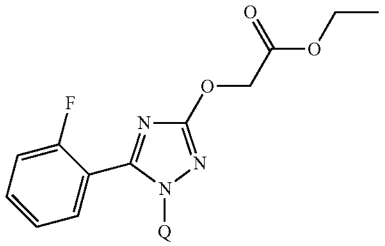

Table I.5: Preferred compounds of the formula (I.5) are the compounds I.5-1 to I.5-24 in which Q has the meanings from table 1 indicated in the respective row. Thus, the compounds I.5-1 to I.5-24 of table I.5 are defined by the meaning of the respective entry nos. 1 to 24 for Q from table 1.

(I.6)

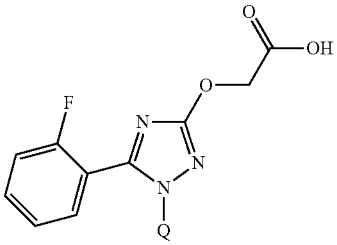

Table I.6: Preferred compounds of the formula (I.6) are the compounds I.6-1 to I.6-24 in which Q has the meanings from table 1 indicated in the respective row. Thus, the compounds I.6-1 to I.6-24 of table I.6 are defined by the meaning of the respective entry nos. 1 to 24 for Q from table 1.

(I.7)

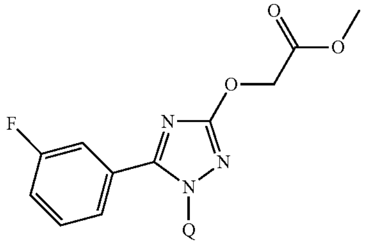

Table I.7: Preferred compounds of the formula (I.7) are the compounds I.7-1 to I.7-24 in which Q has the meanings from table 1 indicated in the respective row. Thus, the compounds I.7-1 to I.7-24 of table I.7 are defined by the meaning of the respective entry nos. 1 to 24 for Q from table 1.

(I.8)

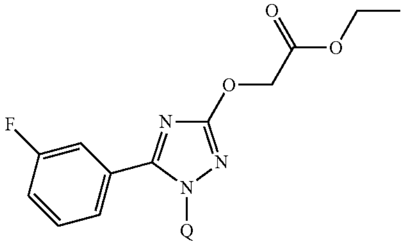

Table I.8: Preferred compounds of the formula (I.8) are the compounds I.8-1 to I.8-24 in which Q has the meanings from table 1 indicated in the respective row. Thus, the compounds I.8-1 to I.8-24 of table I.8 are defined by the meaning of the respective entry nos. 1 to 24 for Q from table 1.

(I.9)

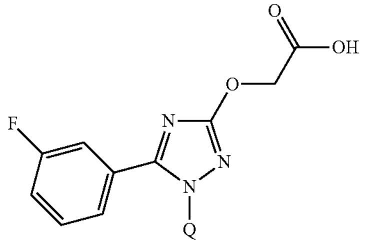

Table I.9: Preferred compounds of the formula (I.9) are the compounds I.9-1 to I.9-24 in which Q has the meanings from table 1 indicated in the respective row. Thus, the compounds I.9-1 to I.9-24 of table I.9 are defined by the meaning of the respective entry nos. 1 to 24 for Q from table 1.

(I.10)

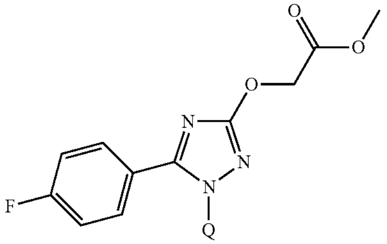

Table I.10: Preferred compounds of the formula (I.10) are the compounds I.10-1 to I.10-24 in which Q has the meanings from table 1 indicated in the respective row. Thus, the compounds I.10-1 to I.10-24 of table I.10 are defined by the meaning of the respective entry nos. 1 to 24 for Q from table 1.

(I.11)

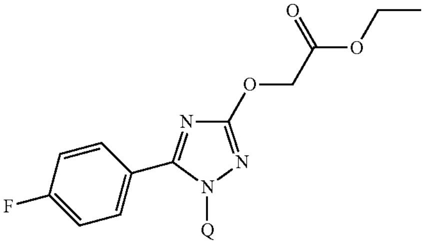

Table I.11: Preferred compounds of the formula (I.11) are the compounds I.11-1 to I.11-24 in which Q has the meanings from table 1 indicated in the respective row. Thus, the compounds I.11-1 to I.11-24 of table I.11 are defined by the meaning of the respective entry nos. 1 to 24 for Q from table 1.

(I.12)

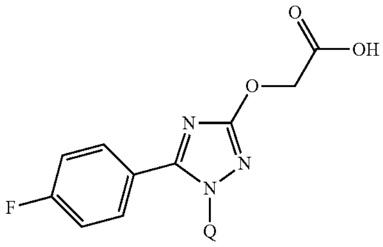

Table I.12: Preferred compounds of the formula (I.12) are the compounds I.12-1 to I.12-24 in which Q has the meanings from table 1 indicated in the respective row. Thus, the compounds I.12-1 to I.12-24 of (I.13)

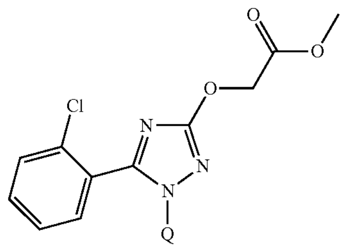

Table I.13: Preferred compounds of the formula (I.13) are the compounds I.13-1 to I.13-24 in which Q has the meanings from table 1 indicated in the respective row. Thus, the compounds I.13-1 to I.13-24 of table I.13 are defined by the meaning of the respective entry nos. 1 to 24 for Q from table 1.

(I.14)

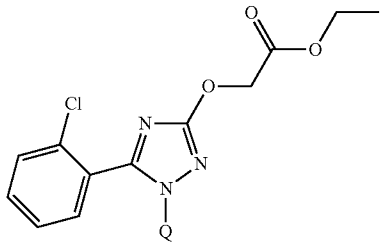

Table I.14: Preferred compounds of the formula (I.14) are the compounds I.14-1 to I.14-24 in which Q has the meanings from table 1 indicated in the respective row. Thus, the compounds I.14-1 to I.14-24 of table I.14 are defined by the meaning of the respective entry nos. 1 to 24 for Q from table 1.

(I.15)

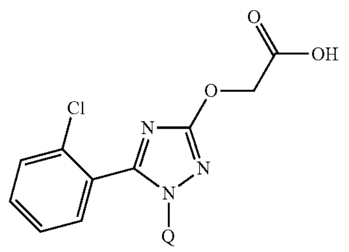

Table I.15: Preferred compounds of the formula (I.15) are the compounds I.15-1 to I.15-24 in which Q has the meanings from table 1 indicated in the respective row. Thus, the compounds I.15-1 to I.15-24 of (I.16)

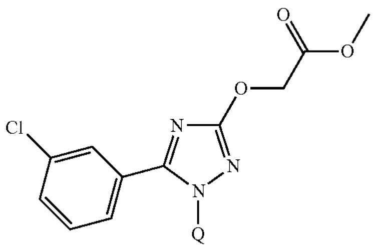

Table I.16: Preferred compounds of the formula (I.16) are the compounds I.16-1 to I.16-24 in which Q has the meanings from table 1 indicated in the respective row. Thus, the compounds I.16-1 to I.16-24 of table I.16 are defined by the meaning of the respective entry nos. 1 to 24 for Q from table 1.

(I.17)

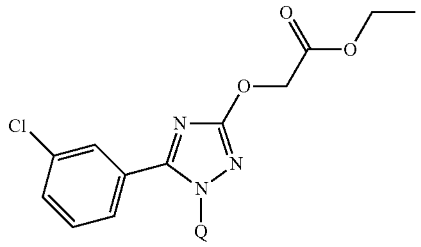

Table I.17: Preferred compounds of the formula (I.17) are the compounds I.17-1 to I.17-24 in which Q has the meanings from table 1 indicated in the respective row. Thus, the compounds I.17-1 to I.17-24 of table I.17 are defined by the meaning of the respective entry nos. 1 to 24 for Q from table 1.

(I.18)

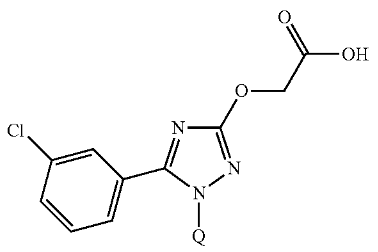

Table I.18: Preferred compounds of the formula (I.18) are the compounds I.18-1 to I.18-24 in which Q has the meanings from table 1 indicated in the respective row. Thus, the compounds I.18-1 to I.18-24 of

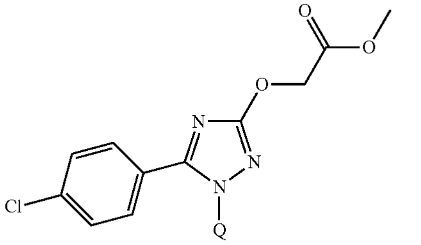

(I.19)

Table I.19: Preferred compounds of the formula (I.19) are the compounds I.19-1 to I.19-24 in which Q has the meanings from table 1 indicated in the respective row. Thus, the compounds I.19-1 to I.19-24 of table I.19 are defined by the meaning of the respective entry nos. 1 to 24 for Q from table 1.

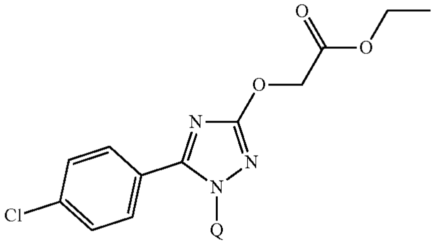

(I.20)

Table I.20: Preferred compounds of the formula (I.20) are the compounds I.20-1 to I.20-24 in which Q has the meanings from table 1 indicated in the respective row. Thus, the compounds I.20-1 to I.20-24 of table I.20 are defined by the meaning of the respective entry nos. 1 to 24 for Q from table 1.

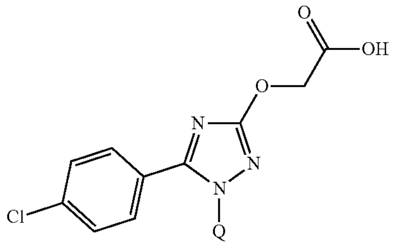

(I.21)

Table I.21: Preferred compounds of the formula (I.21) are the compounds I.21-1 to I.21-24 in which Q has the meanings from table 1 indicated in the respective row. Thus, the compounds I.21-1 to I.21-24 of

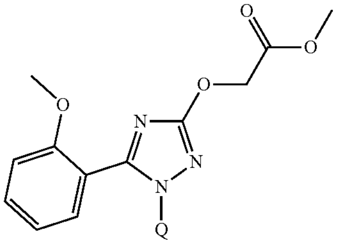

(I.22)

Table I.22: Preferred compounds of the formula (I.22) are the compounds I.22-1 to I.22-24 in which Q has the meanings from table 1 indicated in the respective row. Thus, the compounds I.22-1 to I.22-24 of table I.22 are defined by the meaning of the respective entry nos. 1 to 24 for Q from table 1.

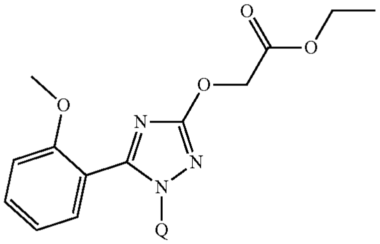

(I.23)

Table I.23: Preferred compounds of the formula (I.23) are the compounds I.23-1 to I.23-24 in which Q has the meanings from table 1 indicated in the respective row. Thus, the compounds I.23-1 to I.23-24 of table I.23 are defined by the meaning of the respective entry nos. 1 to 22 for Q from table 1.

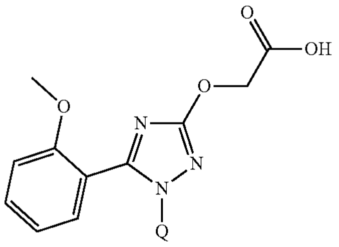

(I.24)

Table I.24: Preferred compounds of the formula (I.24) are the compounds I.24-1 to I.24-24 in which Q has the meanings from table 1 indicated in the respective row. Thus, the compounds I.24-1 to I.24-24 of (I.25)

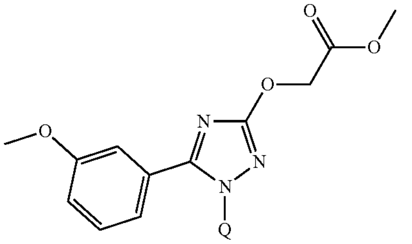

Table I.25: Preferred compounds of the formula (I.25) are the compounds I.25-1 to I.25-24 in which Q has the meanings from table 1 indicated in the respective row. Thus, the compounds I.25-1 to I.25-24 of table I.25 are defined by the meaning of the respective entry nos. 1 to 24 for Q from table 1.

(I.26)

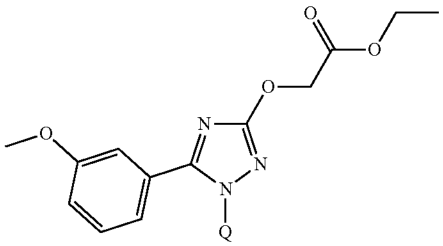

Table I.26: Preferred compounds of the formula (I.26) are the compounds I.26-1 to I.26-24 in which Q has the meanings from table 1 indicated in the respective row. Thus, the compounds I.26-1 to I.26-24 of table I.26 are defined by the meaning of the respective entry nos. 1 to 24 for Q from table 1.

(I.27)

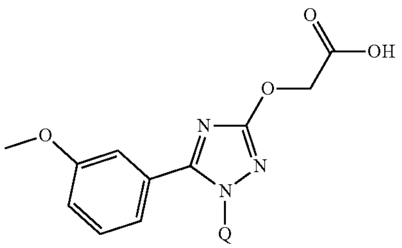

Table I.27: Preferred compounds of the formula (I.27) are the compounds I.27-1 to I.27-24 in which Q has the meanings from table 1 indicated in the respective row. Thus, the compounds I.27-1 to I.27-24 of (I.28)

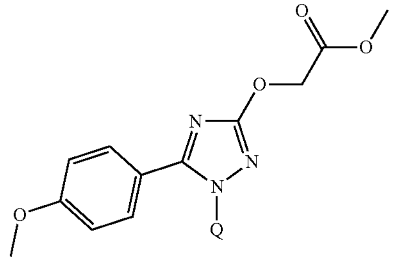

Table I.28: Preferred compounds of the formula (I.28) are the compounds I.28-1 to I.28-24 in which Q has the meanings from table 1 indicated in the respective row. Thus, the compounds I.28-1 to I.28-24 of table I.28 are defined by the meaning of the respective entry nos. 1 to 24 for Q from table 1.

(I.29)

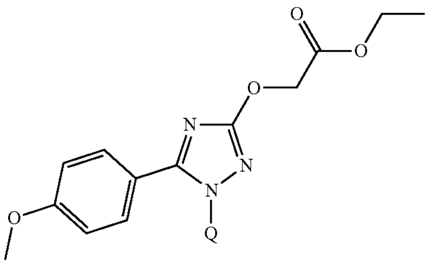

Table I.29: Preferred compounds of the formula (I.29) are the compounds I.29-1 to I.29-24 in which Q has the meanings from table 1 indicated in the respective row. Thus, the compounds I.29-1 to I.29-24 of table I.29 are defined by the meaning of the respective entry nos. 1 to 24 for Q from table 1.

(I.30)

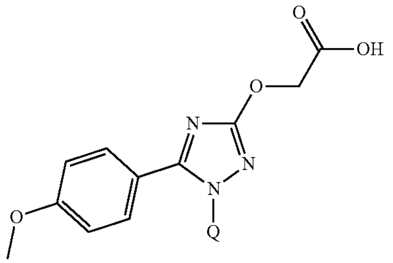

Table I.30: Preferred compounds of the formula (I.30) are the compounds I.30-1 to I.30-24 in which Q has the meanings from table 1 indicated in the respective row. Thus, the compounds I.30-1 to I.30-24 of (I.31)

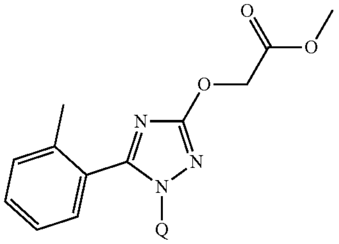

Table I.31: Preferred compounds of the formula (I.31) are the compounds I.31-1 to I.31-24 in which Q has the meanings from table 1 indicated in the respective row. Thus, the compounds I.31-1 to I.31-24 of table I.31 are defined by the meaning of the respective entry nos. 1 to 24 for Q from table 1.

(I.32)

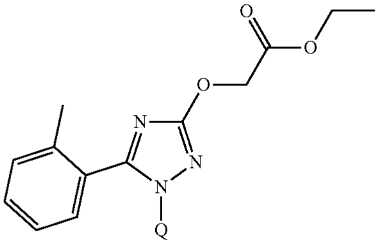

Table I.32: Preferred compounds of the formula (I.32) are the compounds I.32-1 to I.32-24 in which Q has the meanings from table 1 indicated in the respective row. Thus, the compounds I.32-1 to I.32-24 of table I.32 are defined by the meaning of the respective entry nos. 1 to 24 for Q from table 1.

(I.33)

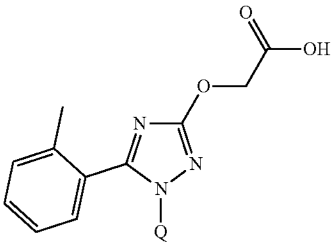

Table I.33: Preferred compounds of the formula (I.33) are the compounds I.33-1 to I.33-24 in which Q has the meanings from table 1 indicated in the respective row. Thus, the compounds I.33-1 to I.33-24 of (I.34)

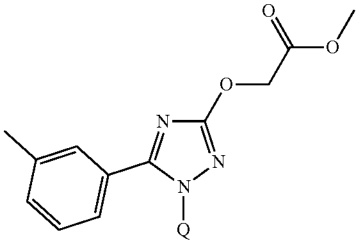

Table I.34: Preferred compounds of the formula (I.34) are the compounds I.34-1 to I.34-24 in which Q has the meanings from table 1 indicated in the respective row. Thus, the compounds I.34-1 to I.34-24 of table I.34 are defined by the meaning of the respective entry nos. 1 to 24 for Q from table 1.

(I.35)

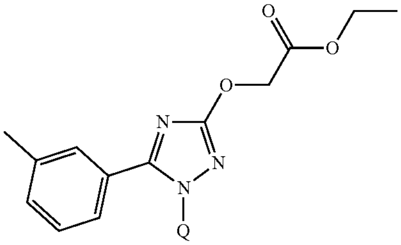

Table I.35: Preferred compounds of the formula (I.35) are the compounds I.35-1 to I.35-24 in which Q has the meanings from table 1 indicated in the respective row. Thus, the compounds I.35-1 to I.35-24 of table I.35 are defined by the meaning of the respective entry nos. 1 to 24 for Q from table 1.

(I.36)

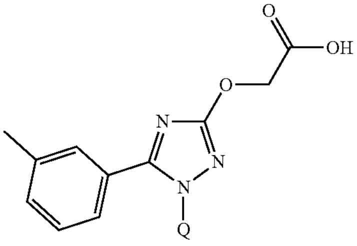

Table I.36: Preferred compounds of the formula (I.36) are the compounds I.36-1 to I.36-24 in which Q has the meanings from table 1 indicated in the respective row. Thus, the compounds I.36-1 to I.36-24 of

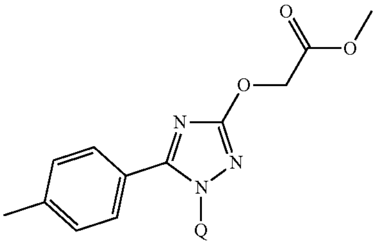

(I.37)

Table I.37: Preferred compounds of the formula (I.37) are the compounds I.37-1 to I.37-24 in which Q has the meanings from table 1 indicated in the respective row. Thus, the compounds I.37-1 to I.37-24 of table I.37 are defined by the meaning of the respective entry nos. 1 to 24 for Q from table 1.

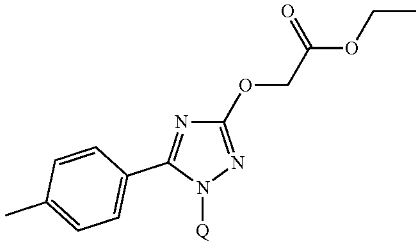

(I.38)

Table I.38: Preferred compounds of the formula (I.38) are the compounds I.38-1 to I.38-24 in which Q has the meanings from table 1 indicated in the respective row. Thus, the compounds I.38-1 to I.38-24 of table I.38 are defined by the meaning of the respective entry nos. 1 to 24 for Q from table 1.

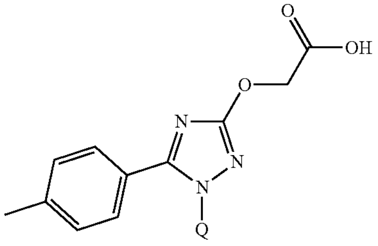

(I.39)

Table I.39: Preferred compounds of the formula (I.39) are the compounds I.39-1 to I.39-24 in which Q has the meanings from table 1 indicated in the respective row. Thus, the compounds I.39-1 to I.39-24 of

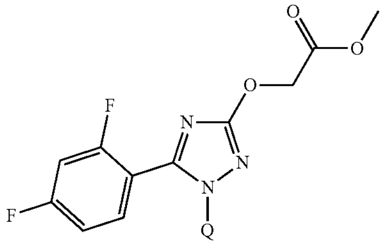

(I.40)

Table I.40: Preferred compounds of the formula (I.40) are the compounds I.40-1 to I.40-24 in which Q has the meanings from table 1 indicated in the respective row. Thus, the compounds I.40-1 to I.40-24 of table I.40 are defined by the meaning of the respective entry nos. 1 to 24 for Q from table 1.

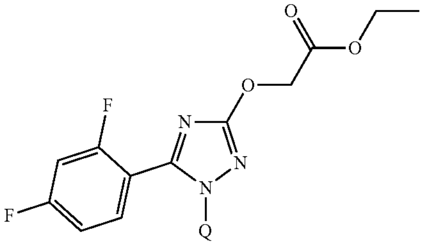

(I.41)

Table I.41: Preferred compounds of the formula (I.41) are the compounds I.41-1 to I.41-24 in which Q has the meanings from table 1 indicated in the respective row. Thus, the compounds I.41-1 to I.41-24 of table I.41 are defined by the meaning of the respective entry nos. 1 to 24 for Q from table 1.

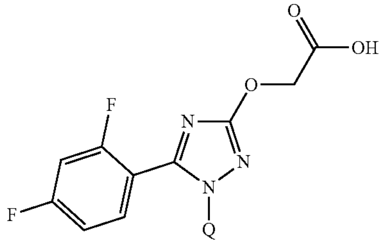

(I.42)

Table I.42: Preferred compounds of the formula (I.42) are the compounds I.42-1 to I.42-24 in which Q has the meanings from table 1 indicated in the respective row. Thus, the compounds I.42-1 to I.42-24 of (I.43)

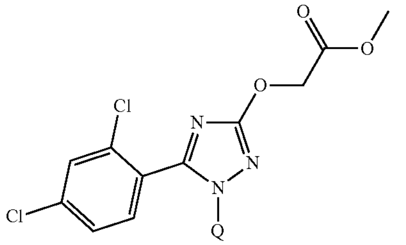

Table I.43: Preferred compounds of the formula (I.4) are the compounds I.43-1 to I.43-24 in which Q has the meanings from table 1 indicated in the respective row. Thus, the compounds I.43-1 to I.43-24 of table 1.43 are defined by the meaning of the respective entry nos. 1 to 24 for Q from table 1.

(I.44)

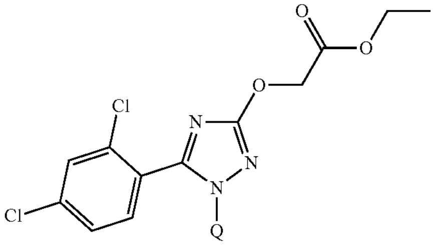

Table I.44: Preferred compounds of the formula (I.44) are the compounds I.44-1 to I.44-24 in which Q has the meanings from table 1 indicated in the respective row. Thus, the compounds I.44-1 to I.44-24 of table I.44 are defined by the meaning of the respective entry nos. 1 to 24 for Q from table 1.

(I.45)

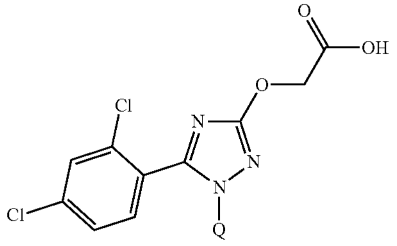

Table I.45: Preferred compounds of the formula (I.45) are the compounds I.45-1 to I.45-24 in which Q has the meanings from table 1 indicated in the respective row. Thus, the compounds I.45-1 to I.45-24 of (I.46)

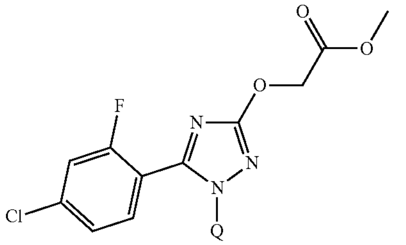

Table I.46: Preferred compounds of the formula (I.46) are the compounds I.46-1 to I.46-24 in which Q has the meanings from table 1 indicated in the respective row. Thus, the compounds I.46-1 to I.46-24 of table I.46 are defined by the meaning of the respective entry nos. 1 to 24 for Q from table 1.

(I.47)

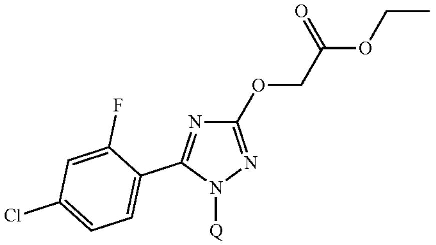

Table I.47: Preferred compounds of the formula (I.47) are the compounds I.47-1 to I.47-24 in which Q has the meanings from table 1 indicated in the respective row. Thus, the compounds I.47-1 to I.47-24 of table I.47 are defined by the meaning of the respective entry nos. 1 to 24 for Q from table 1.

(I.48)

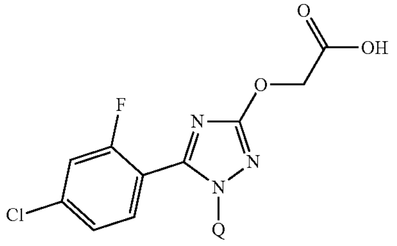

Table I.48: Preferred compounds of the formula (I.48) are the compounds I.48-1 to I.48-24 in which Q has the meanings from table 1 indicated in the respective row. Thus, the compounds I.48-1 to I.48-24 of (I.49)

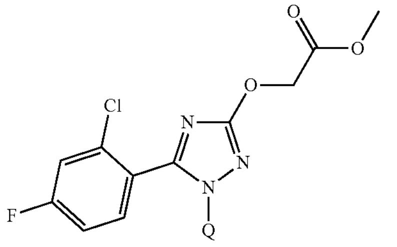

Table I.49: Preferred compounds of the formula (I.49) are the compounds I.49-1 to I.49-24 in which Q has the meanings from table 1 indicated in the respective row. Thus, the compounds I.49-1 to I.49-24 of table I.49 are defined by the meaning of the respective entry nos. 1 to 24 for Q from table 1.

(I.50)

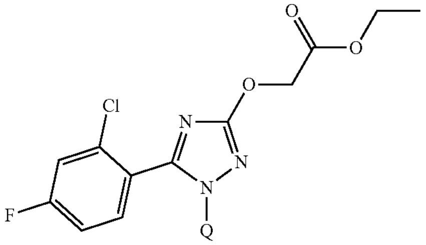

Table I.50: Preferred compounds of the formula (I.50) are the compounds I.50-1 to I.50-24 in which Q has the meanings from table 1 indicated in the respective row. Thus, the compounds I.50-1 to I.50-24 of table I.50 are defined by the meaning of the respective entry nos. 1 to 24 for Q from table 1.

(I.51)

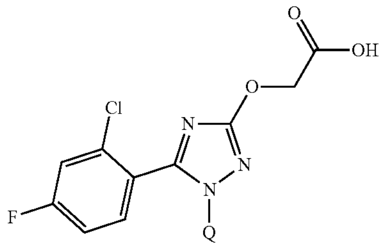

Table I.51: Preferred compounds of the formula (I.51) are the compounds I.51-1 to I.51-24 in which Q has the meanings from table 1 indicated in the respective row. Thus, the compounds I.51-1 to I.51-24 of (I.52)

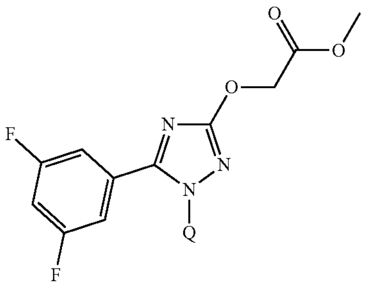

Table I.52: Preferred compounds of the formula (I.52) are the compounds I.52-1 to I.52-24 in which Q has the meanings from table 1 indicated in the respective row. Thus, the compounds I.52-1 to I.52-24 of table I.52 are defined by the meaning of the respective entry nos. 1 to 24 for Q from table 1.

(I.53)

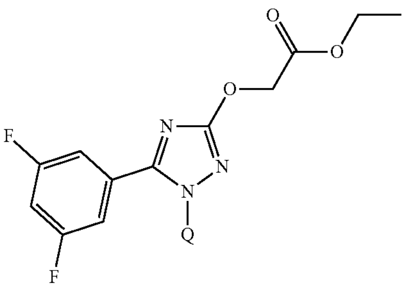

Table I.53: Preferred compounds of the formula (I.53) are the compounds I.53-1 to I.53-24 in which Q has the meanings from table 1 indicated in the respective row. Thus, the compounds I.53-1 to I.53-24 of table I.53 are defined by the meaning of the respective entry nos. 1 to 24 for Q from table 1.

(I.54)

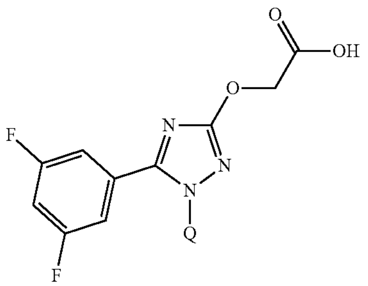

Table I.54: Preferred compounds of the formula (I.54) are the compounds I.54-1 to I.54-24 in which Q has the meanings from table 1 indicated in the respective row. Thus, the compounds I.54-1 to I.54-24 of (I.55)

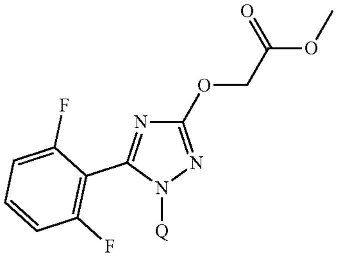

Table I.55: Preferred compounds of the formula (I.55) are the compounds I.55-1 to I.55-24 in which Q has the meanings from table 1 indicated in the respective row. Thus, the compounds I.55-1 to I.55-24 of table I.55 are defined by the meaning of the respective entry nos. 1 to 24 for Q from table 1.

(I.56)

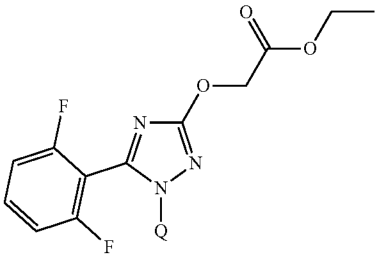

Table I.56: Preferred compounds of the formula (I.56) are the compounds I.56-1 to I.56-24 in which Q has the meanings from table 1 indicated in the respective row. Thus, the compounds I.56-1 to I.56-24 of table I.56 are defined by the meaning of the respective entry nos. 1 to 24 for Q from table 1.

(I.57)

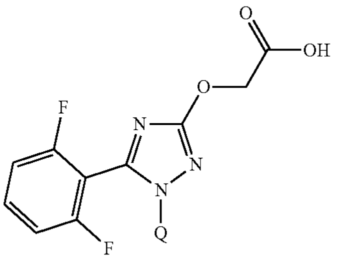

Table I.57: Preferred compounds of the formula (I.57) are the compounds I.57-1 to I.57-24 in which Q has the meanings from table 1 indicated in the respective row. Thus, the compounds I.57-1 to I.57-24 of (I.58)

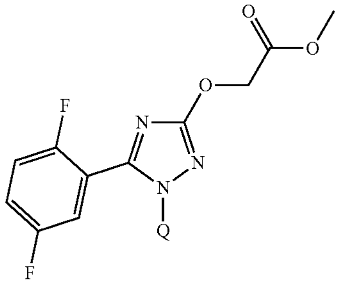

Table I.58: Preferred compounds of the formula (I.58) are the compounds I.58-1 to I.58-24 in which Q has the meanings from table 1 indicated in the respective row. Thus, the compounds I.58-1 to I.58-24 of table I.58 are defined by the meaning of the respective entry nos. 1 to 24 for Q from table 1.

(I.59)

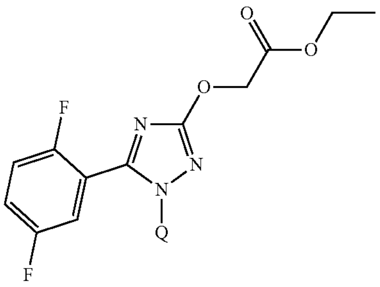

Table I.59: Preferred compounds of the formula (I.59) are the compounds I.59-1 to I.59-24 in which Q has the meanings from table 1 indicated in the respective row. Thus, the compounds I.59-1 to I.59-24 of table I.59 are defined by the meaning of the respective entry nos. 1 to 24 for Q from table 1.

(I.60)

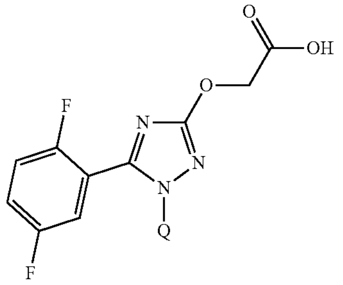

Table I.60: Preferred compounds of the formula (I.60) are the compounds I.60-1 to I.60-24 in which Q has the meanings from table 1 indicated in the respective row. Thus, the compounds I.60-1 to I.60-24 of (I.61)

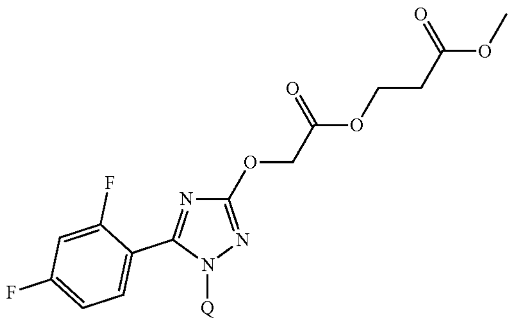

Table I.61: Preferred compounds of the formula (I.61) are the compounds I.61-1 to I.61-24 in which Q has the meanings from table 1 indicated in the respective row. Thus, the compounds I.61-1 to I.61-24 of table I.61 are defined by the meaning of the respective entry nos. 1 to 24 for Q from table 1.

(I.62)

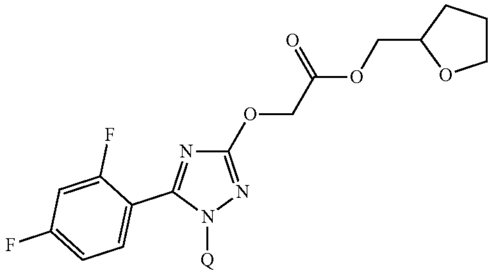

Table I.62: Preferred compounds of the formula (I.62) are the compounds I.62-1 to I.62-24 in which Q has the meanings from table 1 indicated in the respective row. Thus, the compounds I.62-1 to I.62-24 of table I.62 are defined by the meaning of the respective entry nos. 1 to 24 for Q from table 1.

(I.63)

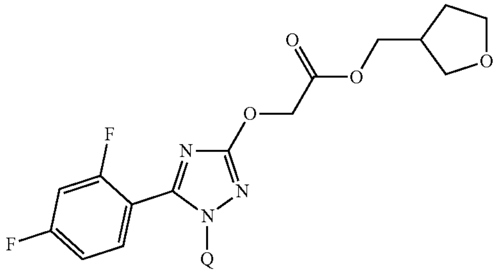

Table I.63: Preferred compounds of the formula (I.63) are the compounds I.63-1 to I.63-24 in which Q has the meanings from table 1 indicated in the respective row. Thus, the compounds I.63-1 to I.63-24 of table I.63 are defined by the meaning of the respective entry nos. 1 to 24 for Q from table 1.

(I.64)

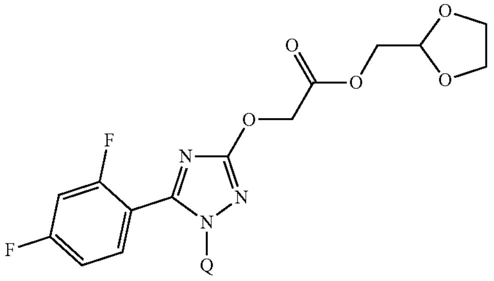

Table I.64: Preferred compounds of the formula (I.64) are the compounds I.64-1 to I.64-24 in which Q has the meanings from table 1 indicated in the respective row. Thus, the compounds I.64-1 to I.64-24 of table I.64 are defined by the meaning of the respective entry nos. 1 to 24 for Q from table 1.

(I.65)

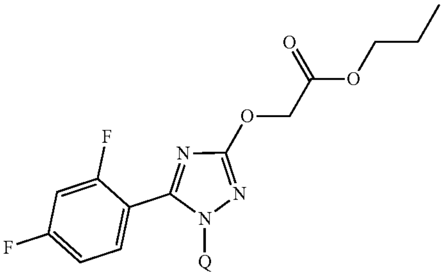

Table I.65: Preferred compounds of the formula (I.65) are the compounds I.65-1 to I.65-24 in which Q has the meanings from table 1 indicated in the respective row. Thus, the compounds I.65-1 to I.65-24 of table I.65 are defined by the meaning of the respective entry nos. 1 to 24 for Q from table 1.

(I.66)

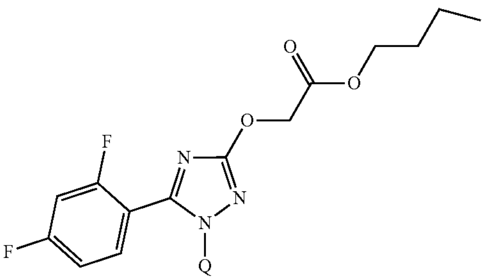

Table I.66: Preferred compounds of the formula (I.66) are the compounds I.66-1 to I.66-24 in which Q has the meanings from table 1 indicated in the respective row. Thus, the compounds I.66-1 to I.66-24 of (I.67)

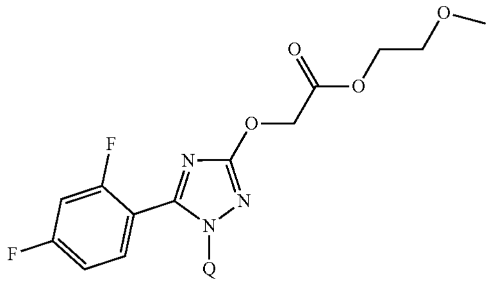

Table I.67: Preferred compounds of the formula (I.67) are the compounds I.67-1 to I.67-24 in which Q has the meanings from table 1 indicated in the respective row. Thus, the compounds I.67-1 to I.67-24 of table I.67 are defined by the meaning of the respective entry nos. 1 to 24 for Q from table 1.

(I.68)

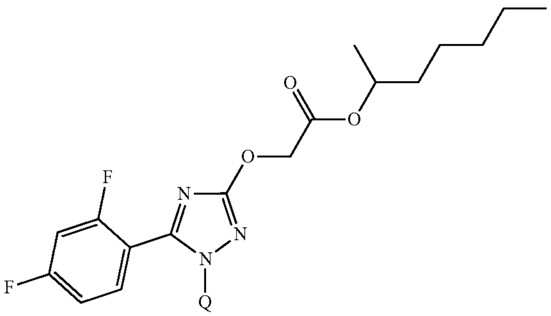

Table I.68: Preferred compounds of the formula (I.68) are the compounds I.68-1 to I.68-24 in which Q has the meanings from table 1 indicated in the respective row. Thus, the compounds I.68-1 to I.68-24 of table I.68 are defined by the meaning of the respective entry nos. 1 to 24 for Q from table 1.

(I.69)

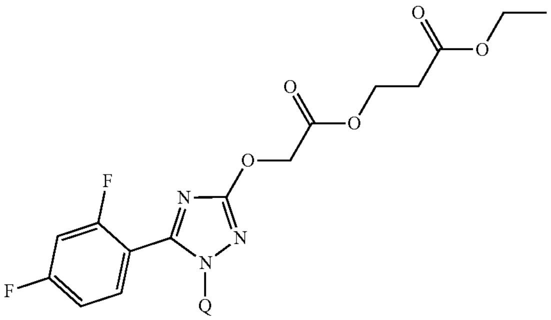

Table I.69: Preferred compounds of the formula (I.69) are the compounds I.69-1 to I.69-24 in which Q has the meanings from table 1 indicated in the respective row. Thus, the compounds I.69-1 to I.69-24 of (I.70)

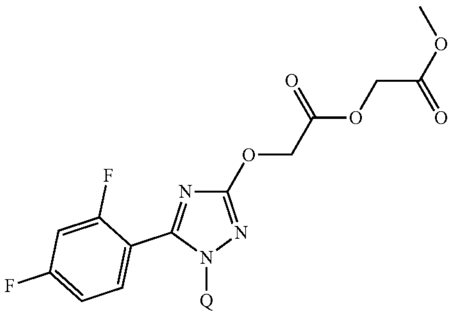

Table I.70: Preferred compounds of the formula (I.70) are the compounds I.70-1 to I.70-24 in which Q has the meanings from table 1 indicated in the respective row. Thus, the compounds I.70-1 to I.70-24 of table I.70 are defined by the meaning of the respective entry nos. 1 to 24 for Q from table 1.

(I.71)

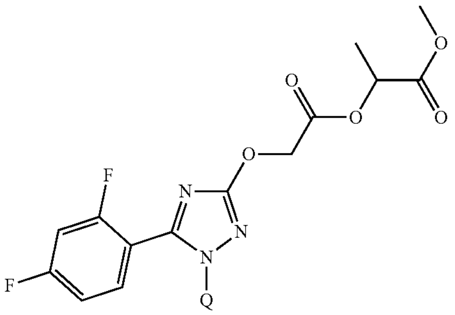

Table I.71: Preferred compounds of the formula (I.71) are the compounds I.71-1 to I.71-24 in which Q has the meanings from table 1 indicated in the respective row. Thus, the compounds I.71-1 to I.71-24 of table I.71 are defined by the meaning of the respective entry nos. 1 to 24 for Q from table 1.

(I.72)

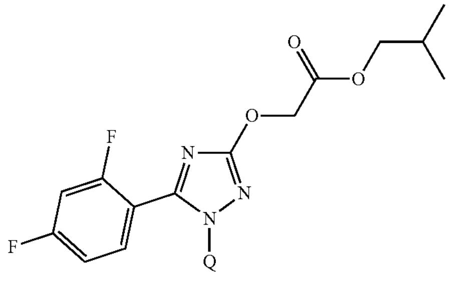

Table I.72: Preferred compounds of the formula (I.72) are the compounds I.72-1 to I.72-24 in which Q has the meanings from table 1 indicated in the respective row. Thus, the compounds I.72-1 to I.72-24 of table I.72 are defined by the meaning of the respective entry nos. 1 to 24 for Q from table 1.

(I.73)

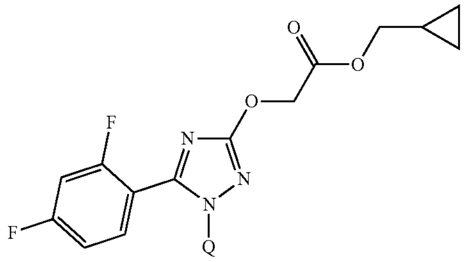

Table I.73: Preferred compounds of the formula (I.73) are the compounds I.73-1 to I.73-24 in which Q has the meanings from table 1 indicated in the respective row. Thus, the compounds I.73-1 to I.73-24 of table I.73 are defined by the meaning of the respective entry nos. 1 to 24 for Q from table 1.

(I.74)

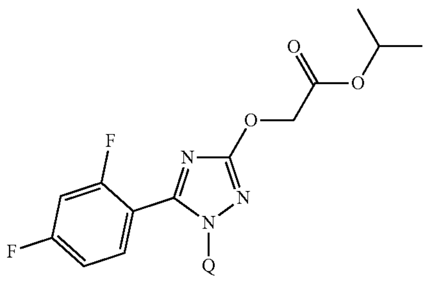

Table I.74: Preferred compounds of the formula (I.74) are the compounds I.74-1 to I.74-24 in which Q has the meanings from table 1 indicated in the respective row. Thus, the compounds I.74-1 to I.74-24 of table I.74 are defined by the meaning of the respective entry nos. 1 to 24 for Q from table 1.

(I.75)

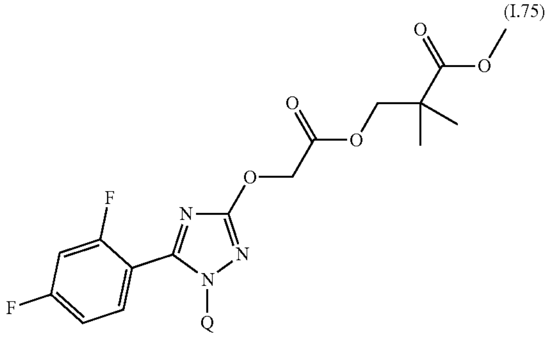

Table I.75: Preferred compounds of the formula (I.75) are the compounds I.75-1 to I.75-24 in which Q has the meanings from table 1 indicated in the respective row. Thus, the compounds I.75-1 to I.75-24 of table I.75 are defined by the meaning of the respective entry nos. 1 to 24 for Q from table 1.

(I.76)

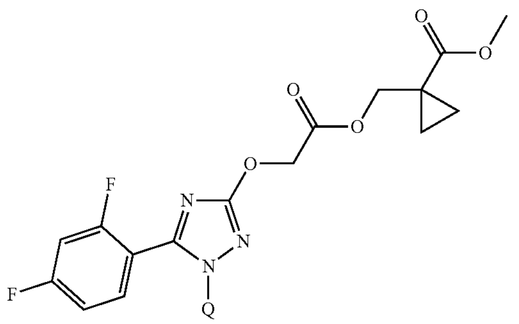

Table I.76: Preferred compounds of the formula (I.76) are the compounds I.76-1 to I.76-24 in which Q has the meanings from table 1 indicated in the respective row. Thus, the compounds I.76-1 to I.76-24 of table I.76 are defined by the meaning of the respective entry nos. 1 to 24 for Q from table 1.

(I.77)

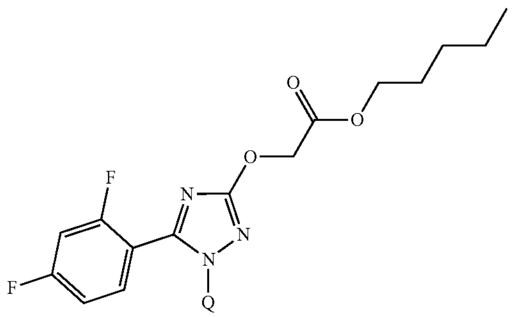

Table I.77: Preferred compounds of the formula (I.77) are the compounds I.77-1 to I.77-24 in which Q has the meanings from table 1 indicated in the respective row. Thus, the compounds I.77-1 to I.77-24 of table I.77 are defined by the meaning of the respective entry nos. 1 to 24 for Q from table 1.

Spectroscopic data of selected table examples:

Selected detailed synthesis examples for the inventive compounds of the general formula (I) are adduced below. The $^{1}H$ NMR, $^{13}C$-NMR and $^{19}F$-NMR spectroscopy data reported for the chemical examples described in the sections which follow (400 MHz for $^{1}H$ NMR and 150 MHz for $^{13}C$-NMR and 375 MHz for $^{19}F$-NMR, solvent $CDCl_3$, $CD_3OD$ or $d_6$-DMSO, internal standard: tetramethylsilane $\delta$=0.00 ppm) were obtained on a Bruker instrument, and the signals listed have the meanings given below: br=broad; s=singlet, d=doublet, t=triplet, dd=doublet of doublets, ddd=doublet of a doublet of doublets, m=multiplet, q=quartet, quint=quintet, sext=sextet, sept=septet, dq=doublet of quartets, dt=doublet of triplets. In the case of diastereomer mixtures, either the significant signals for each of the two diastereomers are reported or the characteristic signal of the main diastereomer is reported. The abbreviations used for chemical groups have, for example, the following meanings: Me=$CH_3$, Et=$CH_2CH_3$, t-Hex=$C(CH_3)_2CH(CH_3)_2$, t-Bu=$C(CH_3)_3$, n-Bu=unbranched butyl, n-Pr=unbranched propyl, i-Pr=branched propyl, c-Pr=cyclopropyl, c-Hex=cyclohexyl.

The spectroscopic data listed hereinafter for selected table examples were evaluated via conventional $^1$H NMR interpretation or via NMR peak list methods.

Conventional $^1$H NMR Interpretation

Example No. I.48-23

$^1$H-NMR (400 MHz, DMSO-$d_6$ δ, ppm) 13.13 (bs, 1H), 8.57 (m, 1H), 8.19 (dd, 1H), 7.64-7.54 (m, 3H), 7.43 (dd, 1H), 4.87 (s, 2H).

Example No. I.40-10

$^1$H-NMR (400 MHz, $CDCl_3$ δ, ppm) 8.12 (d, 1H), 7.80 (dd, 1H), 7.72 (dd, 1H), 7.68 (m, 1H), 7.01 (m, 1H), 6.79 (m, 1H), 4.97 (s, 2H), 3.82 (s, 3H).

Example No. I.41-9

$^1$H-NMR (400 MHz, $CDCl_3$ δ, ppm) 8.09 (d, 1H), 7.80 (dd, 1H), 7.66 (m, 1H), 7.07-6.98 (m, 2H), 6.83-6.78 (m, 2H), 4.93 (s, 2H), 4.28 (q, 2H), 1.30 (t, 3H).

Example No. I.48-11

$^1$H-NMR (400 MHz, $CDCl_3$ δ, ppm) 8.29 (d, 1H), 7.69-7.60 (m, 2H), 7.39 (dd, 1H), 7.31 (m, 1H), 7.10 (m, 1H), 4.98 (s, 2H).

Example No. I.40-11

$^1$H-NMR (400 MHz, $CDCl_3$ δ, ppm) 8.03 (d, 1H), 7.77-7.68 (m, 2H), 7.55 (m, 1H), 7.01 (m, 1H), 6.77 (m, 1H), 4.97 (s, 2H), 3.82 (s, 3H).

Example No. I.46-23

$^1$H-NMR (400 MHz, $CDCl_3$ δ, ppm) 8.48 (d, 1H), 7.83 (dd, 1H), 7.58 (m, 1H), 7.38 (m, 1H), 7.23 (m, 1H), 7.02 (dd, 1H), 4.95 (s, 2H), 3.81 (s, 3H).

Example No. I.42-9

$^1$H-NMR (400 MHz, DMSO-$d_6$ δ, ppm) 13.12 (bs, 1H), 8.27 (d, 1H), 8.04 (m, 1H), 7.72 (m, 1H), 7.43-7.27 (m, 3H), 4.88 (s, 2H).

Example No. I.48-10

$^1$H-NMR (400 MHz, DMSO-$d_6$ δ, ppm) 13.17 (bs, 1H), 8.36 (d, 1H), 8.18 (dd, 1H), 7.78 (d, 1H), 7.69 (m, 1H), 7.56 (m, 1H), 7.46 (m, 1H), 4.91 (s, 2H).

Example No. I.49-9

$^1$H-NMR (400 MHz, $CDCl_3$ δ, ppm) 8.09 (d, 1H), 7.82 (m, 1H), 7.62 (m, 1H), 7.29 (m, 1H), 7.08 (m, 1H), 7.00 (m, 1H), 4.95 (s, 2H), 3.82 (s, 3H).

Example No. I.42-23

$^1$H-NMR (400 MHz, DMSO-$d_6$ δ, ppm) 13.11 (bs, 1H), 8.56 (dd, 1H), 8.19 (dd, 1H), 7.66-7.60 (m, 2H), 7.38 (m, 1H), 7.23 (m, 1H), 4.86 (s, 2H).

Example No. I.46-10

$^1$H-NMR (400 MHz, $CDCl_3$ δ, ppm) 8.12 (d, 1H), 7.80 (dd, 1H), 7.72 (dd, 1H), 7.63 (dd, 1H), 7.28 (dd, 1H), 7.07 (dd, 1H), 4.97 (s, 2H), 3.82 (s, 3H).

Example No. I.47-9

$^1$H-NMR (400 MHz, $CDCl_3$ δ, ppm) 8.09 (d, 1H), 7.81 (m, 1H), 7.61 (m, 1H), 7.30 (m, 1H), 7.10 (dd, 1H), 7.00 (m, 1H), 4.93 (s, 2H), 4.28 (q, 2H), 1.30 (t, 3H).

Example No. I.48-9

$^1$H-NMR (400 MHz, DMSO-$d_6$ δ, ppm) 13.12 (bs, 1H), 8.28 (d, 1H), 8.06 (m, 1H), 7.66 (m, 1H), 7.59 (m, 1H), 7.49 (m, 1H), 7.34 (m, 1H), 4.86 (s, 2H).

Example No. I.40-21

$^1$H-NMR (400 MHz, $CDCl_3$ δ, ppm) 8.48 (m, 1H), 7.83 (m, 1H), 7.62 (m, 1H), 7.38 (m, 1H), 6.97 (m, 1H), 6.73 (m, 1H), 4.95 (s, 2H), 3.81 (s, 3H).

Example No. I.46-8

$^1$H-NMR (400 MHz, $CDCl_3$ δ, ppm) 8.26 (d, 1H), 7.68-7.60 (m, 2H), 7.38 (d, 1H), 7.31 (dd, 1H), 7.10 (dd, 1H), 4.95 (s, 2H), 3.82 (s, 3H).

NMR Peak List Method

The 1H NMR data of selected examples are noted in the form of 1H NMR peak lists. For each signal peak, first the δ value in ppm and then the signal intensity in round brackets are listed. The δ value/signal intensity number pairs for different signal peaks are listed with separation from one another by semicolons.

The peak list for one example therefore takes the form of:

$\delta_1$ (intensity$_1$); $\delta_2$ (intensity$_2$); . . . ; $\delta_i$ (intensity$_i$); . . . ; $\delta_n$ (intensity$_n$)

The intensity of sharp signals correlates with the height of the signals in a printed example of an NMR spectrum in cm and shows the true ratios of the signal intensities. In the case of broad signals, several peaks or the middle of the signal and the relative intensity thereof may be shown in comparison to the most intense signal in the spectrum.

For calibration of the chemical shift of $^1$H NMR spectra, we use tetramethylsilane and/or the chemical shift of the solvent, particularly in the case of spectra which are measured in DMSO. Therefore, the tetramethylsilane peak may but need not occur in NMR peak lists.

The lists of the $^1$H NMR peaks are similar to the conventional $^1$H NMR printouts and thus usually contain all peaks listed in a conventional NMR interpretation.

In addition, like conventional $^1$H NMR printouts, they may show solvent signals, signals of stereoisomers of the target compounds which are likewise provided by the invention, and/or peaks of impurities.

In the reporting of compound signals within the delta range of solvents and/or water, our lists of $^1$H NMR peaks show the standard solvent peaks, for example peaks of DMSO in DMSO-$D_6$ and the peak of water, which usually have a high intensity on average.

The peaks of stereoisomers of the target compounds and/or peaks of impurities usually have a lower intensity on average than the peaks of the target compounds (for example with a purity of >90%).

Such stereoisomers and/or impurities may be typical of the particular preparation process. Their peaks can thus help in identifying reproduction of our preparation process with reference to "by-product fingerprints".

An expert calculating the peaks of the target compounds by known methods (MestreC, ACD simulation, but also with empirically evaluated expected values) can, if required, isolate the peaks of the target compounds, optionally using additional intensity filters. This isolation would be similar to the relevant peak picking in conventional 1H NMR interpretation.

Further details of $^1$H NMR peak lists can be found in the Research disclosure Database Number 564025.

I.57-22: $^1$H-NMR(300.1 MHz, $d_6$-DMSO):

δ = 12.3937 (0.5); 9.2480 (5.6); 9.2263 (5.8); 8.4325 (0.7); 8.2959 (5.3); 8.2734 (5.8); 8.2539 (0.6); 7.7257 (0.5); 7.7012 (0.8); 7.6745 (1.9); 7.6510 (3.3); 7.6256 (2.6); 7.6039 (1.1); 7.4338 (0.7); 7.4088 (2.8); 7.3830 (3.7); 7.3710 (3.5); 7.3463 (4.7); 7.3331 (6.9); 7.3008 (13.9); 7.2743 (12.3); 7.2615 (6.5); 7.2363 (5.4); 7.1221 (1.4); 7.0973 (3.3); 7.0747 (4.5); 7.0606 (4.3); 6.9997 (3.1); 6.9759 (5.5); 6.9531 (11.4); 6.9243 (15.5); 6.8958 (7.8); 6.8719 (3.2); 6.8488 (3.8); 6.8250 (2.4); 6.7449 (0.5); 6.6061 (0.4); 4.5766 (0.5); 4.3590 (0.4); 4.3133 (0.5); 4.3021 (0.5); 4.2682 (0.5); 4.2449 (0.5); 4.1884 (0.9); 4.1153 (10.9); 4.0355 (1.2); 3.9754 (16.0); 3.8965 (1.3); 3.8294 (0.8); 3.7693 (0.8); 3.7405 (1.0); 3.6499 (1.2); 3.3287 (243.7); 3.2142 (2.7); 3.1688 (2.0); 3.1235 (1.6); 3.0996 (1.4); 3.0795 (1.3); 3.0277 (1.3); 2.9926 (1.2); 2.9734 (1.2); 2.9586 (1.2); 2.9448 (1.2); 2.8896 (1.4); 2.8544 (1.5); 2.7986 (1.8); 2.7262 (4.2); 2.5006 (396.1); 2.3887 (1.9); 2.3477 (1.6); 2.2709 (3.0); 2.2167 (0.9); 2.1786 (0.9); 2.1672 (0.8); 2.1355 (0.8); 2.0914 (0.6); 2.0438 (0.6); 2.0169 (0.5); 2.0011 (0.5); 1.9738 (0.6); 1.9628 (0.6); 1.9550 (0.5); 1.8867 (2.4); 1.8221 (0.6); 1.7825 (0.6); 1.7660 (0.6); 1.7548 (0.5); 1.7160 (0.4); 1.7029 (0.4); 1.6921 (0.4); 1.6808 (0.4); 1.6412 (0.4); 1.6176 (0.4); 1.5901 (0.5); 1.5781 (0.4); 1.5286 (0.4); 1.4249 (0.5); 1.3681 (0.4); 1.2931 (0.4); 1.2532 (0.5); 1.2432 (0.7); 1.2358 (1.0); 1.2249 (0.7); 1.2129 (0.5); 1.1445 (2.1); 1.0718 (0.6); 1.0553 (0.6); 1.0466 (0.6); 1.0248 (0.5); 1.0054 (0.6); 0.9782 (0.6); 0.8976 (0.4); 0.8874 (0.4); 0.7967 (0.4); 0.5598 (0.4); −0.0016 (2.3); −3.5425 (0.4); −3.5753 (0.4)

I.40-2: $^1$H-NMR(400.6 MHz, $CDCl_3$):

δ = 8.6034 (0.8); 8.5998 (0.8); 8.5914 (0.8); 8.5878 (0.8); 8.5092 (1.1); 8.5033 (1.1); 7.7098 (0.7); 7.7060 (0.8); 7.7034 (0.8); 7.6995 (0.8); 7.6893 (0.9); 7.6855 (0.9); 7.6828 (1.4); 7.6789 (1.1); 7.6668 (0.7); 7.6612 (0.8); 7.6476 (0.9); 7.6448 (0.9); 7.6410 (0.6); 7.6254 (0.6); 7.3752 (0.8); 7.3734 (0.8); 7.3632 (0.8); 7.3614 (0.8); 7.3547 (0.8); 7.3529 (0.8); 7.3426 (0.7); 7.3409 (0.7); 7.2636 (27.7); 7.0318 (0.7); 7.0291 (0.5); 7.0283 (0.5); 7.0257 (0.8); 6.8196 (0.6); 6.8135 (0.5); 6.7981 (0.6); 6.7944 (0.6); 6.7922 (0.6); 6.7885 (0.6); 6.7731 (0.6); 6.7670 (0.5); 4.9602 (8.3); 3.8212 (16.0); 3.8141 (0.6); 1.6095 (2.2); 1.2845 (0.6); 1.2549 (1.2); −0.0002 (9.0)

I.40-22: $^1$H-NMR(300.1 MHz, $d_6$-DMSO):

δ = 8.3804 (2.2); 8.3572 (2.2); 7.4826 (0.7); 7.4540 (1.5); 7.4327 (1.7); 7.4097 (1.7); 7.3854 (1.6); 7.3743 (1.4); 7.3484 (1.5); 7.2151 (0.9); 7.2071 (0.9); 7.1763 (1.5); 7.1500 (1.9); 7.1360 (1.7); 7.1259 (2.0); 7.1116 (2.0); 7.1023 (1.2); 7.0875 (1.0); 7.0362 (0.8); 7.0134 (1.5); 6.9853 (0.8); 4.7327 (8.8); 3.7436 (16.0); 3.5869 (0.7); 3.3314 (9.3); 3.3078 (2.5); 2.5079 (27.4); 2.5020 (35.7); 2.4963 (25.7); 2.0763 (0.5); 1.2331 (0.5); −0.0008 (7.2)

I.4-22: $^1$H-NMR(300.1 MHz, $d_6$-DMSO):

δ = 8.3870 (2.0); 8.3640 (2.2); 8.1362 (0.5); 7.4120 (0.4); 7.3875 (1.7); 7.3632 (3.0); 7.3485 (2.9); 7.3423 (3.3); 7.3250 (2.4); 7.3179 (2.1); 7.1396 (1.0); 7.1248 (1.3); 7.1156 (1.7); 7.0974 (3.2); 7.0687 (3.8); 7.0428 (1.3); 7.0366 (1.1); 4.7834 (0.4); 4.7432 (6.0); 4.6890 (0.5); 3.7489 (16.0); 3.6957 (0.5); 3.6890 (0.6); 3.5712 (0.7); 3.3364 (24.5); 2.5147 (2.4); 2.5090 (4.7); 2.5031 (6.3); 2.4973 (4.5); 2.0764 (11.3); −0.0004 (0.6)

I.1-22: $^1$H-NMR(300.1 MHz, $d_6$-DMSO):

δ = 8.2143 (2.1); 8.2128 (2.1); 8.1906 (2.3); 8.1713 (2.3); 8.1669 (2.9); 8.1619 (1.3); 8.1511 (0.9); 8.1444 (3.2); 8.1390 (2.3); 7.5503 (0.5); 7.5455 (0.4); 7.5366 (0.4); 7.5262 (1.7); 7.5177 (1.6); 7.5077 (1.1); 7.5026 (1.8); 7.4947 (1.5); 7.4797 (2.8); 7.4773 (2.8); 7.4575 (2.6); 7.4529 (3.4); 7.4352 (0.5); 7.4297 (1.1); 7.4244 (0.6); 7.3891 (0.4); 6.9748 (0.8); 6.9597 (0.8); 6.9502 (1.2); 6.9353 (1.2); 6.9257 (0.7); 6.9105 (0.6); 5.3890 (7.1); 4.9956 (0.6); 3.7465 (0.3); 3.7381 (0.4); 3.7123 (1.5); 3.6764 (16.0); 3.6508 (0.4); 3.6465 (0.3); 3.6304 (0.4); 3.6212 (0.3); 3.6048 (0.8); 3.5927 (0.6); 3.5795 (0.3); 3.5685 (0.4); 3.4657 (0.3); 3.4558 (0.3); 3.3719 (457.6); 3.3123 (0.4); 2.5167 (10.1); 2.5108 (19.6); 2.5049 (26.1); 2.4989 (17.9); 2.4931 (8.1); 2.0750 (3.2); 1.2337 (0.4); −0.0002 (1.0)

I.55-22: $^1$H-NMR(300.1 MHz, $d_6$-DMSO):

δ = 8.4406 (1.9); 8.4178 (2.0); 7.4413 (0.5); 7.4211 (1.8); 7.4138 (1.2); 7.3969 (2.5); 7.3909 (2.3); 7.3866 (2.2); 7.3686 (1.6); 7.3615 (2.2); 7.3413 (0.6); 7.1839 (1.0); 7.1691 (1.2); 7.1601 (1.5); 7.1455 (1.4); 7.1359 (0.9); 7.1212 (0.7); 7.0351 (1.5); 7.0062 (2.5); 6.9776 (1.3); 4.7845 (8.4); 4.7386 (0.8); 3.7663 (16.0); 3.5637 (1.6); 3.3356 (8.8); 2.5033 (5.0); 2.0768 (3.1)

I.46-22: $^1$H-NMR(400.2 MHz, $d_6$-DMSO):

δ = 8.3930 (2.1); 8.3758 (2.2); 7.4213 (1.4); 7.4129 (1.4); 7.4012 (2.6); 7.3924 (2.8); 7.3865 (3.0); 7.3665 (2.9); 7.2298 (1.8); 7.2254 (1.8); 7.2090 (1.5); 7.2046 (1.4); 7.1551 (0.8); 7.1441 (1.0); 7.1371 (1.4); 7.1263 (1.5); 7.1191 (0.9); 7.1081 (0.8); 4.7367 (8.3); 3.7466 (16.0); 3.5891 (0.8); 3.3351 (41.4); 3.3114 (3.9); 2.5117 (7.8); 2.5074 (15.7); 2.5030 (21.0); 2.4985 (15.0); 2.4942 (7.1); 2.0772 (0.5); 1.7541 (0.6); 0.0001 (2.0)

I.6-22: $^1$H-NMR(300.1 MHz, $d_6$-DMSO):

δ = 13.2965 (0.3); 13.2071 (0.4); 13.1912 (0.4); 13.1600 (0.4); 13.1177 (0.3); 8.4117 (6.7); 8.3888 (6.9); 8.1553 (0.4); 8.1316 (0.4); 8.0424 (0.7); 8.0223 (0.9); 7.9896 (0.4); 7.8715 (0.4); 7.8651 (0.5); 7.7451 (0.4); 7.7227 (0.7); 7.6997 (0.6); 7.6776 (0.7); 7.6545 (0.8); 7.6292 (0.6); 7.5240 (0.3); 7.4980 (0.4); 7.4734 (0.6); 7.4300 (1.3); 7.4094 (1.4); 7.3741 (6.0); 7.3496 (12.5); 7.3364 (8.4); 7.3293 (11.4); 7.3117 (7.3); 7.3044 (8.1); 7.2766 (1.0); 7.2640 (0.5); 7.2554 (0.4); 7.2384 (0.5); 7.2167 (0.4); 7.1287 (3.5); 7.1138 (4.4); 7.1047 (6.0); 7.0879 (10.9); 7.0581 (12.8); 7.0319 (4.5); 7.0270 (4.2); 6.9585 (0.3); 5.2560 (1.0); 4.6150 (16.0); 4.5420 (2.2); 3.3229 (7.7); 3.1461 (0.4); 2.7339 (0.5); 2.7280 (0.7); 2.7220 (0.5); 2.5138 (45.6); 2.5079 (87.7); 2.5020 (115.5); 2.4960 (79.8); 2.4903 (37.1); 2.2780 (0.5); 2.2716 (0.7); 2.2660 (0.5); 2.0743 (5.8); 1.2351 (0.6); 1.1470 (0.4); 0.0109 (0.4); −0.0002 (9.2)

I.40-11: $^1$H-NMR(400.6 MHz, $d_6$-DMSO):

δ = 8.3202 (3.0); 8.3127 (3.1); 8.0327 (1.1); 8.0252 (1.0); 8.0123 (1.3); 8.0103 (1.5); 8.0048 (1.2); 8.0028 (1.4); 7.9900 (1.4); 7.9825 (1.2); 7.8209 (1.7); 7.8111 (1.8); 7.7986 (1.4); 7.7976 (1.4); 7.7887 (1.4); 7.7878 (1.3); 7.7499 (0.7); 7.7338 (0.8); 7.7287 (1.3); 7.7126 (1.4); 7.7076 (0.9); 7.6915 (0.8); 7.3892 (0.7); 7.3830 (0.8); 7.3659 (0.9); 7.3624 (1.0); 7.3599 (1.0); 7.3564 (0.9); 7.3393 (0.8); 7.3331 (0.8); 7.2783 (0.6); 7.2763 (0.6); 7.2704 (0.6); 7.2567 (1.1); 7.2554 (1.2); 7.2500 (1.1); 7.2358 (0.6); 7.2338 (0.6); 7.2292 (0.5); 5.7575 (16.0); 4.9056 (10.5); 2.5135 (5.3); 2.5089 (11.6); 2.5043 (16.2); 2.4998 (11.2); 2.4952 (5.0); −0.0002 (10.3)

I.47-5: $^1$H-NMR(400.6 MHz, $CDCl_3$):

δ = 9.1884 (6.7); 8.7235 (16.0); 7.6796 (1.5); 7.6606 (1.7); 7.6589 (1.9); 7.6400 (1.7); 7.3488 (1.3); 7.3471 (1.2); 7.3438 (1.3); 7.3423 (1.3); 7.3279 (1.1); 7.3263 (1.1); 7.3230 (1.2); 7.3215 (1.1); 7.2630 (10.4); 7.1320 (1.6); 7.1271 (1.5); 7.1075 (1.6); 7.1027 (1.5); 5.3008 (0.8); 4.9398 (12.2); 4.3160 (1.6); 4.2982 (5.0); 4.2804 (5.0); 4.2626 (1.6); 1.5749 (2.4); 1.3281 (6.3); 1.3104 (13.2); 1.2925 (6.2); 0.0697 (1.8); −0.0002 (15.4)

-continued

I.46-11: $^1$H-NMR(400.6 MHz, $CDCl_3$):
δ = 8.0396 (1.7); 8.0387 (1.6); 8.0323 (1.8); 8.0313 (1.7); 7.7751 (0.8); 7.7741 (0.8); 7.7654 (0.9); 7.7642 (0.8); 7.7528 (1.0); 7.7517 (0.9); 7.7431 (1.1); 7.7420 (0.9); 7.6672 (1.1); 7.6482 (1.3); 7.6467 (1.4); 7.6277 (1.2); 7.5878 (0.8); 7.5804 (0.8); 7.5691 (0.9); 7.5654 (0.7); 7.5618 (0.8); 7.5581 (0.7); 7.5468 (0.7); 7.5395 (0.6); 7.2864 (1.0); 7.2848 (0.9); 7.2814 (1.0); 7.2800 (0.9); 7.2654 (1.0); 7.2630 (3.8); 7.2607 (1.0); 7.2592 (0.9); 7.0668 (1.2); 7.0619 (1.2); 7.0422 (1.2); 7.0373 (1.2); 5.2997 (2.4); 4.9649 (8.5); 3.8160 (16.0); 0.0710 (3.8); −0.0002 (5.1)

I.47-20: $^1$H-NMR(400.6 MHz, $CDCl_3$):
δ = 8.1450 (1.6); 8.1309 (1.6); 8.1242 (1.6); 8.1101 (1.6); 7.6508 (1.8); 7.6319 (2.1); 7.6303 (2.4); 7.6114 (2.1); 7.5353 (1.6); 7.5296 (1.7); 7.5116 (1.7); 7.5058 (1.6); 7.2862 (1.5); 7.2846 (1.5); 7.2813 (1.6); 7.2798 (1.6); 7.2654 (1.6); 7.2623 (20.4); 7.0814 (2.0); 7.0765 (1.9); 7.0570 (2.0); 7.0522 (1.9); 6.9806 (1.2); 6.9748 (1.2); 6.9665 (1.2); 6.9609 (2.3); 6.9553 (1.2); 6.9470 (1.3); 6.9412 (1.1); 5.2999 (5.4); 4.9454 (15.3); 4.3166 (1.9); 4.2988 (6.1); 4.2810 (6.2); 4.2631 (2.0); 1.3240 (7.9); 1.3199 (0.6); 1.3062 (16.0); 1.3021 (1.1); 1.2884 (7.6); 1.2842 (0.7); 0.0704 (1.5); −0.0002 (12.4)

I.47-11: $^1$H-NMR(400.6 MHz, $CDCl_3$):
δ = 8.0374 (2.8); 8.0363 (2.7); 8.0300 (3.0); 8.0290 (2.7); 7.7756 (1.4); 7.7744 (1.2); 7.7658 (1.4); 7.7647 (1.3); 7.7533 (1.7); 7.7520 (1.6); 7.7435 (1.7); 7.7424 (1.5); 7.6641 (1.8); 7.6450 (2.2); 7.6435 (2.3); 7.6245 (2.0); 7.5853 (1.4); 7.5780 (1.3); 7.5666 (1.5); 7.5630 (1.2); 7.5593 (1.4); 7.5556 (1.1); 7.5444 (1.2); 7.5370 (1.1); 7.2851 (1.6); 7.2834 (1.5); 7.2801 (1.6); 7.2786 (1.5); 7.2627 (7.8); 7.2594 (1.6); 7.2579 (1.4); 7.0665 (1.9); 7.0616 (1.8); 7.0419 (1.9); 7.0371 (1.8); 5.2998 (5.8); 4.9406 (14.7); 4.3092 (1.9); 4.2913 (5.9); 4.2735 (6.0); 4.2557 (2.0); 1.5851 (1.0); 1.3163 (7.7); 1.2984 (16.0); 1.2806 (7.5); 0.0706 (3.5); −0.0002 (9.7)

I.46-5: $^1$H-NMR(400.6 MHz, $CDCl_3$):
δ = 9.1908 (4.7); 8.7253 (11.4); 7.6824 (1.1); 7.6633 (1.3); 7.6617 (1.4); 7.6427 (1.3); 7.3500 (1.0); 7.3484 (0.9); 7.3451 (1.0); 7.3436 (0.9); 7.3292 (0.8); 7.3275 (0.8); 7.3242 (0.9); 7.3227 (0.8); 7.2627 (9.0); 7.1324 (1.2); 7.1276 (1.1); 7.1079 (1.2); 7.1031 (1.1); 5.3007 (2.3); 4.9638 (8.3); 3.8259 (16.0); 1.5736 (1.0); 1.2596 (0.8); 0.8819 (1.0); 0.0697 (1.2); −0.0002 (13.0); −0.0028 (0.5)

I.48-5: $^1$H-NMR(400.6 MHz, $d_6$-DMSO):
δ = 9.2544 (7.2); 8.9046 (16.0); 7.7240 (1.0); 7.7034 (1.7); 7.6835 (1.3); 7.6384 (1.1); 7.6335 (1.2); 7.6128 (1.1); 7.6079 (1.2); 7.5129 (1.1); 7.5116 (1.1); 7.5073 (1.1); 7.4919 (0.9); 7.4906 (0.9); 7.4864 (0.9); 4.9102 (6.6); 3.3234 (1.3); 2.5201 (0.5); 2.5113 (7.8); 2.5068 (17.2); 2.5022 (24.2); 2.4976 (16.6); 2.4930 (7.3); 2.1834 (0.6); 1.3558 (5.8); −0.0002 (18.4); −0.0085 (0.5)

I.48-11: $^1$H-NMR(400.6 MHz, $d_6$-DMSO):
δ = 8.3326 (3.0); 8.3251 (3.1); 8.0378 (1.1); 8.0303 (1.0); 8.0175 (1.3); 8.0154 (1.5); 8.0100 (1.1); 8.0079 (1.4); 7.9952 (1.4); 7.9876 (1.2); 7.8281 (1.6); 7.8272 (1.6); 7.8183 (1.8); 7.8058 (1.4); 7.8047 (1.4); 7.7959 (1.4); 7.7949 (1.3); 7.7071 (1.6); 7.6867 (2.7); 7.6669 (1.9); 7.5692 (1.7); 7.5642 (1.8); 7.5437 (1.7); 7.5387 (1.9); 7.4705 (1.7); 7.4694 (1.8); 7.4648 (1.7); 7.4498 (1.4); 7.4486 (1.5); 7.4441 (1.4); 5.7572 (16.0); 4.9061 (10.1); 3.3248 (0.8); 2.5252 (0.6); 2.5206 (0.8); 2.5118 (10.1); 2.5073 (22.2); 2.5027 (31.1); 2.4981 (21.4); 2.4935 (9.4); 0.0080 (0.6); −0.0002 (23.2); −0.0085 (0.7)

The invention also provides the method of protecting crop plants or useful plants from phytotoxic effects of agrochemicals, such as pesticides, or herbicides in particular, which cause damage to the crop plants or useful plants, characterized in that compounds of the general formula (I) or salts thereof are employed as safeners, preference being given to applying an effective amount of the compounds of the general formula (I) or salts thereof to the plants, parts of plants or seeds (or seed material) thereof.

The compounds of the general formula (I) safeners) as specified above are suitable for use together with active ingredients (pesticides) for selective control of harmful organisms in a number of crop cultures, for example in economically important crops such as cereal (wheat, barley, triticale, rye, rice, maize, millet/sorghum), sugar beet, sugar cane, oilseed rape, cotton, sunflower, peas, beans and soya.

The herbicide-safener combinations with safeners of the general formula (I) are also suitable for control of harmful plants on beds and areas of useful plants and ornamental plants, for example lawn areas with utility lawns or decorative lawns, specifically ryegrass, bluegrass or bermuda grass.

Also of interest in respect of the useful plants and crop plants in which the herbicide-safener combinations comprising the aforementioned compounds of the general formula (I) can be used are mutant crops that are wholly or partially tolerant or transgenic crops that are wholly or partially tolerant to some pesticides, for example maize crops resistant to glufosinate or glyphosate, or soya crops that are resistant to imidazolinones that have a plant-damaging effect.

However, the particular benefit of the safeners of the general formula (I) used in a novel manner is their effective action in crops that are not normally sufficiently tolerant to the pesticides to be employed.

For common use with pesticides, the compounds of the general formula (I) can be deployed simultaneously or in any sequence with the active ingredients, and are then capable of reducing or entirely preventing damaging side effects of these active ingredients in the case of crop plants without impairing or significantly reducing the efficacy of these active ingredients with respect to unwanted harmful organisms.

It is also possible here to significantly reduce or entirely prevent damage resulting from the use of more than one pesticide, for example by more than one herbicide or by herbicides in combination with insecticides or fungicides.

This can quite considerably extend the field of use of conventional pesticides.

If the compositions of the invention contain pesticides, these compositions, at appropriate dilution, are applied either directly to the growing area, to the already germinated harmful plants and/or useful plants, or to the already emerged harmful plants and/or useful plants.

If the compositions of the invention do not contain any pesticide, these compositions may be used by what is called the tankmix method, meaning that the user mixes and dilutes the separately formulated products (=useful plant-protecting composition and pesticide) immediately prior to application to the area to be treated, or before the application of a pesticide, or after the application of a pesticide, or for seed pretreatment, i.e., for example, for dressing of the useful plant seed.

Preference is given to prompt application of the safener with the pesticide, especially when the safener is applied to the plants after the herbicide.

The advantageous effects of the compounds of the general formula (I) are observed when they are used together with the pesticides by the pre-emergence or post-emergence method, for example in the case of simultaneous application as a tankmix or as a co-formulation or in a separate application in parallel or successively (split application). It is also possible to repeat the application more than once. It can sometimes also be sensible to combine a pre-emergence application with a post-emergence application. One option is usually employment as post-emergence application to the useful plant or crop plant with simultaneous or later application of the pesticide. Another option is to employ the inventive compounds (I) in seed dressing, (dip) treatment of seedlings (e.g. rice) or treatment of other propagation material (e.g. potato tubers).

When the compounds of the general formula (I) are employed in combination with herbicides, it is often the case that not only the safener effect but also boosts in herbicidal action against harmful plants are observed. Moreover, the growth of the useful plants and crop plants is improved in many cases, and it is possible to increase the harvest yields.

The compositions of the invention may contain one or more pesticides. Examples of useful pesticides include herbicides, insecticides, fungicides, acaricides and nematicides which, when employed alone, would each result in phytotoxic damage to the crop plants or where damage would be likely.

Of particular interest are the corresponding active pesticidal ingredients from the group of the herbicides, insecticides, acaricides, nematicides and fungicides, especially herbicides.

The weight ratio of safeners (of the general formula (I)) to pesticide may be varied within wide limits and is generally in the range from 1:100 to 100:1, preferably 1:20 to 20:1, especially 1:10 to 10:1. The optimal weight ratio of safener to pesticide depends both on the respective safener used and the respective pesticide and on the type of useful plant or crop plant to be protected. According to the pesticide used and type of useful plant to be protected, the required application rate of safener may be varied within wide limits and is generally in the range from 0.001 to 10 kg, preferably 0.01 to 1 kg, especially 0.01 to 0.2 kg, of safener per hectare. The amounts and weight ratios needed for a successful treatment can be ascertained by simple preliminary tests.

In the case of seed dressing, for example, 0.005 to 20 g of safener (of the general formula (I)) per kilogram of seed, preferably 0.01 to 10 g of safener per kilogram of seed, especially 0.05 to 5 g of safener per kilogram of seed, are used.

When solutions of safeners (of the general formula (I)) are utilized in seed treatment and the seed or seedlings are wetted with the solutions, the suitable concentration is generally in the range from 1 to 10 000 ppm, preferably 100 to 1000 ppm, based on weight.

The amounts and weight ratios needed for a successful treatment can be ascertained by simple preliminary tests.

The safeners of the general formula (I) can be formulated in a customary manner, separately or together with the pesticides.

Also provided, therefore, are the useful plant- or crop plant-protecting compositions.

Preference is given to the joint use of safener and pesticide, especially that of safener and herbicide as a finished formulation or employment by the tankmix method.

Likewise preferred is the employment of the safener of the general formula (I) in seed treatment with later application of pesticides, preferably herbicides, after sowing by the pre- or post-emergence method.

The compounds of the general formula (I) or salts thereof can be used as such or in the form of their preparations (formulations) in a combination with other pesticidally active substances, for example insecticides, acaricides, nematicides, herbicides, fungicides, safeners, fertilizers and/or growth regulators, for example in the form of a finished formulation or of tank mixes.

The combination formulations can be produced on the basis of the abovementioned formulations, taking account of the physical properties and stabilities of the active ingredients to be combined.

Combination partners usable for the compounds of the invention in mixed formulations or in a tankmix are, for example, known active ingredients based on inhibition of, for example, acetolactate synthase, acetyl-CoA carboxylase, cellulose synthase, enolpyruvylshikimate-3-phosphate synthase, glutamine synthetase, p-hydroxyphenylpyruvate dioxygenase, phytoene desaturase, photosystem I, photosystem II or protoporphyrinogen oxidase, as known, for example, from Weed Research 26 (1986) 441-445 or "The Pesticide Manual", 16th edition, The British Crop Protection Council and the Royal Soc. of Chemistry, 2006, and literature cited therein.

Known herbicides or plant growth regulators which can be combined with the compounds of the invention are, for example, the following, where said active ingredients are referred to either by their "common name" in accordance with the International Organization for Standardization (ISO) or by the chemical name or by the code number. They always encompass all the use forms, for example acids, salts, esters and also all isomeric forms such as stereoisomers and optical isomers, even if they are not mentioned explicitly.

Examples of such herbicidal mixing partners are:

acetochlor, acifluorfen, acifluorfen-sodium, aclonifen, alachlor, allidochlor, alloxydim, alloxydim-sodium, ametryn, amicarbazone, amidochlor, amidosulfuron, 4-amino-3-chloro-6-(4-chloro-2-fluoro-3-methylphenyl)-5-fluoropyridine-2-carboxylic acid, aminocyclopyrachlor, aminocyclopyrachlor-potassium, aminocyclopyrachlor-methyl, aminopyralid, amitrole, ammoniumsulfamate, anilofos, asulam, atrazine, azafenidin, azimsulfuron, beflubutamid, benazolin, benazolin-ethyl, benfluralin, benfuresate, bensulfuron, bensulfuron-methyl, bensulide, bentazone, benzobicyclon, benzofenap, bicyclopyron, bifenox, bilanafos, bilanafos-sodium, bispyribac, bispyribac-sodium, bromacil, bromobutide, bromofenoxim, bromoxynil, bromoxynil-butyrate, -potassium, -heptanoate and -octanoate, busoxinone, butachlor, butafenacil, butamifos, butenachlor, butralin, butroxydim, butylate, cafenstrole, carbetamide, carfentrazone, carfentrazone-ethyl, chloramben, chlorbromuron, chlorfenac, chlorfenac-sodium, chlorfenprop, chlorflurenol, chlorflurenol-methyl, chloridazon, chlorimuron, chlorimuron-ethyl, chlorophthalim, chlorotoluron, chlorthal-dimethyl, chlorsulfuron, cinidon, cinidon-ethyl, cinmethylin, cinosulfuron, clacyfos, clethodim, clodinafop, clodinafop-propargyl, clomazone, clomeprop, clopyralid, cloransulam, cloransulam-methyl, cumyluron, cyanamide, cyanazine, cycloate, cyclopyrimorate, cyclosulfamuron, cycloxydim, cyhalofop, cyhalofop-butyl, cyprazine, 2,4-D, 2,4-D-butotyl, -butyl, -dimethylammonium, -diolamine, -ethyl, 2-ethylhexyl, -isobutyl, -isooctyl, -isopropylammonium, -potassium, -triisopropanolammonium and -trolamine, 2,4-DB, 2,4-DB-butyl, -dimethylammonium, isooctyl, -potassium and -sodium, daimuron (dymron), dalapon, dazomet, n-decanol, desmedipham, detosyl-pyrazolate (DTP), dicamba, dichlobenil, 2-(2,4-dichlorobenzyl)-4,4-dimethyl-1,2-oxazolidin-3-one, 2-(2,5-dichlorobenzyl)-4,4-dimethyl-1,2-oxazolidin-3-one, dichlorprop, dichlorprop-P, diclofop, diclofop-methyl, diclofop-P-methyl, diclosulam, difenzoquat, diflufenican, diflufenzopyr, diflufenzopyr-sodium, dimefuron, dimepiperate, dimethachlor, dimethametryn, dimethenamid, dimethenamid-P, dimetrasulfuron, dinitramine, dinoterb, diphenamid, diquat, diquat-dibromid, dithiopyr, diuron, DNOC, endothal, EPTC, esprocarb, ethalfluralin, ethametsulfuron, ethametsulfuron-methyl, ethiozin, ethofumesate, ethoxyfen, ethoxyfen-ethyl, ethoxysulfuron, etobenzanid, F-9600, F-5231, i.e. N-[2-chloro-4-fluoro-5-[4-(3-fluoropropyl)-4,5-dihydro-5-oxo-1H-tetrazol-1-yl]-phenyl]ethanesulfonamide, F-7967, i.e. 3-[7-chloro-5-fluoro-2-(trifluoromethyl)-1H-benzimidazol-4-yl]-1-methyl-6-(trifluoromethyl)pyrimidine-2,4(1H,3H)-dione, fenoxaprop, fenoxaprop-P, fenoxaprop-ethyl, fenoxaprop-P-ethyl, fenoxasulfone, fenquinotrione, fentrazamide, flamprop, flamprop-M-isopropyl, flamprop-M-methyl, flazasulfuron, florasulam, fluazifop, fluazifop-P, fluazifop-butyl, fluazifop-P-butyl, flucarbazone, flucarbazone-sodium, flucetosulfuron, fluchloralin, flufenacet, flufenpyr, flufenpyr-ethyl, flumetsulam, flumiclorac, flumiclorac-pentyl, flumioxazin, fluometuron, flurenol, flurenol-butyl, -dimethylammonium and -methyl, fluoroglycofen, fluoroglycofen-ethyl, flupropanate, flupyrsulfuron, flupyrsulfuron-methyl-sodium, fluridone, flurochloridone, fluroxypyr, fluroxypyr-meptyl, flurtamone, fluthiacet, fluthiacet-methyl, fomesafen, fomesafen-sodium, foramsulfuron, fosamine, glufosinate, glufosinate-ammonium, glufosinate-P-sodium, glufosinate-P-ammonium, glufosinate-P-sodium, glyphosate, glyphosate-ammonium, -isopropylammonium, -diammonium, -dimethylammonium, -potassium, -sodium and -trimesium, H-9201, i.e. O-(2,4-dimethyl-6-nitrophenyl) O-ethyl isopropylphosphoramidothioate, halauxifen, halauxifen-methyl, halosafen, halosulfuron, halosulfuron-methyl, haloxyfop, haloxyfop-P, haloxyfop-ethoxyethyl, haloxyfop-P-ethoxyethyl, haloxyfop-methyl, haloxyfop-P-methyl, hexazinone, HW-02, i.e. 1-(dimethoxyphosphoryl) ethyl (2,4-dichlorophenoxy)acetate, imazamethabenz, Imazamethabenz-methyl, imazamox, imazamox-ammonium, imazapic, imazapic-ammonium, imazapyr, imazapyr-isopropylammonium, imazaquin, imazaquin-ammonium, imazethapyr, imazethapyr-immonium, imazosulfuron, indanofan, indaziflam, iodosulfuron, iodosulfuron-methyl-sodium, ioxynil, ioxynil-octanoate, -potassium and sodium, ipfencarbazone, isoproturon, isouron, isoxaben, isoxaflutole, karbutilate, KUH-043, i.e. 3-({[5-(difluoromethyl)-1-methyl-3-(trifluoromethyl)-1H-pyrazol-4-yl] methyl}sulfonyl)-5,5-dimethyl-4,5-dihydro-1,2-oxazole, ketospiradox, lactofen, lenacil, linuron, MCPA, MCPA-butotyl, -dimethylammonium, -2-ethylhexyl, -isopropylammonium, -potassium and -sodium, MCPB, MCPB-methyl, -ethyl and -sodium, mecoprop, mecoprop-sodium, and -butotyl, mecoprop-P, mecoprop-P-butotyl, -dimethylammonium, -2-ethylhexyl and -potassium, mefenacet, mefluidide, mesosulfuron, mesosulfuron-methyl, mesotrione, methabenzthiazuron, metam, metamifop, metamitron, metazachlor, metazosulfuron, methabenzthiazuron, methiopyrsulfuron, methiozolin, methyl isothiocyanate, metobromuron, metolachlor, S-metolachlor, metosulam, metoxuron, metribuzin, metsulfuron, metsulfuron-methyl, molinat, monolinuron, monosulfuron, monosulfuron-ester, MT-5950, i.e. N-[3-chloro-4-(1-methylethyl)phenyl]-2-methylpentanamide, NGGC-011, napropamide, NC-310, i.e. 4-(2,4-dichlorobenzoyl)-1-methyl-5-benzyloxypyrazole, neburon, nicosulfuron, nonanoic acid (pelargonic acid), norflurazon, oleic acid (fatty acids), orbencarb, orthosulfamuron, oryzalin, oxadiargyl, oxadiazon, oxasulfuron, oxaziclomefon, oxyfluorfen, paraquat, paraquat dichloride, pebulate, pendimethalin, penoxsulam, pentachlorphenol, pentoxazone, pethoxamid, petroleum oils, phenmedipham, picloram, picolinafen, pinoxaden, piperophos, pretilachlor, primisulfuron, primisulfuron-methyl, prodiamine, profoxydim, prometon, prometryn, propachlor, propanil, propaquizafop, propazine, propham, propisochlor, propoxycarbazone, propoxycarbazone-sodium, propyrisulfuron, propyzamide, prosulfocarb, prosulfuron, pyraclonil, pyraflufen, pyraflufen-ethyl, pyrasulfotole, pyrazolynate (pyrazolate), pyrazosulfuron, pyrazosulfuron-ethyl, pyrazoxyfen, pyribambenz, pyribambenz-isopropyl, pyribambenz-propyl, pyribenzoxim, pyributicarb, pyridafol, pyridate, pyriftalid, pyriminobac, pyriminobac-methyl, pyrimisulfan, pyrithiobac, pyrithiobac-sodium, pyroxasulfone, pyroxsulam, quinclorac, quinmerac, quinoclamine, quizalofop, quizalofop-ethyl, quizalofop-P, quizalofop-P-ethyl, quizalofop-P-tefuryl, rimsulfuron, saflufenacil, sethoxydim, siduron, simazine, simetryn, SL-261, sulcotrion, sulfentrazone, sulfometuron, sulfometuron-methyl, sulfosulfuron, SYP-249, i.e. 1-ethoxy-3-methyl-1-oxobut-3-en-2-yl 5-[2-chloro-4-(trifluoromethyl)phenoxy]-2-nitrobenzoate, SYP-300, i.e. 1-[7-fluoro-3-oxo-4-(prop-2-yn-1-yl)-3,4-dihydro-2H-1,4-benzoxazin-6-yl]-3-propyl-2-thioxoimidazolidine-4,5-dione, 2,3,6-TBA, TCA (trifluoroacetic acid), TCA-sodium, tebuthiuron, tefuryltrione, tembotrione, tepraloxydim, terbacil, terbucarb, terbumeton, terbuthylazin, terbutryn, thenylchlor, thiazopyr, thiencarbazone, thiencarbazone-methyl, thifensulfuron, thifensulfuron-methyl, thiobencarb, tiafenacil, tolpyralate, topramezone, tralkoxydim, triafamone, triallate, triasulfuron, triaziflam, tribenuron, tribenuron-methyl, triclopyr, trietazine, trifloxysulfuron, trifloxysulfuron-sodium, trifludimoxazin, trifluralin, triflusulfuron, triflusulfuron-methyl, tritosulfuron, urea sulfate, vernolate, XDE-848, ZJ-0862, i.e. 3,4-dichloro-N-{2-[(4,6-dimethoxypyrimidin-2-yl)oxy]benzyl}aniline, and the following compounds:

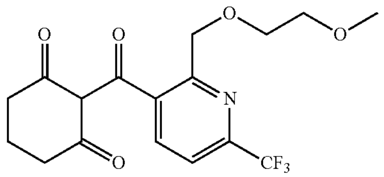

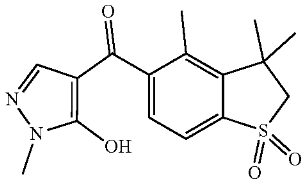

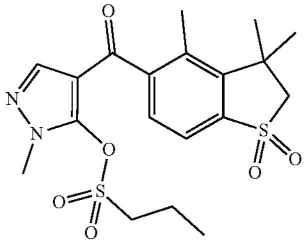

-continued

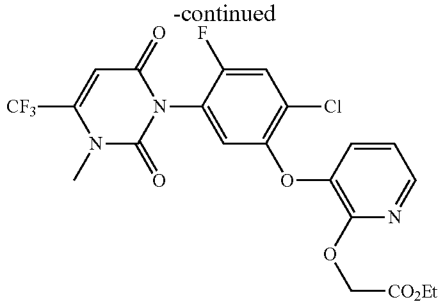

Examples of plant growth regulators as possible mixing partners are:

acibenzolar, acibenzolar-S-methyl, 5-aminolevulinic acid, ancymidol, 6-benzylaminopurine, brassinolide, catechol, chlormequat chloride, cloprop, cyclanilide, 3-(cycloprop-1-enyl)propionic acid, daminozide, dazomet, n-decanol, dikegulac, dikegulac-sodium, endothal, endothal-dipotassium, -disodium, and mono(N,N-dimethylalkylammonium), ethephon, flumetralin, flurenol, flurenol-butyl, flurprimidol, forchlorfenuron, gibberellic acid, inabenfide, indole-3-acetic acid (IAA), 4-indol-3-ylbutyric acid, isoprothiolane, probenazole, jasmonic acid, jasmonic acid methyl ester, maleic hydrazide, mepiquat chloride, 1-methylcyclopropene, 2-(1-naphthyl)acetamide, 1-naphthylacetic acid, 2-naphthyloxyacetic acid, nitrophenolate mixture, 4-oxo-4 [(2-phenylethyl)amino]butyric acid, paclobutrazole, N-phenylphthalamic acid, prohexadione, prohexadione-calcium, prohydrojasmone, salicylic acid, strigolactone, tecnazene, thidiazuron, triacontanol, trinexapac, trinexapac-ethyl, tsitodef, uniconazole, uniconazole-P.

In the case of employment as active ingredient formulations or co-formulations, these generally contain, as the case may be, the respectively customary stickers, wetters, dispersants, emulsifiers, penetrants, preservatives, antifreezes and solvents, fillers, carriers and dyes, defoamers, evaporation inhibitors, and pH and viscosity modifiers.

The compounds of the general formula (I) and combinations thereof with one or more of the pesticides mentioned may be formulated in various ways depending on the defined physicochemical and biological parameters.

Suitable examples of types of formulation include:

emulsifiable concentrates that are produced by dissolving the active ingredients in an organic solvent, for example butanol, cyclohexanone, dimethylformamide, xylene, or else relatively high-boiling hydrocarbons or mixtures of the organic solvents, with addition of one or more ionic and/or nonionic surfactants (emulsifiers).

Suitable emulsifiers are, for example, calcium alkylarylsulfonates, fatty acid polyglycol esters, alkylaryl polyglycol ethers, fatty alcohol polyglycol ethers, propylene oxide-ethylene oxide condensation products, alkyl polyethers, sorbitan esters and polyoxyethylene sorbitan fatty acid esters;

dusting products that are obtained by grinding the active ingredients with finely divided solid inorganic or organic substances, e.g. talc, natural clays, such as kaolin, bentonite and pyrophyllite, diatomaceous earth or flours;

water- or oil-based suspension concentrates that can be produced, for example, by wet grinding by means of bead mills;

water-soluble powders;

water-soluble concentrates;

granules, such as water-soluble granules, water-dispersible granules and granules for broadcasting and soil application;

wettable powders which, as well as the active ingredient, also contain diluents or inert substances and surfactants;

capsule suspensions and microcapsules;

ultralow-volume formulations.

The abovementioned formulation types are known to the person skilled in the art and are described, for example, in: K. Martens, "Spray Drying Handbook", 3rd ed., G. Goodwin Ltd., London. 1979; W. van Valkenburg, "Pesticide Formulations", Marcel Dekker, N.Y. 1973; Winacker-Ktichler, "Chemische Technologie" [Chemical Technology], volume 7, C. Hanser Verlag Munich, 4th edition 1986; "Perry's Chemical Engineer's Handbook", 5th ed., McGraw-Hill, N.Y. 1973, pages 8-57.

The necessary formulation auxiliaries such as inert materials, surfactants, solvents and further additives are likewise known and are described, for example, in:

McCutcheon's "Detergents and Emulsifiers Annual", MC Publ. Corp., Ridgewood N.J.; C. Marsden, "Solvents Guide", 2nd ed., Interscience, N.Y. 1963; H. von Olphen, "Introduction to Clay Colloid Chemistry", 2nd ed., J. Wiley & Sons, N.Y.; Schonfeldt, "Grenzflachenaktive Athylenoxidaddukte" [Interface-active Ethylene Oxide Adducts], Wiss. Verlagsgesellschaft, Stuttgart 1976; Sisley and Wood, "Encyclopedia of Surface Active Agents", Chem. Publ. Co. Inc., N.Y. 1964; Watkins, "Handbook of Insecticide Dust Diluents and Carriers", 2nd ed., Darland Books, Caldwell N.J.; Winnacker-Ktichler, "Chemische Technologie", volume 7, C. Hanser Verlag Munich, 4th edition 1986.

Apart from the aforementioned formulation auxiliaries, the useful plant-protecting compositions may, as the case may be, contain customary wetters, stickers, dispersants, penetrants, emulsifiers, preservatives, antifreezes, fillers, carriers and dyes, defoamers, evaporation inhibitors, and pH or viscosity modifiers.

According to the type of formulation, the useful plant-protecting compositions contain generally 0.1% to 99% by weight, especially 0.2% to 95% by weight, of one or more safeners of the general formula (I) or a combination of safener and pesticide.

They additionally contain 1% to 99.9%, especially 4% to 99.5%, by weight of one or more solid or liquid additives and 0% to 25%, especially 0.1 to 25%, by weight of a surfactant. In emulsifiable concentrates, the active ingredient concentration, i.e. the concentration of safener and/or pesticide, is generally 1% to 90%, especially 5% to 80%, by weight.

Dusting products typically contain 1% to 30%, preferably 5% to 20%, by weight of active ingredient. In wettable powders, the active ingredient concentration is generally 10% to 90% by weight.

In the water-dispersible granules, the content of active ingredient is, for example, between 1% and 95% by weight, preferably between 10% and 80% by weight.

For application, the formulations in the commercial form are diluted if appropriate in a customary manner, for example with water in the case of wettable powders, emulsifiable concentrates, dispersions and water-dispersible granules.

Preparations in dust form, granules and sprayable solutions are not normally diluted further with other inert substances prior to application.

The required application rate of the safeners of the general formula (I) varies with external conditions including temperature, humidity and the type of herbicide used.

In the examples which follow, which illustrate but do not limit the invention, statements of amount are based on weight unless defined otherwise.

EXAMPLES

1. Formulation Examples 1.1 Dusting Product

A dusting product is obtained by mixing 10 parts by weight of a compound of the general formula (I) (safener) or of an active ingredient mixture composed of a pesticide (e.g. a herbicide) and a safener of the general formula (I) and 90 parts by weight of talc as inert substance, and comminuting in a bead mill 1.2 Water-Dispersible Powder A readily water-dispersible wettable powder is obtained by mixing 25 parts by weight of a compound of the general formula (I) or of an active ingredient mixture of a pesticide (e.g. a herbicide) and a safener of the general formula (I), 64 parts by weight of kaolin-containing quartz as an inert substance, 10 parts by weight of potassium lignosulfonate and 1 part by weight of sodium oleoylmethyltaurate as a wetting agent and dispersant, and grinding the mixture in a pinned-disk mill 1.3 Water-Dispersible Granules A water-dispersible dispersion concentrate is obtained by mixing 20 parts by weight of a compound of the general formula (I) or of an active ingredient mixture of a pesticide (e.g. a herbicide) and a safener of the formula (I) with 6 parts by weight of alkylphenol polyglycol ether (®Triton X 207), 3 parts by weight of isotridecanol polyglycol ether and 71 parts by weight of paraffinic mineral oil, and grinding in a friction ball mill to a fineness below 5 microns.

1.4 Emulsifiable Concentrate

An emulsifiable concentrate is obtained from 15 parts by weight of a compound of the general formula (I) or of an active ingredient mixture composed of a pesticide (e.g. a herbicide) and a safener of the general formula (I), 75 parts by weight of cyclohexanone as solvent and 10 parts by weight of ethoxylated nonylphenol as emulsifier.

1.5 Water-Dispersible Granules

Water-dispersible granules are obtained by mixing 75 parts by weight of a safener of the general formula (I) or a mixture of a pesticide and a safener of the general formula (I), 10 " of calcium lignosulfonate, 5 " of sodium laurylsulfate, 3 " of polyvinyl alcohol and 7 " of polyvinyl alcohol and 7 " of kaolin, grinding the mixture in a pinned-disk mill, and granulating the powder in a fluidized bed by spray application of water as a granulating liquid.

Water-dispersible granules are also obtained by homogenizing and comminuting, in a colloid mill, 25 parts by weight of a safener of the general formula (I) or a mixture of a pesticide and a safener of the general formula (I), 5 " of sodium 2,2'-dinaphthylmethane-6,6'-disulfonate, 2 " of sodium oleoylmethyltaurinate, 17 " of calcium carbonate, 50 " of water and 1 part by weight of polyvinyl alcohol, then grinding the mixture in a bead mill and atomizing and drying the suspension thus obtained in a spray tower by means of a one-phase nozzle.

2. Biological Examples 2.1 Relative Action of Selected Compounds of the Invention Using the Example of Reduction of Damage by Mesosulfuron-Methyl on Summer Barley (HORVS)

The seeds of the crop plants to be treated are laid out in sandy loam in plastic pots (diameter ~4 cm), covered with soil and grown in a greenhouse under good conditions for germination and growth. The trial plants were treated at the early leaf stage (BBCH10-BBCH12). In the course of this, the inventive compounds of the general formula (I) formulated in the form of wettable powders (WP) were sprayed onto the above-ground parts of the plants as an aqueous suspension with a water application rate corresponding to 800 l/ha with addition of wetting agent (e.g. 0.2% Genapol-LRO or 0.2% Mero) in the specified dose.

This was followed by the application of the herbicide. For this purpose, mesosulfuron-methyl, formulated in the form of water-dispersible granules (WG), was sprayed onto the above-ground parts of the plants in the form of an aqueous dispersion with a water application rate corresponding to 800 l/ha with addition of wetting agent (e.g. 0.2% Genapol-LRO or 1 l/ha Biopower) in a dose of 40-60 g/ha. The dose of the herbicide was chosen here such that it causes visually apparent damage (min. 30%, max. 75%) compared to untreated crop plants at the evaluation time on a control group of crop plants without safener treatment that were included in the same trial.

After application, the plants were cultivated under good growth conditions in a greenhouse. 9-13 days after application, the efficacy of the test compounds was assessed visually. For this purpose, the appearance of the plants treated with the test compound and herbicide was compared to the corresponding herbicide controls (without safener; with clearly visible damage) and the untreated controls (without damage). The damage-reducing effect of the test compounds was expressed here separately for 2 repeats in graded efficacy codes according to the following scheme:

0: no reduction in damage (appearance corresponding to the herbicide control)

1: slight reduction in damage

2: distinct reduction in damage

3: significant reduction in damage

4: complete reduction in damage (appearance corresponding to the untreated control)

The trials show clear efficacy of the the inventive compounds selected by way of example with regard to the reduction in damage to the summer barley crop plant (HORVS; cv. Montoya) caused by the herbicide mesosulfuron-methyl:

| Example No. | Dose of the safener of the formula (I) (g/ha) | Crop plant | Efficacy of the safener (efficacy code) |
|---|---|---|---|
| I.40-11 | 500 | HORVS | 2 |
| I.40-10 | 500 | HORVS | 2-3 |
| I.40-10 | 100 | HORVS | 2 |
| I.46-10 | 500 | HORVS | 2 |
| I.46-10 | 100 | HORVS | 2 |

-continued

| Example No. | Dose of the safener of the formula (I) (g/ha) | Crop plant | Efficacy of the safener (efficacy code) |
|---|---|---|---|
| I.48-10 | 500 | HORVS | 2-3 |
| I.48-10 | 100 | HORVS | 2 |

What is claimed is:

1. A compound of general formula (I) or salt thereof

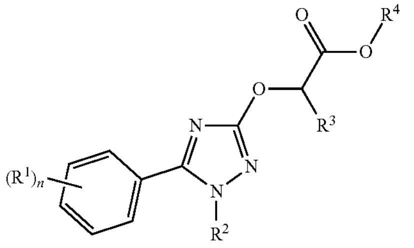

(I)

in which $R^1$ is selected from hydrogen, halogen, cyano, nitro, $(C_1-C_6)$alkyl, $(C_2-C_6)$alkenyl, $(C_2-C_6)$alkynyl, $(C_3-C_8)$cycloalkyl, $(C_3-C_8)$cycloalkenyl, $(C_1-C_6)$alkoxy or $(C_1-C_6)$alkylS$(O)_p$, wherein $(C_1-C_6)$alkyl, $(C_2-C_6)$alkenyl, $(C_2-C_6)$alkynyl, $(C_3-C_8)$cycloalkyl, $(C_3-C_8)$cycloalkenyl, $(C_1-C_6)$alkoxy and $(C_1-C_6)$alkylS$(O)_p$ are optionally substituted by one or more radicals selected from the group consisting of halogen, cyano, $(C_1-C_6)$alkoxy and $(C_1-C_6)$alkylS$(O)_p$, $R^2$ is heteroaryl, where the heteroaryl radical is unsubstituted or substituted by halogen, cyano, nitro, $(C_1-C_6)$alkyl, $(C_2-C_6)$alkenyl, $(C_2-C_6)$alkynyl, $(C_3-C_8)$cycloalkyl, $(C_3-C_8)$cycloalkenyl, $(C_1-C_6)$alkoxy or $(C_1-C_6)$alkylS$(O)_p$, wherein $(C_1-C_6)$alkyl, $(C_2-C_6)$alkenyl, $(C_2-C_6)$alkynyl, $(C_3-C_8)$cycloalkyl, $(C_3-C_8)$cycloalkenyl, $(C_1-C_6)$alkoxy and $(C_1-C_6)$alkylS$(O)_p$ are optionally substituted by one or more radicals selected from the group consisting of halogen, cyano, $(C_1-C_6)$alkoxy and $(C_1-C_6)$alkylS$(O)_p$, $R^3$ is hydrogen or $(C_1-C_6)$alkyl, $R^4$ is selected from hydrogen, $(C_1-C_{18})$alkyl, $(C_1-C_{18})$haloalkyl, $(C_1-C_{18})$cyanoalkyl, $(C_2-C_{18})$alkenyl, $(C_2-C_{18})$alkynyl, $(C_3-C_{12})$cycloalkyl, $(C_3-C_{12})$cycloalkenyl, aryl, heteroaryl, $(C_1-C_{18})$alkoxy-$(C_1-C_{18})$alkyl, $(C_1-C_{18})$haloalkoxy-$(C_1-C_{18})$alkyl, $(C_1-C_{18})$alkoxy-$(C_1-C_{18})$haloalkyl, $(C_1-C_{18})$alkylthio-$(C_1-C_{18})$alkyl, $(C_1-C_{18})$haloalkylthio-$(C_1-C_{18})$alkyl, $(C_2-C_{18})$haloalkenyl, $(C_2-C_{18})$haloalkynyl, heterocyclyl-$(C_1-C_{18})$alkyl, aryl-$(C_1-C_{18})$alkyl, $(C_3-C_{12})$cycloalkyl-$(C_1-C_{18})$alkyl, $(C_1-C_{18})$alkoxycarbonyl-$(C_1-C_{18})$alkyl, and $(C_1-C_{18})$alkoxycarbonyl-$(C_3-C_{12})$cycloalkyl-$(C_1-C_{18})$alkyl, or a radical of the formula —$NR^aR^b$ or —N═$CR^cR^d$, wherein each of the $R^a$, $R^b$, $R^c$ and $R^d$ radicals is independently selected from hydrogen, $(C_1-C_4)$alkyl, $(C_2-C_4)$alkenyl, $(C_2-C_4)$alkynyl, benzyl, substituted benzyl, phenyl or substituted phenyl, or $R^a$ and $R^b$ together with the nitrogen atom may form a 3- to 8-membered heterocycle which may contain one or two ring heteroatoms from the group of N, O and S, but not in the case of a 3- or 4-membered heterocycle, and which is unsubstituted or substituted by one or more radicals from the group of $(C_1-C_4)$alkyl and $(C_1-C_4)$haloalkyl, or $R^c$ and $R^d$ together with the carbon atom are a 3- to 8-membered carbocyclic or heterocyclic radical which may contain 1 to 3 ring heteroatoms from the group of N, O and S, where the carbocyclic or heterocyclic radical is unsubstituted or substituted by one or more radicals from the group of $(C_1-C_4)$-alkyl and $(C_1-C_4)$-haloalkyl, n is a number from 0 to 5, and p is 0, 1 or 2.

2. The compound of the general formula (I) as claimed in claim 1 or salt thereof, in which $R^1$ is selected from hydrogen, halogen, cyano, nitro, $(C_1-C_4)$alkyl, $(C_2-C_4)$alkenyl, $(C_2-C_4)$alkynyl, $(C_3-C_6)$cycloalkyl, $(C_3-C_6)$cycloalkenyl, $(C_1-C_4)$alkoxy or $(C_1-C_4)$alkylS$(O)_p$, wherein $(C_1-C_6)$alkyl, $(C_2-C_6)$alkenyl, $(C_2-C_6)$alkynyl, $(C_3-C_8)$cycloalkyl, $(C_3-C_8)$cycloalkenyl, $(C_1-C_6)$alkoxy and $(C_1-C_6)$alkyl-S$(O)_p$ are optionally substituted by one or more radicals selected from the group consisting of halogen, cyano, $(C_1-C_4)$alkoxy and $(C_1-C_4)$alkylS$(O)_p$, $R^2$ is heteroaryl, where the heteroaryl radical is an unsubstituted or substituted by halogen, cyano, nitro, $(C_1-C_6)$alkyl, $(C_2-C_6)$alkenyl, $(C_2-C_4)$alkynyl, $(C_3-C_6)$cycloalkyl, $(C_3-C_6)$cycloalkenyl, $(C_1-C_6)$alkoxy and $(C_1-C_4)$alkylS$(O)_p$, wherein $(C_1-C_6)$alkyl, $(C_2-C_6)$alkenyl, $(C_2-C_6)$alkynyl, $(C_3-C_8)$cycloalkyl, $(C_3-C_8)$cycloalkenyl, $(C_1-C_6)$alkoxy and $(C_1-C_6)$alkylS$(O)_p$ are optionally substituted by one or more radicals selected from the group consisting of halogen, cyano, $(C_1-C_4)$alkoxy and $(C_1-C_4)$alkylS$(O)_p$, $R^3$ is hydrogen or $(C_1-C_4)$alkyl, $R^4$ is selected from hydrogen, $(C_1-C_{16})$alkyl, $(C_1-C_{16})$haloalkyl, $(C_1-C_{16})$cyanoalkyl, $(C_2-C_{16})$alkenyl, $(C_2-C_{16})$alkynyl, $(C_3-C_{12})$cycloalkyl, $(C_3-C_{12})$cycloalkenyl, aryl, heteroaryl, $(C_1-C_{16})$alkoxy-$(C_1-C_{16})$alkyl, $(C_1-C_{16})$haloalkoxy-$(C_1-C_{16})$alkyl, $(C_1-C_{16})$alkoxy-$(C_1-C_{16})$haloalkyl, $(C_1-C_{16})$alkylthio-$(C_1-C_{16})$alkyl, $(C_1-C_{16})$haloalkylthio-$(C_1-C_{16})$alkyl, $(C_2-C_{16})$haloalkenyl, $(C_2-C_{16})$haloalkynyl, heterocyclyl-$(C_1-C_{16})$alkyl, aryl-$(C_1-C_{16})$alkyl, $(C_3-C_{12})$cycloalkyl-$(C_1-C_{16})$alkyl, $(C_1-C_{16})$alkoxycarbonyl-$(C_1-C_{16})$alkyl, and $(C_1-C_{16})$alkoxycarbonyl-$(C_3-C_{12})$cycloalkyl-$(C_1-C_{16})$alkyl, n is a number from 0 to 4, and p is 0, 1 or 2.

3. The compound of the general formula (I) as claimed in claim 1 or salt thereof, in which $R^1$ is selected from hydrogen, halogen, cyano, methyl, ethyl, $CF_3$, $CF_2Cl$, $CH_2F$, $CHF_2$, $OCH_3$, $OCF_3$, $SCH_3$, $SOCH_3$, $SO_2CH_3$ and $SCF_3$, $R^2$ is heteroaryl, where the heteroaryl radical is unsubstituted or mono- or polysubstituted by halogen, cyano, methyl, ethyl, $CF_3$, $CF_2Cl$, $CH_2F$, $CHF_2$, $OCH_3$, $OCF_3$, $SCH_3$, $SOCH_3$, $SO_2CH_3$ or $SCF_3$, $R^3$ is hydrogen, $CH_2CH_3$, or $CH_3$, $R^4$ is selected from hydrogen, $(C_1-C_{12})$alkyl, $(C_1-C_{12})$haloalkyl, $(C_1-C_{12})$cyanoalkyl, $(C_2-C_{12})$alkenyl, $(C_2-C_{12})$alkynyl, $(C_3-C_{12})$cycloalkyl, $(C_3-C_{12})$cycloalkenyl, aryl, heteroaryl, $(C_1-C_{12})$alkoxy-$(C_1-C_{12})$alkyl, $(C_1-C_{12})$haloalkoxy-$(C_1-C_{12})$alkyl, $(C_1-C_{12})$alkoxy-$(C_1-C_{12})$haloalkyl, $(C_1-C_{12})$alkylthio-$(C_1-C_{12})$alkyl, $(C_1\text{-}C_{12})$haloalkylthio-$(C_1\text{-}C_{12})$alkyl, $(C_2\text{-}C_{12})$haloalkenyl, $(C_2\text{-}C_{12})$haloalkynyl, heterocyclyl-$(C_1\text{-}C_{12})$alkyl, aryl-$(C_1\text{-}C_{12})$alkyl, $(C_3\text{-}C_{12})$cycloalkyl-$(C_1\text{-}C_{12})$alkyl, $(C_1\text{-}C_{12})$alkoxycarbonyl-$(C_1\text{-}C_{12})$alkyl, or $(C_1\text{-}C_{12})$alkoxycarbonyl-$(C_3\text{-}C_{12})$cycloalkyl-$(C_1\text{-}C_{12})$alkyl, and n is 0, 1, 2 or 3.

4. The compound of the general formula (I) as claimed in claim 1 or salt thereof, in which $R^1$ is selected from hydrogen, fluorine, chlorine, bromine, iodine, CN, methyl, ethyl, $CF_3$, $CF_2Cl$, $CH_2F$, $CHF_2$, $OCH_3$, $OCF_3$, $SCH_3$, $SOCH_3$, $SO_2CH_3$ and $SCF_3$, $R^2$ is pyridin-2-yl, pyridin-3-yl, pyridin-4-yl, pyrazin-2-yl, pyrazin-3-yl, pyrimidin-2-yl, pyrimidin-4-yl, pyrimidin-5-yl, pyridazin-3-yl, pyridazin-4-yl, 1,3,5-triazin-2-yl, 1,2,4-triazin-3-yl, 1,2,4-triazin-5-yl, 1,2,4-triazin-6-yl, 1,2,3-triazin-4-yl, 1,2,3-triazin-5-yl, 1,2,4-, 1,3,2-, 1,3,6- and 1,2,6-oxazinyl, isoxazol-3-yl, isoxazol-4-yl, isoxazol-5-yl, 1,3-oxazol-2-yl, 1,3-oxazol-4-yl, 1,3-oxazol-5-yl, isothiazol-3-yl, isothiazol-4-yl, isothiazol-5-yl, 1,3-thiazol-2-yl, 1,3-thiazol-4-yl, 1,3-thiazol-5-yl, 1H-pyrrol-1-yl, 1H-pyrrol-2-yl, 1H-pyrrol-3-yl, furan-2-yl, furan-3-yl, thien-2-yl; thien-3-yl, 1H-imidazol-1-yl, 1H-imidazol-2-yl, 1H-imidazol-4-yl, 1H-imidazol-5-yl, 1H-pyrazol-1-yl, 1H-pyrazol-3-yl, 1H-pyrazol-4-yl, 1H-pyrazol-5-yl, 1H-1,2,3-triazol-1-yl, 1H-1,2,3-triazol-4-yl, 1H-1,2,3-triazol-5-yl, 2H-1,2,3-triazol-2-yl, 2H-1,2,3-triazol-4-yl, 1H-1,2,4-triazol-1-yl, 1H-1,2,4-triazol-5-yl, 4H-1,2,4-triazol-3-yl, 1,2,4-oxadiazol-3-yl, 1,2,4-oxadiazol-5-yl, 1,3,4-oxadiazol-2-yl, 1,2,3-oxadiazol-4-yl, 1,2,3-oxadiazol-5-yl, 1,2,5-oxadiazol-3-yl, 1,3,4-thiadiazol-2-yl, 1,3,4-thiadiazol-5-yl, 1,2,4-thiadiazol-5-yl, 1,2,4-thiadiazol-3-yl, 1,2,5-thiadiazol-3-yl, 1,2,5-thiadiazol-3-yl, 1,2,3-thiadiazol-4-yl, or 1,2,3-thiadiazol-3-yl, which is an unsubstituted or mono- or polysubstituted by halogen, cyano, methyl, $CF_3$, $CF_2Cl$, $CH_2F$, $CHF_2$, $OCH_3$, $OCF_3$, $SCH_3$, $SOCH_3$, $SO_2CH_3$ or $SCF_3$, $R^3$ is hydrogen or $CH_3$, $R^4$ is selected from hydrogen, $(C_1\text{-}C_{10})$alkyl, $(C_1\text{-}C_{10})$haloalkyl, $(C_1\text{-}C_{10})$cyanoalkyl, $(C_2\text{-}C_{10})$alkenyl, $(C_2\text{-}C_{10})$alkynyl, $(C_3\text{-}C_9)$cycloalkyl, $(C_3\text{-}C_9)$cycloalkenyl, aryl, heteroaryl, $(C_1\text{-}C_{10})$alkoxy-$(C_1\text{-}C_{10})$alkyl, $(C_1\text{-}C_{10})$haloalkoxy-$(C_1\text{-}C_{10})$alkyl, $(C_1\text{-}C_{10})$alkoxy-$(C_1\text{-}C_{10})$haloalkyl, $(C_1\text{-}C_{10})$alkylthio-$(C_1\text{-}C_{10})$alkyl, $(C_1\text{-}C_{10})$haloalkylthio-$(C_1\text{-}C_{10})$alkyl, $(C_2\text{-}C_{18})$haloalkenyl, $(C_2\text{-}C_{18})$haloalkynyl, heterocyclyl-$(C_1\text{-}C_{10})$alkyl, aryl-$(C_1\text{-}C_{10})$alkyl, $(C_3\text{-}C_9)$cycloalkyl-$(C_1\text{-}C_{10})$alkyl, $(C_1\text{-}C_{10})$alkoxycarbonyl-$(C_1\text{-}C_{10})$alkyl and $(C_1\text{-}C_{10})$alkoxycarbonyl-$(C_3\text{-}C_9)$cycloalkyl-$(C_1\text{-}C_{10})$alkyl, and n is 0, 1, 2 or 3.

5. The compound of the general formula (I) as claimed in claim 1 or salt thereof, in which $R^1$ is selected from hydrogen, fluorine, chlorine, bromine, iodine, cyano, methyl, $CF_3$, $CH_2F$, $CHF_2$, $OCH_3$, $OCF_3$, $SCH_3$, $SOCH_3$, $SO_2CH_3$ and $SCF_3$, $R^2$ is selected from the group consisting of Q-2.1 to Q-2.60

Q-2.1

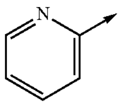

-continued

Q-2.2

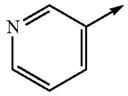

Q-2.3

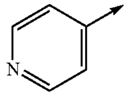

Q-2.4

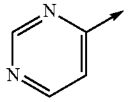

Q-2.5

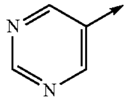

Q-2.6

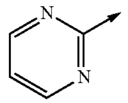

Q-2.7

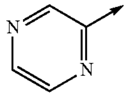

Q-2.10

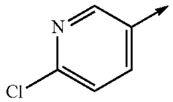

Q-2.11

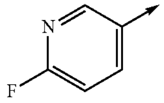

Q-2.12

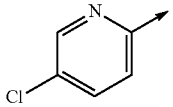

Q-2.13

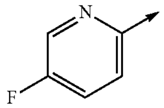

Q-2.14

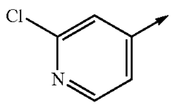

Q-2.15

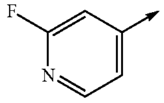

Q-2.17

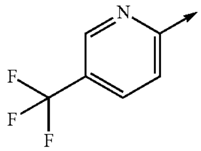

-continued

Q-2.18

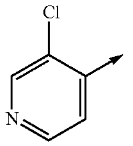

Q-2.19

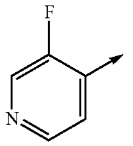

Q-2.21

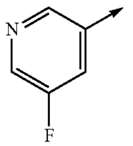

Q-2.22

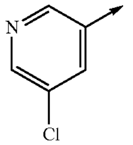

Q-2.24

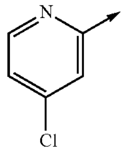

Q-2.25

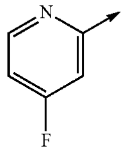

Q-2.56

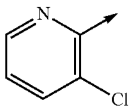

Q-2.57

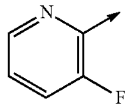

Q-2.59

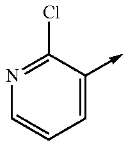

Q-2.60

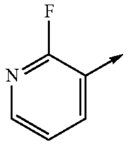

$R^3$ is hydrogen, $R^4$ is selected from hydrogen, methyl, ethyl, n-propyl, i-propyl, n-butyl, n-pentyl, phenyl, benzyl, $CH_2$(4-Cl-Ph), $CH_2$(4-F-Ph), $CH_2$(4-MeO-Ph), 2-methoxyethyl, tetrahydrofuran-2-yl-methyl, tetrahydrofuran-3-ylmethyl, tetrahydropyran-2-ylmethyl, tetrahydropyran-3-ylmethyl, tetrahydropyran-4-ylmethyl, methylpropionate-3-yl, ethylpropionate-3-yl, methylacetate-2-yl, ethylacetate-2-yl, methylpivalate-2-yl, ethylpivalate-3-yl, methyl-2-methyl-propanoate-3-yl, methyl-2,2-dimethylpropanoate-3-yl, ethyl-2-methylpropanoate-3-yl, methyl-2-propanoate-2-yl, ethyl-2-propanoate-2-yl, methylacetate-2-yl, ethylacetate-2-yl, methyl-1-methylcyclopropanecarboxylate-2-yl, ethyl-1-methylcyclopropane-carboxylat-2-yl, 2-(dimethylamino)ethyl, oxetan-3-yl, (3-methyloxetan-3-yl)methyl, 2,2,2-trifluoroethyl, 2,2-difluoroethyl, 2-fluoroethyl, 2,2,3,3,3-pentafluoropropyl, cyclopropylmethyl, 1-cyclopropylethyl, (1-methylcyclopropyl)methyl, (2,2-dichlorocyclopropyl)methyl, (2,2-dimethylcyclopropyl)methyl, allyl, propargyl (prop-2-yn-1-yl), 2-chloroprop-2-en-1-yl, 3-phenylprop-2-yn-1-yl, 3,3-dichloroprop-2-en-1-yl, 3,3-di-chloro-2-fluoroprop-2-en-1-yl, methylprop-2-yn-1-yl, 2-methylprop-2-en-1-yl, but-2-en-1-yl, but-3-en-1-yl, but-2-yn-1-yl, but-3-yn-1-yl, 4-chlorobut-2-yn-1-yl, 3-methylbut-2-en-1-yl, 3-methylbut-1-en-1-yl, 1-(2E)-1-methylbut-2-en-1-yl, I-pent-3-en-2-yl or (Z)-pent-3-en-2-yl, cyclobutylmethyl, cyclopentylmethyl, cyclohexylmethyl, heptan-2-yl, isobutyl, 1,3-dioxolan-2-ylmethyl and 1-ethyl-5-methyl-1H-pyrazole-4-methyl, n is 0, 1, 2 or 3.

6. The compound of the general formula (I) as claimed in claim 1 or salt thereof, in which $(R^1)_n$-phenyl is selected from the group consisting of Q-1.1 to Q-1.53

Q-1.1

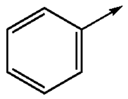

Q-1.2

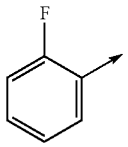

Q-1.3

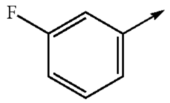

Q-1.4

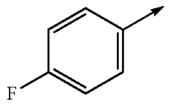

Q-1.5

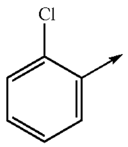

Q-1.6

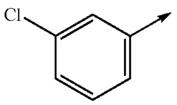

-continued
Q-1.7
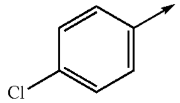
Q-1.8
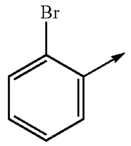
Q-1.9
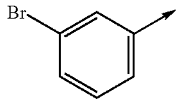
Q-1.10
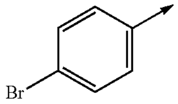
Q-1.11
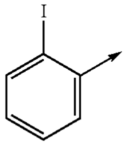
Q-1.12
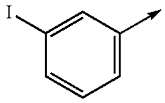
Q-1.13
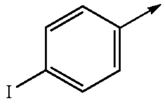
Q-1.14
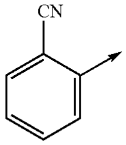
Q-1.15
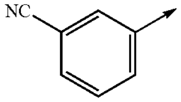
Q-1.16
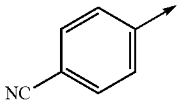
Q-1.17
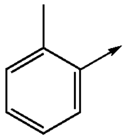
Q-1.18
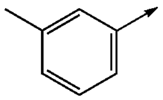
-continued
Q-1.19
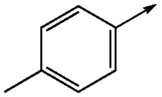
Q-1.20
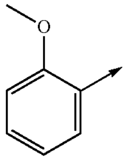
Q-1.21
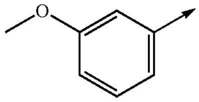
Q-1.22
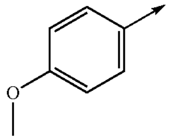
Q-1.23
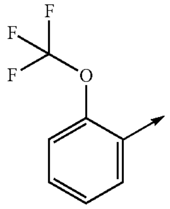
Q-1.24
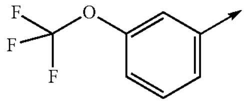
Q-1.25
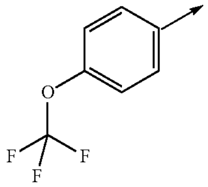
Q-1.26
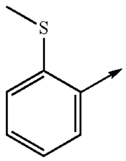
Q-1.27
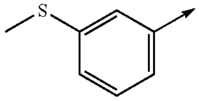
Q-1.28
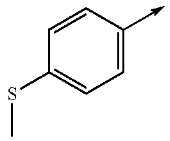

-continued
Q-1.29
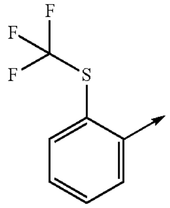
Q-1.30
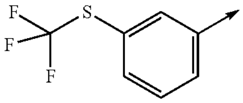
Q-1.31
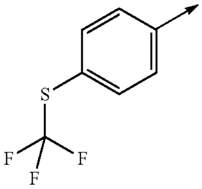
Q-1.32
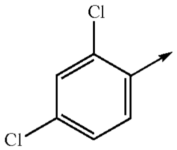
Q-1.33
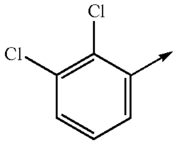
Q-1.34
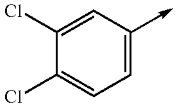
Q-1.35
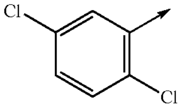
Q-1.36
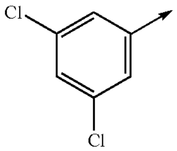
Q-1.37
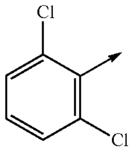
Q-1.38
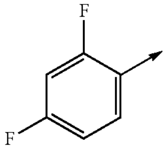
-continued
Q-1.39
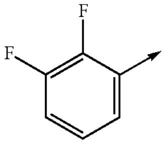
Q-1.40
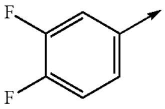
Q-1.41
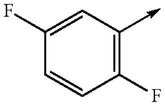
Q-1.42
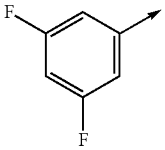
Q-1.43
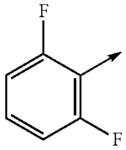
Q-1.44
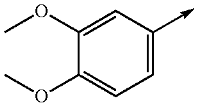
Q-1.45
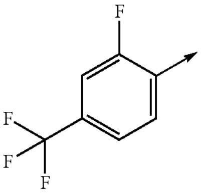
Q-1.46
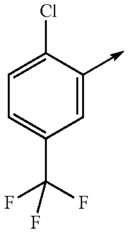
Q-1.47
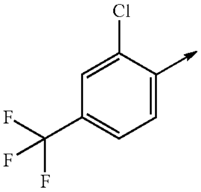

-continued
Q-1.48
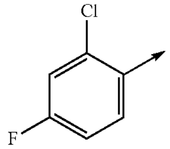
Q-1.49
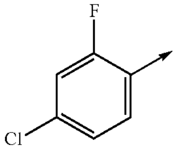
Q-1.50
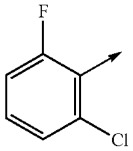
Q-1.51
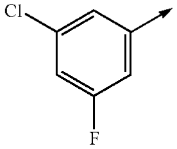
Q-1.52
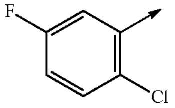
Q-1.53
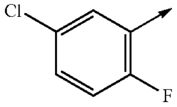
and
$R^2$ is selected from the group consisting of Q-2.1 to Q-2.60
Q-2.1
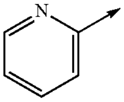
Q-2.2
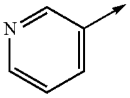
Q-2.3
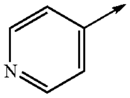
Q-2.4
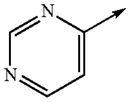
Q-2.5
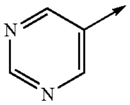
-continued
Q-2.6
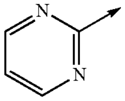
Q-2.7
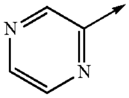
Q-2.8
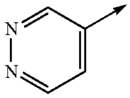
Q-2.9
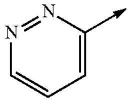
Q-2.10
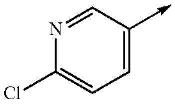
Q-2.11
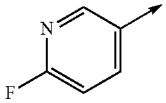
Q-2.12
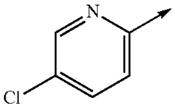
Q-2.13
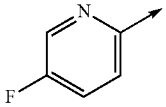
Q-2.14
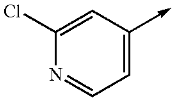
Q-2.15
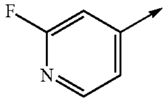
Q-2.16
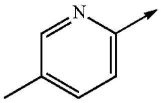
Q-2.17
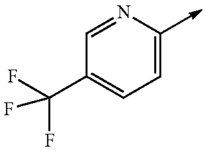
Q-2.18
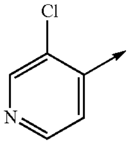

-continued
Q-2.19
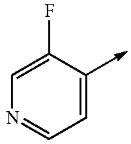
Q-2.20
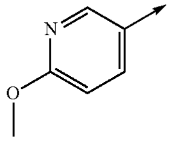
Q-2.21
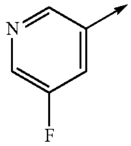
Q-2.22
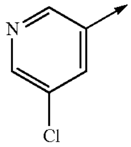
Q-2.23
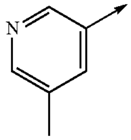
Q-2.24
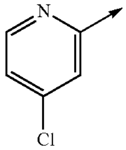
Q-2.25
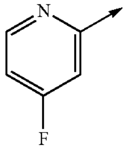
Q-2.26
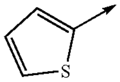
Q-2.27
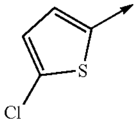
Q-2.28
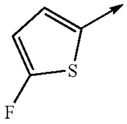
Q-2.29
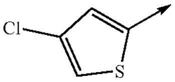
-continued
Q-2.30
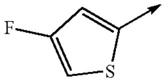
Q-2.31
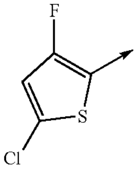
Q-2.32
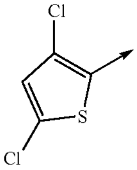
Q-2.33
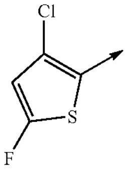
Q-2.34
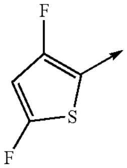
Q-2.35
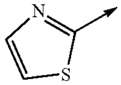
Q-2.36
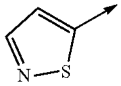
Q-2.37
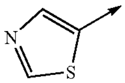
Q-2.38
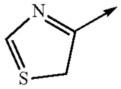
Q-2.39
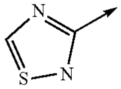
Q-2.40
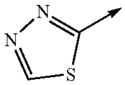
Q-2.41
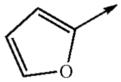
Q-2.42
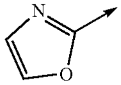

-continued

Q-2.43

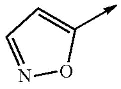

Q-2.44

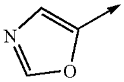

Q-2.45

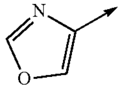

Q-2.46

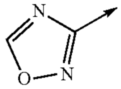

Q-2.47

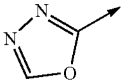

Q-2.48

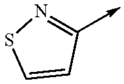

Q-2.49

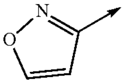

Q-2.50

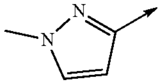

Q-2.51

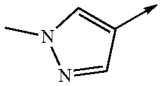

Q-2.52

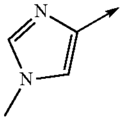

Q-2.53

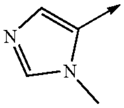

Q-2.54

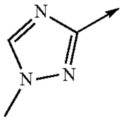

Q-2.55

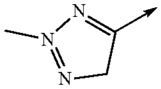

Q-2.56

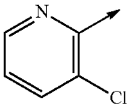

Q-2.57

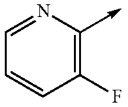

-continued

Q-2.58

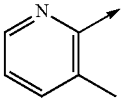

Q-2.59

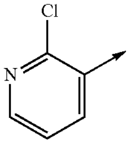

Q-2.60

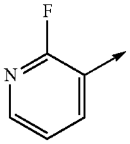

$R^3$ is hydrogen, and $R^4$ is selected from hydrogen, methyl, ethyl, n-propyl, i-propyl, n-butyl, n-pentyl, phenyl, benzyl, $CH_2$(4-Cl-Ph), $CH_2$(4-F-Ph), $CH_2$(4-MeO-Ph), 2-methoxyethyl, tetrahydrofuran-2-yl-methyl, tetrahydrofuran-3-ylmethyl, tetrahydropyran-2-ylmethyl, tetrahydropyran-3-ylmethyl, tetrahydropyran-4-ylmethyl, methylpropionate-3-yl, ethylpropionate-3-yl, methylacetate-2-yl, ethylacetate-2-yl, methylpivalate-2-yl, ethylpivalate-3-yl, methyl-2-methyl-propanoate-3-yl, methyl-2,2-dimethylpropanoate-3-yl, ethyl-2-methylpropanoate-3-yl, methyl-2-propanoate-2-yl, ethyl-2-propanoate-2-yl, methylacet-2-yl, ethylacet-2-yl, methyl-1-methylcyclopropanecarboxylate-2-yl, ethyl-1-methylcyclopropanecarboxylat-2-yl, 2-(dimethylamino)ethyl, oxetan-3-yl, (3-methyloxetan-3-yl)methyl, 2,2,2-trifluoroethyl, 2,2-difluoroethyl, 2-fluoroethyl, 2,2,3,3,3-pentafluoropropyl, cyclopropyl-methyl, 1-cyclopropylethyl, (1-methylcyclopropyl)methyl, (2,2-dichlorocyclo-propyl) methyl, (2,2-dimethylcyclopropyl)methyl, allyl, propargyl (prop-2-yn-1-yl), 2-chloroprop-2-en-1-yl, 3-phenylprop-2-yn-1-yl, 3,3-dichloroprop-2-en-1-yl, 3,3-dichloro-2-fluoroprop-2-en-1-yl, methylprop-2-yn-1-yl, 2-methylprop-2-en-1-yl, but-2-en-1-yl, but-3-en-1-yl, but-2-yn-1-yl, but-3-yn-1-yl, 4-chlorobut-2-yn-1-yl, 3-methylbut-2-en-1-yl, 3-methylbut-1-en-1-yl, 1-(2E)-1-methylbut-2-en-1-yl, I-pent-3-en-2-yl or (Z)-pent-3-en-2-yl, cyclobutylmethyl, cyclopentylmethyl, cyclohexylmethyl, heptan-2-yl, isobutyl, 1,3-dioxolan-2-ylmethyl and 1-ethyl-5-methyl-1H-pyrazole-4-methyl.

7. The compound of the general formula (I) as claimed in claim 1 or salt thereof, in which $(R^1)_n$-phenyl is selected from the group consisting of Q-1.1 to Q-1.53

Q-1.1

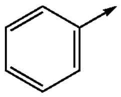

-continued
Q-1.2
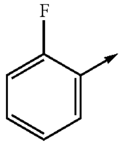
Q-1.3
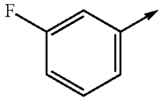
Q-1.4
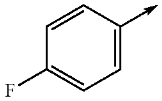
Q-1.5
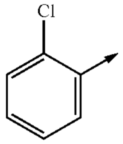
Q-1.6
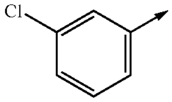
Q-1.7
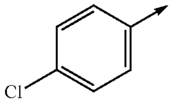
Q-1.8
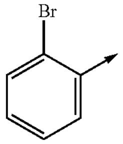
Q-1.9
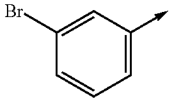
Q-1.10
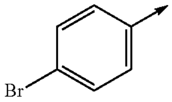
Q-1.11
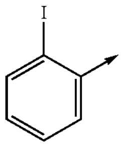
Q-1.12
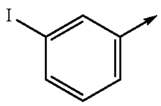
Q-1.13
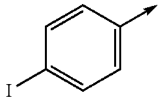
-continued
Q-1.14
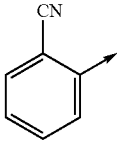
Q-1.15
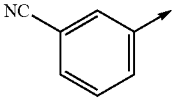
Q-1.16
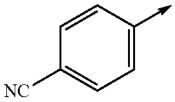
Q-1.17
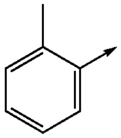
Q-1.18
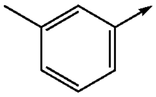
Q-1.19
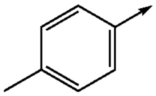
Q-1.20
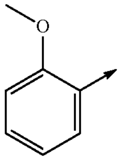
Q-1.21
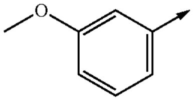
Q-1.22
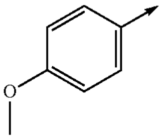
Q-1.23
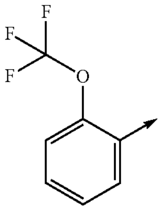
Q-1.24
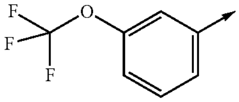

-continued
Q-1.25
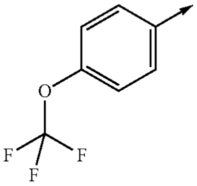
Q-1.26
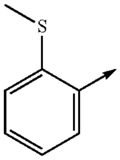
Q-1.27
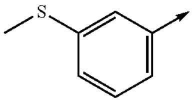
Q-1.28
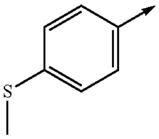
Q-1.29
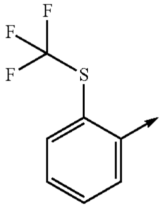
Q-1.30
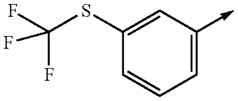
Q-1.31
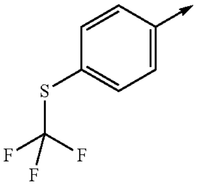
Q-1.32
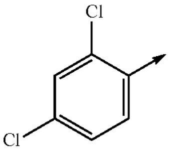
Q-1.33
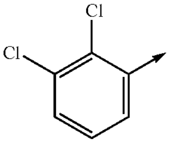
Q-1.34
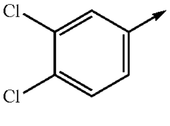
-continued
Q-1.35
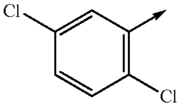
Q-1.36
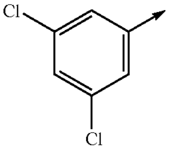
Q-1.37
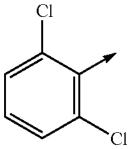
Q-1.38
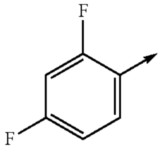
Q-1.39
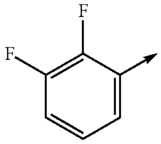
Q-1.40
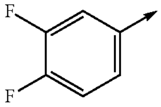
Q-1.41
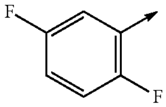
Q-1.42
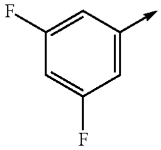
Q-1.43
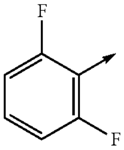
Q-1.44
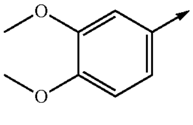

-continued
Q-1.45
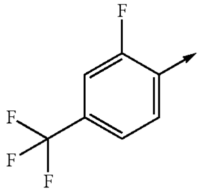
Q-1.46
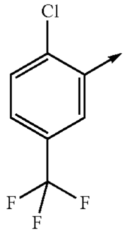
Q-1.47
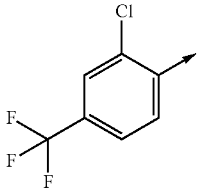
Q-1.48
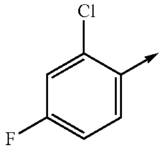
Q-1.49
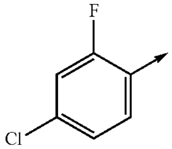
Q-1.50
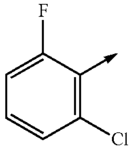
Q-1.51
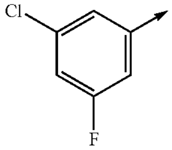
Q-1.52
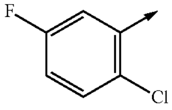
Q-1.53
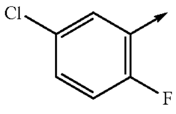
and
$R^2$ is selected from the group consisting of Q-2.1 to Q-2.60
Q-2.1
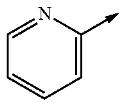
Q-2.2
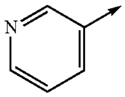
Q-2.3
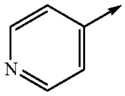
Q-2.4
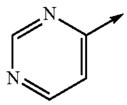
Q-2.5
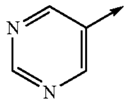
Q-2.6
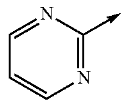
Q-2.7
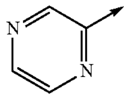
Q-2.10
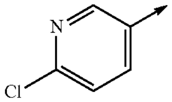
Q-2.11
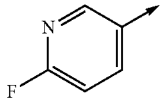
Q-2.12
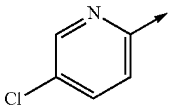
Q-2.13
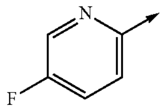
Q-2.14
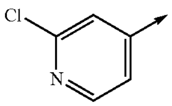
Q-2.15
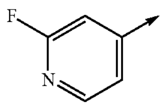

-continued

Q-2.17

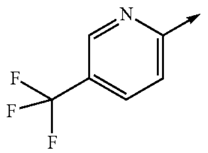

Q-2.18

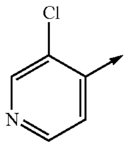

Q-2.19

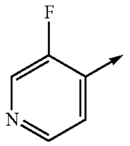

Q-2.21

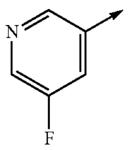

Q-2.22

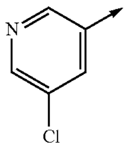

Q-2.24

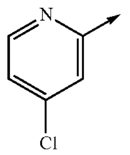

Q-2.25

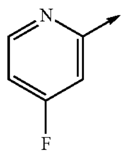

Q-2.56

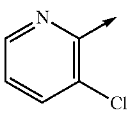

Q-2.57

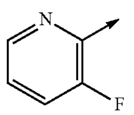

Q-2.59

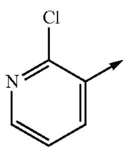

-continued

Q-2.60

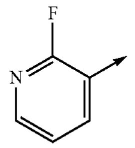

$R^3$ is hydrogen, and $R^4$ is selected from hydrogen, methyl, ethyl, n-propyl, i-propyl, n-butyl, n-pentyl, phenyl, benzyl, $CH_2$(4-Cl-Ph), $CH_2$(4-F-Ph), $CH_2$(4-MeO-Ph), 2-methoxyethyl, tetrahydrofuran-2-yl-methyl, tetrahydrofuran-3-ylmethyl, tetrahydropyran-2-ylmethyl, tetrahydropyran-3-ylmethyl, tetrahydropyran-4-ylmethyl, methylpropionate-3-yl, ethylpropionate-3-yl, methylacetate-2-yl, ethylacetate-2-yl, methylpivalate-2-yl, ethylpivalate-3-yl, methyl-2-methyl-propanoate-3-yl, methyl-2,2-dimethylpropanoate-3-yl, ethyl-2-methylpropanoate-3-yl, methyl-2-propanoate-2-yl, ethyl-2-propanoate-2-yl, methylacet-2-yl, ethylacet-2-yl, methyl-1-methylcyclopropanecarboxylate-2-yl, ethyl-1-methylcyclopropanecarboxylat-2-yl, 2-(dimethylamino)ethyl, oxetan-3-yl, (3-methyloxetan-3-yl)methyl, 2,2,2-trifluoroethyl, 2,2-difluoroethyl, 2-fluoroethyl, 2,2,3,3,3-pentafluoropropyl, cyclo-propylmethyl, 1-cyclopropylethyl, (1-methylcyclopropyl)methyl, (2,2-dichloro-cyclopropyl)methyl, (2,2-dimethylcyclopropyl)methyl, allyl, propargyl (prop-2-yn-1-yl), 2-chloroprop-2-en-1-yl, 3-phenylprop-2-yn-1-yl, 3,3-dichloroprop-2-en-1-yl, 3,3-dichloro-2-fluoroprop-2-en-1-yl, methylprop-2-yn-1-yl, 2-methylprop-2-en-1-yl, but-2-en-1-yl, but-3-en-1-yl, but-2-yn-1-yl, but-3-yn-1-yl, 4-chlorobut-2-yn-1-yl, 3-methylbut-2-en-1-yl, 3-methylbut-1-en-1-yl, 1-(2E)-1-methylbut-2-en-1-yl, I-pent-3-en-2-yl or (Z)-pent-3-en-2-yl, cyclobutylmethyl, cyclopentylmethyl, cyclohexylmethyl, heptan-2-yl, isobutyl, 1,3-dioxolan-2-ylmethyl and 1-ethyl-5-methyl-1H-pyrazole-4-methyl.

8. A plant-protecting composition, comprising:

at least one compound of the general formula (I) or salts thereof as claimed in claim 1; and at least one agrochemical.

9. The composition as claimed in claim 8, comprising at least one herbicide.

10. A method of reducing phytotoxic effects of pesticides on plants, the method comprising applying one or more compounds of claim 1 or of the composition as claimed in claim 8 to at least one plant or a habitat thereof.

11. A method of reducing phytotoxic effects of pesticides on plants, the method comprising:

applying one or more compounds of the general formula (I) as claimed in claim 1 to at least one plant or a habitat thereof; and deploying at least one pesticide simultaneously or sequentially to the at least one plant or habitat thereof.

12. The method as claimed in claim 11, wherein the pesticides are one or more herbicides.

13. The method as claimed in claim 11, characterized in that compounds of the formula (I) or salts thereof as claimed in claim 1 are applied to the plants, parts of the plants, or seeds or seed material thereof.

14. The composition as claimed in claim 8, further comprising at least one formulation auxiliary.

15. The method of claim 10, further comprising use of at least one herbicide.

16. The method of claim 13, further comprising use of at least one herbicide.

* * * * *